(12) United States Patent
Tremaglio, Jr. et al.

(10) Patent No.: US 6,689,142 B1
(45) Date of Patent: Feb. 10, 2004

(54) APPARATUS AND METHODS FOR GUIDING A NEEDLE

(75) Inventors: Anthony R. Tremaglio, Jr., Hopkinton, MA (US); Michael S. H. Chu, Brookline, MA (US); Tim E. Ward, Bedford, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/450,599

(22) Filed: Nov. 30, 1999

Related U.S. Application Data

(60) Provisional application No. 60/131,058, filed on Apr. 26, 1999, and provisional application No. 60/136,291, filed on May 27, 1999.

(51) Int. Cl.[7] .......................... A61B 19/00; A61F 11/00; A61M 29/00
(52) U.S. Cl. .................. 606/130; 606/108; 604/114
(58) Field of Search ........................ 606/130, 108, 606/53, 54, 56, 87, 96, 102; 604/116

(56) References Cited

U.S. PATENT DOCUMENTS

| | | |
|---|---|---|
| 2,338,800 A | 1/1944 | Burke |
| 2,432,294 A | 12/1947 | Dimmer |
| 2,705,949 A | 4/1955 | Silverman |
| 3,115,140 A | 12/1963 | Volkman .................... 128/410 |
| 3,349,762 A | 10/1967 | Kapany |
| 3,356,089 A | 12/1967 | Francis |
| 3,457,922 A | 7/1969 | Ray |
| 3,538,916 A | 11/1970 | Wiles et al. |
| 3,556,085 A | 1/1971 | Takahashi |
| 3,941,121 A | 3/1976 | Olinger et al. |
| 3,961,621 A | 6/1976 | Northeved |
| 4,187,848 A | 2/1980 | Taylor |
| 4,230,123 A | 10/1980 | Hawkins, Jr. |
| 4,269,192 A | 5/1981 | Matsuo |
| 4,274,408 A | 6/1981 | Nimrod |

(List continued on next page.)

FOREIGN PATENT DOCUMENTS

| | | |
|---|---|---|
| DE | 295 19 103 U1 | 1/1997 |
| EP | 0 904 741 A2 | 3/1999 |
| WO | 93/10837 | 6/1993 |
| WO | 96/00044 | 1/1996 |
| WO | WO 96/33667 | 10/1996 |
| WO | WO 99/00056 | 1/1999 |
| WO | 99/16374 | 4/1999 |
| WO | 00/64354 | 11/2000 |

OTHER PUBLICATIONS

Microvasive Product Catalog; Products for Endourology, p. 8–2. 1996.
International Search Report for PCT/US99/28311, Aug. 1, 2000, 8 pages.
American Urological Association, Inc., Ureteral Stones Pamphlet, pp. 1–5, 7–8 (1997).

(List continued on next page.)

*Primary Examiner*—Sharon Kennedy
(74) *Attorney, Agent, or Firm*—Testa, Hurwitz & Thibeault, LLP

(57) ABSTRACT

A needle guiding apparatus includes a base, a guide assembly, and an imaging sight. The base defines an opening that extends through the base. The guide assembly includes at least one passage, and the guide assembly is disposed within the opening of the base. The guide assembly also is rotatable about at least one axis. The imaging sight is disposed adjacent the passage. An entry needle can be inserted through the needle guiding apparatus and into a body. Devices and methods according to the present invention allow a medical professional to accurately and rapidly place a probe, such as a needle, in a patient.

60 Claims, 42 Drawing Sheets

U.S. PATENT DOCUMENTS

| | | |
|---|---|---|
| 4,332,248 A | 6/1982 | DeVitis |
| 4,356,822 A | 11/1982 | Winstead-Hall |
| 4,401,124 A | 8/1983 | Guess et al. |
| 4,405,314 A | 9/1983 | Cope |
| 4,485,815 A | 12/1984 | Amplatz et al. |
| 4,512,351 A | 4/1985 | Pohndorf |
| 4,566,438 A | 1/1986 | Liese et al. |
| 4,572,203 A | 2/1986 | Feinstein |
| 4,582,061 A | 4/1986 | Fry |
| 4,629,451 A | 12/1986 | Winters et al. |
| 4,639,247 A | 1/1987 | Bokros |
| 4,645,490 A | 2/1987 | Rosenberg |
| 4,668,222 A | 5/1987 | Poirier |
| 4,693,703 A | 9/1987 | Rosenberg |
| 4,705,510 A | 11/1987 | Rosenberg |
| 4,710,171 A | 12/1987 | Rosenberg |
| 4,718,433 A | 1/1988 | Feinstein |
| 4,722,336 A * | 2/1988 | Kim et al. ................ 128/303 |
| 4,750,487 A * | 6/1988 | Zanetti ..................... 128/303 |
| 4,787,892 A | 11/1988 | Rosenberg |
| 4,805,615 A | 2/1989 | Carol ..................... 128/303 B |
| 4,834,708 A | 5/1989 | Pillari |
| 4,869,259 A | 9/1989 | Elkins |
| 4,874,376 A | 10/1989 | Hawkins, Jr. |
| 4,875,478 A * | 10/1989 | Chen ........................ 128/303 |
| 4,886,502 A | 12/1989 | Poirier et al. |
| 4,897,081 A | 1/1990 | Poirier et al. |
| 4,899,729 A | 2/1990 | Gill et al. |
| 4,945,895 A | 8/1990 | Takai et al. |
| 4,977,897 A | 12/1990 | Hurwitz |
| 4,981,142 A | 1/1991 | Dachman |
| 4,997,424 A | 3/1991 | Little |
| 4,998,938 A | 3/1991 | Ghajar et al. ............. 606/130 |
| 5,006,115 A | 4/1991 | McDonald |
| 5,009,644 A | 4/1991 | McDonald |
| 5,020,088 A | 5/1991 | Tobin ........................ 378/164 |
| 5,047,036 A | 9/1991 | Koutrouvelis |
| 5,048,530 A | 9/1991 | Hurwitz |
| 5,056,523 A * | 10/1991 | Hotchkiss, Jr. et al. ..... 128/653 |
| 5,059,186 A | 10/1991 | Yamamoto et al. |
| 5,078,142 A | 1/1992 | Siczek et al. |
| 5,080,662 A | 1/1992 | Paul |
| 5,081,997 A | 1/1992 | Bosley, Jr. et al. |
| 5,098,397 A | 3/1992 | Svensson et al. |
| 5,104,381 A | 4/1992 | Gresl et al. |
| 5,129,911 A | 7/1992 | Siczek et al. |
| 5,135,001 A | 8/1992 | Sinofsky et al. |
| 5,139,511 A | 8/1992 | Gill et al. |
| 5,189,690 A | 2/1993 | Samuel |
| 5,201,314 A | 4/1993 | Bosley et al. |
| 5,201,742 A | 4/1993 | Hasson |
| 5,221,269 A | 6/1993 | Miller et al. |
| 5,242,415 A | 9/1993 | Kantrowitz et al. |
| 5,242,455 A | 9/1993 | Skeens et al. |
| 5,250,025 A | 10/1993 | Sosnowski et al. |
| 5,251,127 A * | 10/1993 | Raab ........................ 364/413.3 |
| 5,259,837 A | 11/1993 | Van Wormer |
| 5,263,938 A | 11/1993 | Orr et al. |
| 5,289,831 A | 3/1994 | Bosley |
| 5,308,352 A | 5/1994 | Koutrouvelis |
| 5,314,432 A | 5/1994 | Paul |
| 5,327,891 A | 7/1994 | Rammler |
| 5,383,466 A | 1/1995 | Partika |
| 5,395,317 A | 3/1995 | Kambin |
| 5,409,497 A | 4/1995 | Siczek et al. |
| 5,439,444 A | 8/1995 | Andersen et al. |
| 5,489,273 A | 2/1996 | Whitney et al. |
| 5,490,521 A | 2/1996 | Davis et al. |
| 5,556,385 A | 9/1996 | Andersen |
| 5,571,091 A | 11/1996 | Davis et al. |
| 5,575,798 A | 11/1996 | Koutrouvelis |
| 5,586,553 A | 12/1996 | Halili et al. |
| 5,588,436 A | 12/1996 | Narayanan et al. |
| 5,626,597 A | 5/1997 | Urban et al. |
| 5,665,072 A | 9/1997 | Yoon |
| 5,665,095 A | 9/1997 | Jacobson ..................... 606/130 |
| 5,670,161 A | 9/1997 | Healy et al. |
| 5,676,656 A | 10/1997 | Brimhall |
| 5,680,859 A | 10/1997 | Urion et al. |
| 5,693,072 A | 12/1997 | McIntosh |
| 5,725,506 A | 3/1998 | Freeman et al. |
| 5,749,887 A | 5/1998 | Heske et al. |
| 5,759,154 A | 6/1998 | Hoyns |
| 5,766,135 A | 6/1998 | Terwilliger |
| 5,769,795 A | 6/1998 | Terwilliger |
| 5,779,665 A | 7/1998 | Mastrototaro et al. |
| 5,792,044 A | 8/1998 | Foley et al. |
| 5,792,146 A * | 8/1998 | Cosman ..................... 606/130 |
| 5,799,055 A | 8/1998 | Peshkin et al. |
| 5,820,554 A | 10/1998 | Davis et al. |
| 5,820,600 A | 10/1998 | Carlson et al. |
| 5,830,190 A | 11/1998 | Howell |
| 5,833,655 A | 11/1998 | Freed et al. |
| 5,843,023 A | 12/1998 | Cecchi |
| 5,851,183 A | 12/1998 | Bucholz |
| 5,871,445 A | 2/1999 | Bucholz |
| 5,902,231 A | 5/1999 | Foley et al. |
| 5,921,933 A | 7/1999 | Sarkis et al. |
| 5,967,988 A | 10/1999 | Briscoe et al. |
| 5,972,030 A * | 10/1999 | Garrison et al. ............... 623/2 |
| 6,006,750 A | 12/1999 | Field |
| 6,018,676 A | 1/2000 | Davis et al. |
| 6,019,724 A * | 2/2000 | Gronningsaeter et al. ... 600/439 |
| 6,053,871 A | 4/2000 | Cockburn |
| 6,080,181 A * | 6/2000 | Jensen et al. ............... 606/205 |
| 6,106,473 A | 8/2000 | Violante et al. |
| 6,106,511 A * | 8/2000 | Jensen .......................... 606/1 |
| 6,374,135 B1 * | 4/2002 | Bucholz ..................... 600/427 |

OTHER PUBLICATIONS

Boston Scientific/Microvasive Education Center, "Percutaneous Nephrolithotomy," pp. 1–10 (1995).

Cadeddu et al., "Stereotactic Mechanical Percutaneous Renal Access," *Journal of Endourology*, vol. 12, No. 2, (Apr. 1998).

Caronia et al., "Rettopessi per via laparoscopica: nostra esperienza nel trattamento del prolasso rettale completo," *Giorn. Chir.*, vol. 20–n.6/7, pp. 311–313, (1999), with English Abstract.

Cook Urological, Inc., "Disposable Two–Part Trocar Needles," 1 page, (1998).

Cook Urological, Inc., "Amplatz Needle Holder," 1 page, (1998).

Cook Urological, Inc., "Disposable Long Trocar Needles," 1 page, (1998).

Cook Urological, Inc., "Disposable Mitty–Pollack Needle Set," 1 page, (1998).

Cook Urological, Inc., "Disposable TFE Sheath Needle," 1 page, (1998).

Cook Urological, Inc., "Cook–Cope Look Catheter Introduction Set," 1 page, (1998).

Cook Urological, Inc., "Percutaneous Entry Set," 2 pages, (1998).

Cook Urological, Inc., "NEFF Percutaneous Access Sets with RB™ Design Radiopaque Band," 1 page, (1995).

Cook Urological, Inc., "NEFF Percutaneous Access Sets with Radiopaque Band and Hydrophilic Coating," 2 pages, (1997).

Cook Urological, Inc., "Ultrathane® Amplatz Ureteral Stent Sets with Slip–Coat™ Hydrophilic Coating and RB™ Radiopaque Bands," 1 page, (1996).

Cook Urological, Inc., "Ultrathane Dawson–Mueller Drainage Catheters with Mac–Loc™ Locking Mechanism, Slip–Coat™ Hydrophilic Coating and Intro–Tip™ Design Introduction System," 1 page, (1997).

Cook Urological, Inc., "Yueh Centesis Disposable Catheter Needles," 1 page, (1996).

Cook Urological, Inc., "Geremia Vertebral Biopsy Needle Set," 1 page, (1994).

Engineering News, "Engineers Keep Things Green," *Design News*, (Nov. 2, 1998).

Fielding, "Laparoscopic Cholecystectomy," *Aust. N.Z. J. Surg.*, vol. 62, pp. 181–187, (1992).

Gotlieb et al., "Intraperitoneal Pressures and Clinical Parameters of Total Paracentesis for Palliation of Symptomatic Ascites in Ovarian Cancer," *Gynecologic Oncology*, vol. 71, pp. 381–385, (1998).

Jenkins et al., "Veres Needle in the Pleural Space," *Southern Medical Journal*, vol. 76, No. 11, pp. 1383–1385, (Nov. 1983).

Köckerling et al., "Die Offene Laparoskopie zur Vermeidung von Punktionsverletzungen," *Chirurg*, vol. 67, pp. 183–187, (1996), with English summary section.

LeRoy, "Percutaneous Access," in *Smith's Textbook of Endourology*, vol. 1, pp 199–210, (1996).

Smith, "Percutaneous Removal of Kidney Stones," Urologic Surgery, pp. 116–131 (date unknown).

PCT International Search Report, PCT/US02/39187, 8 pages, issued on Apr. 16, 2003.

* cited by examiner

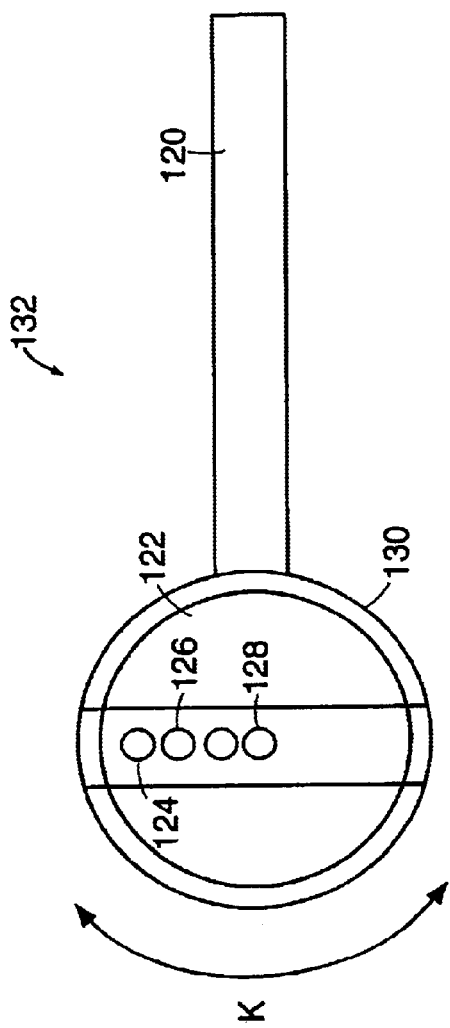
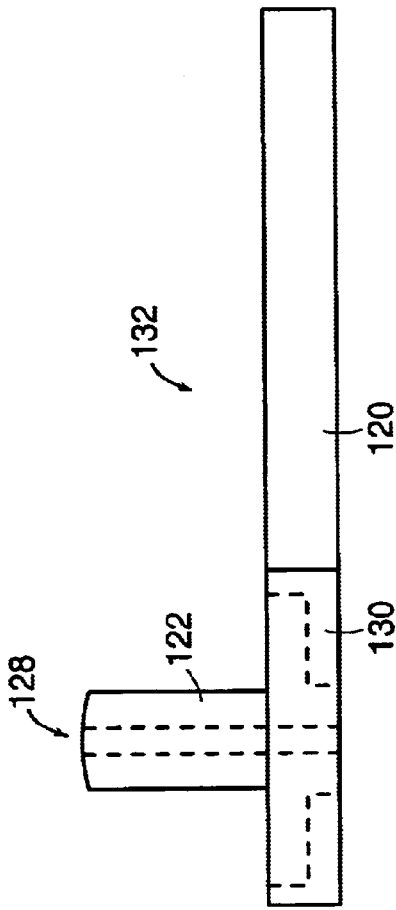
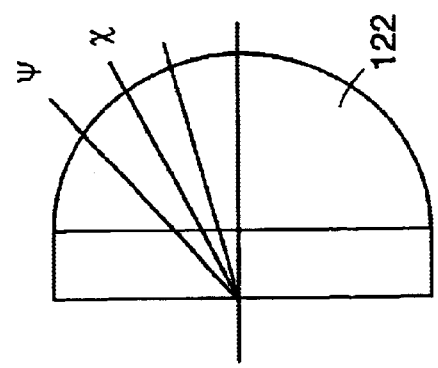
FIG. 12
FIG. 13
FIG. 14

FIG. 18B
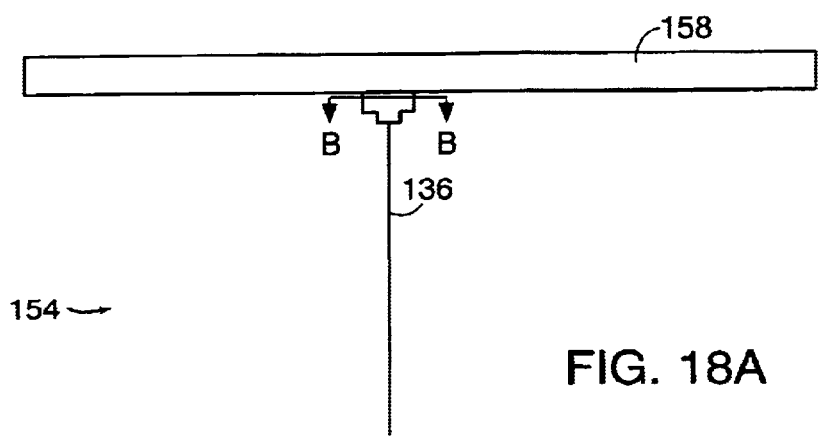
FIG. 18A
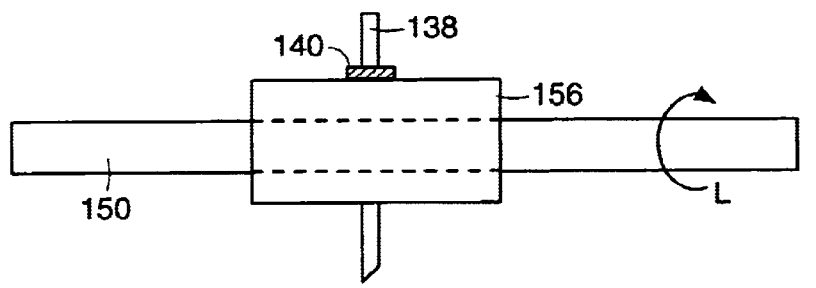
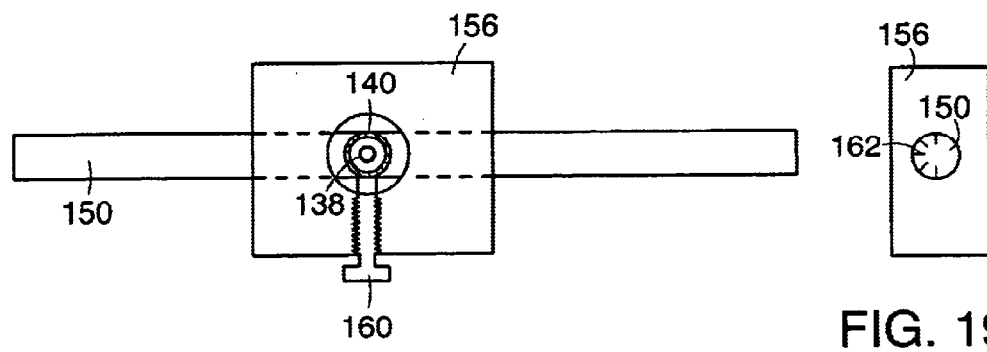
FIG. 19A
FIG. 19B

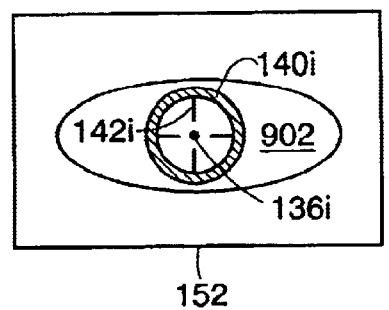
FIG. 21
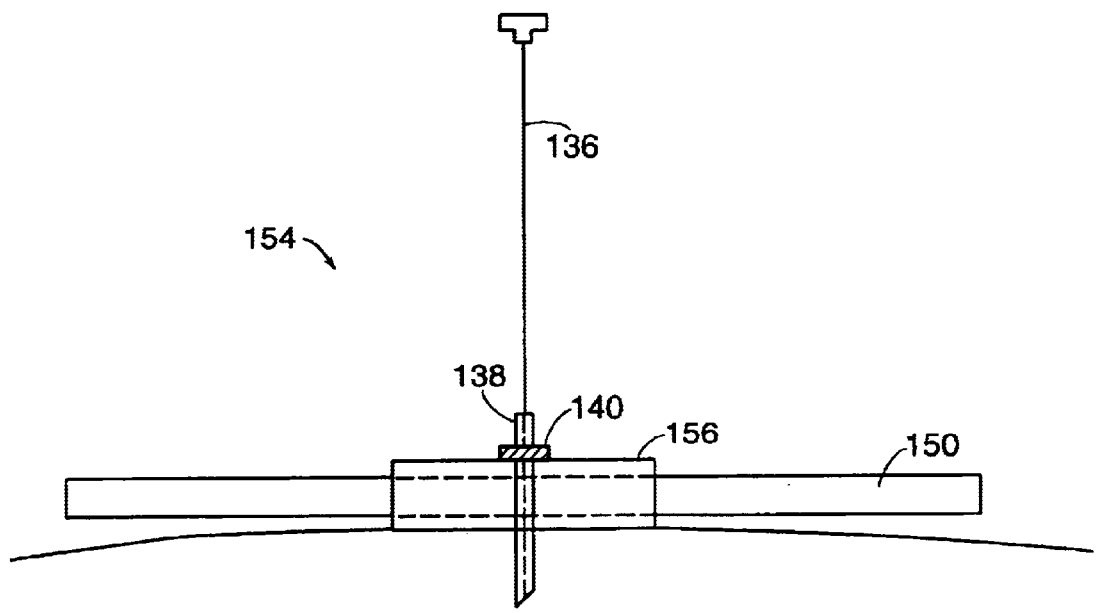
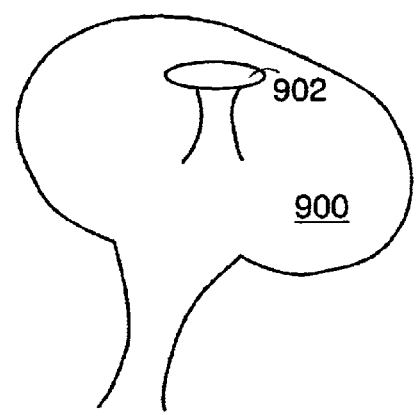
FIG. 20

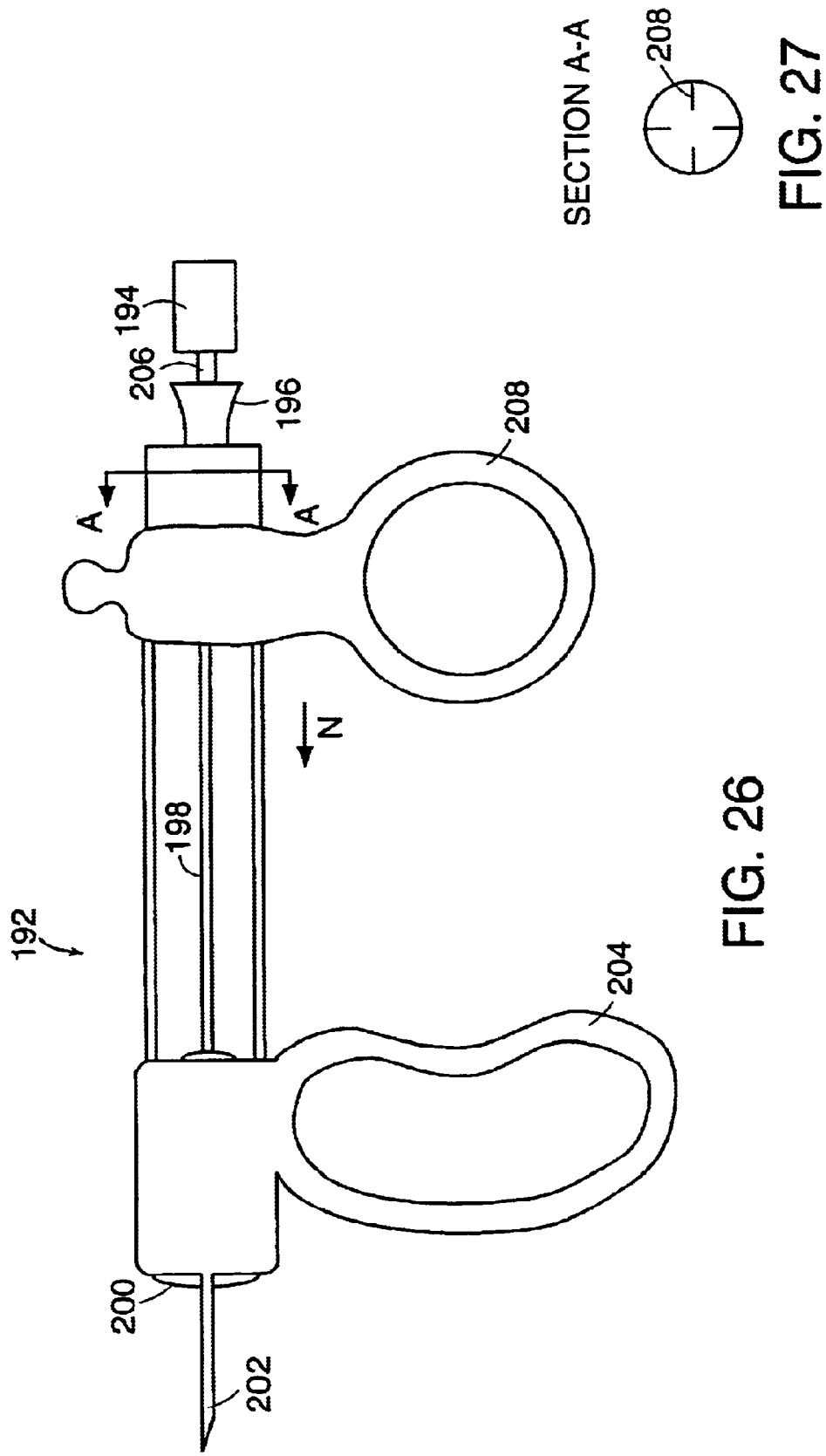

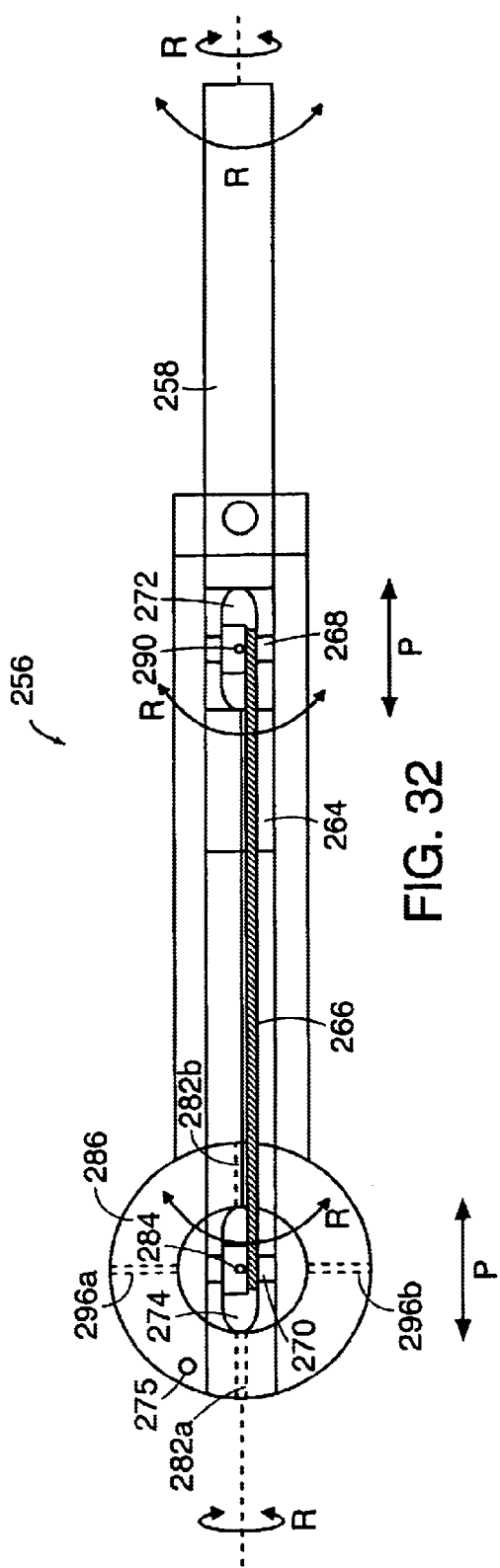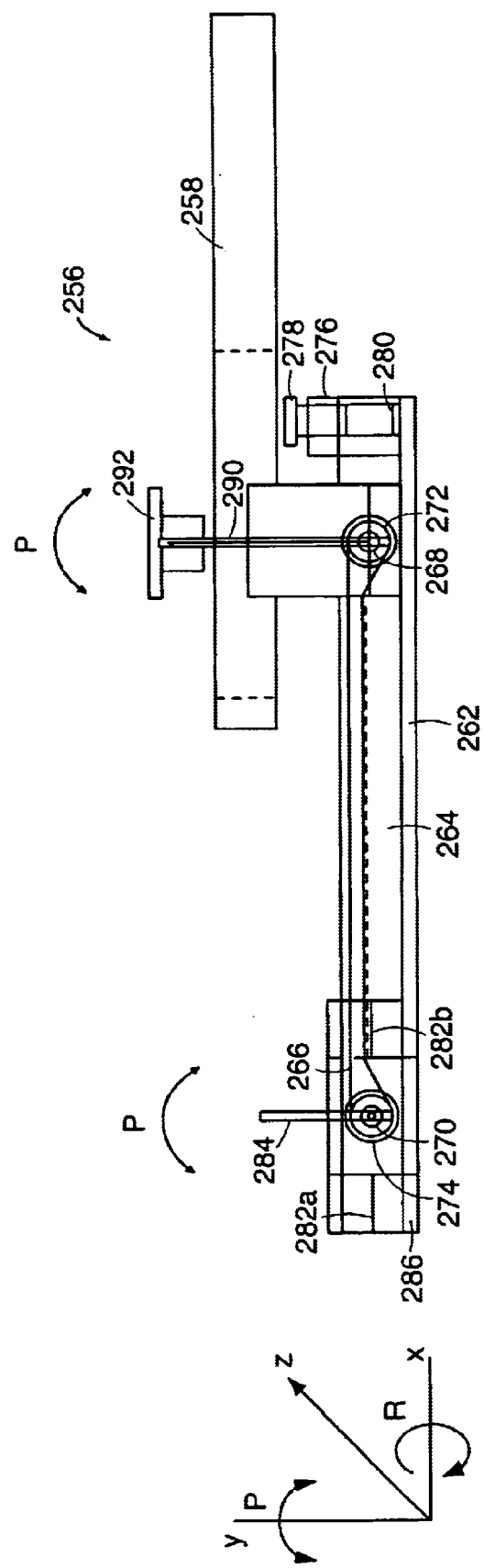

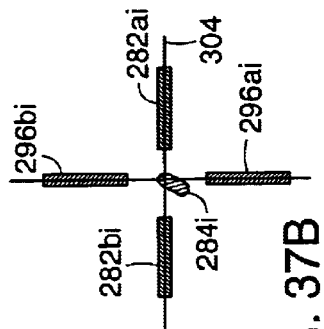
FIG. 37B
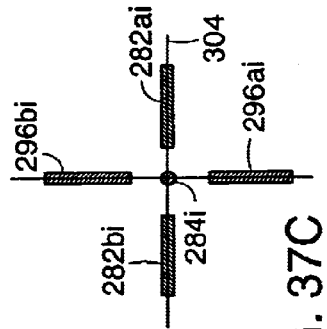
FIG. 37C
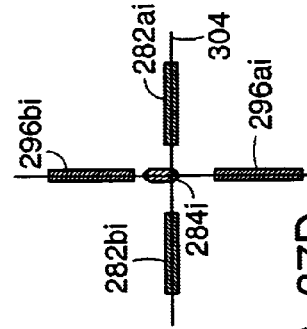
FIG. 37D
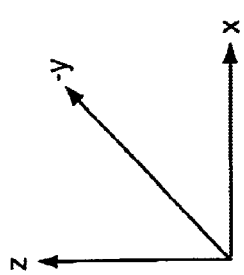
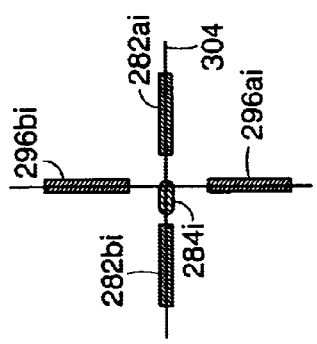
FIG. 37A
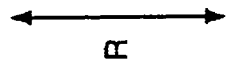

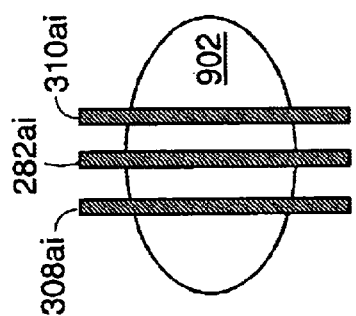
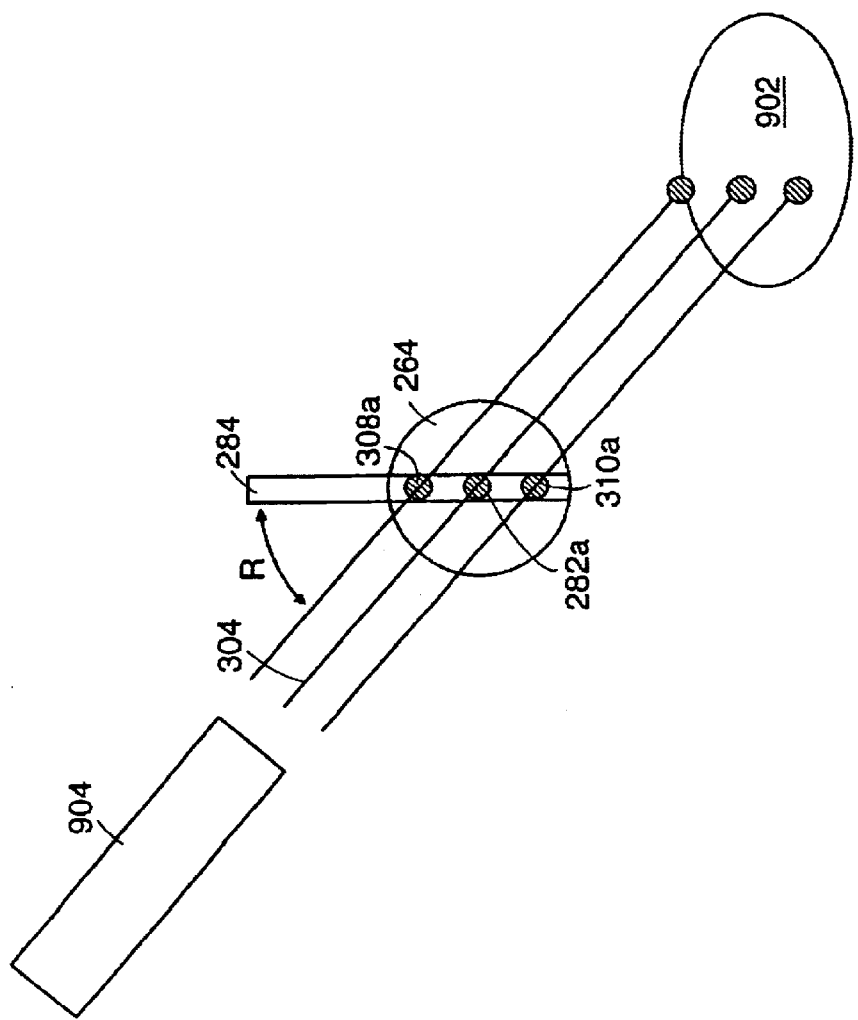
FIG. 40B
FIG. 40A

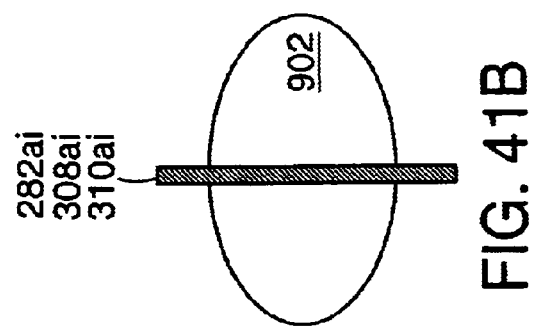
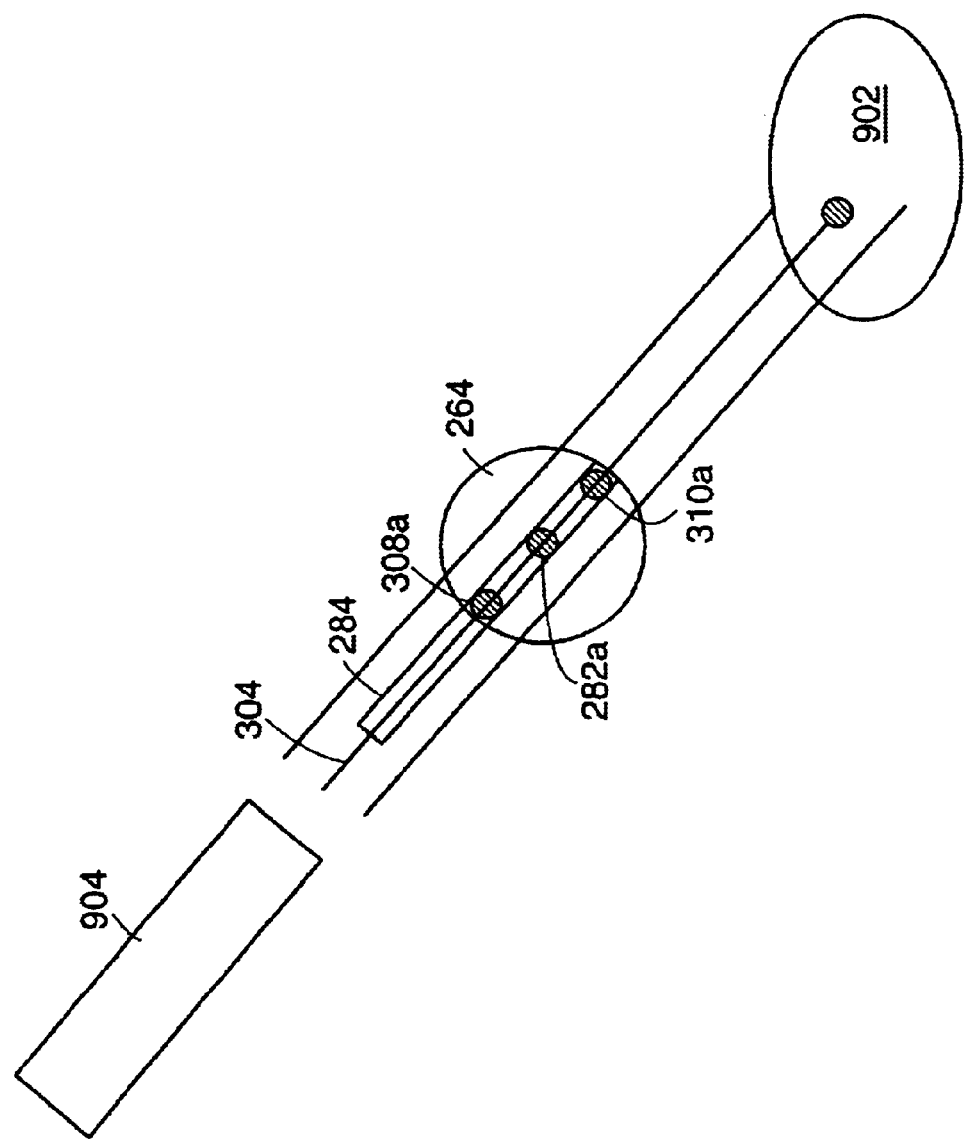
FIG. 41B
FIG. 41A

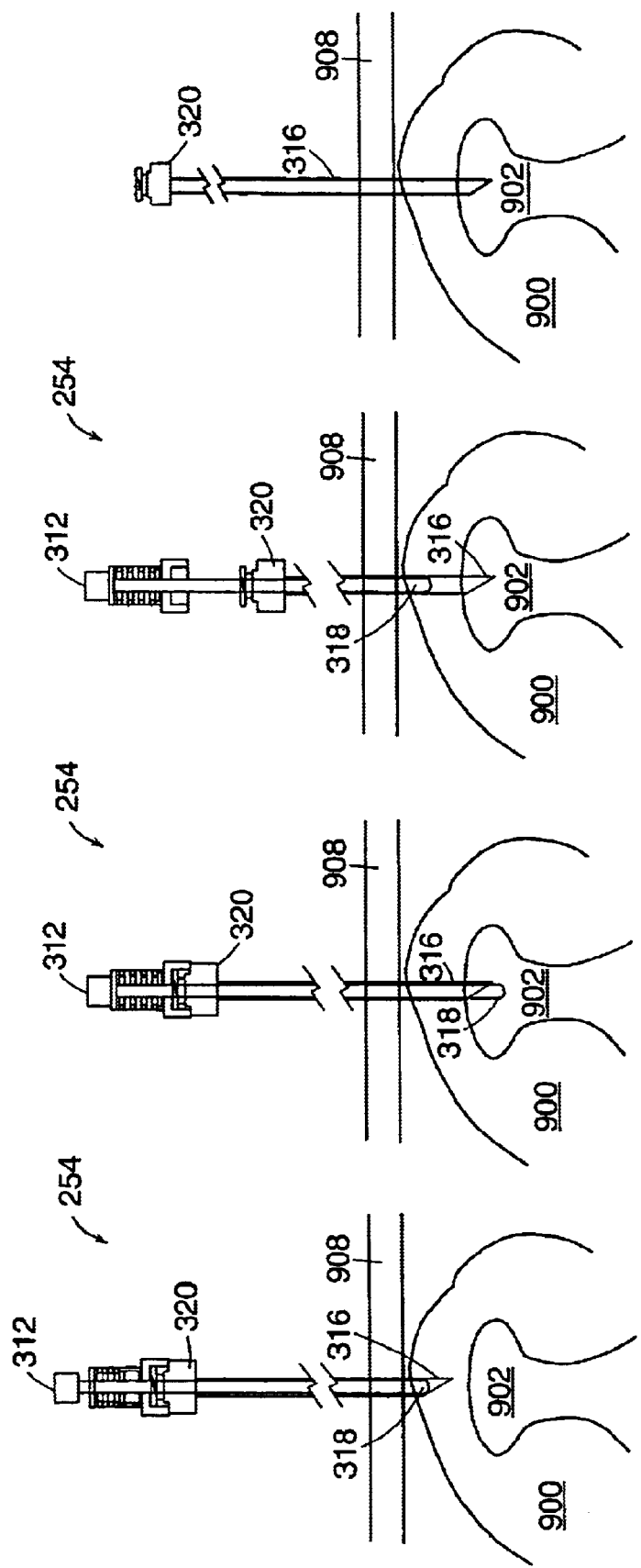

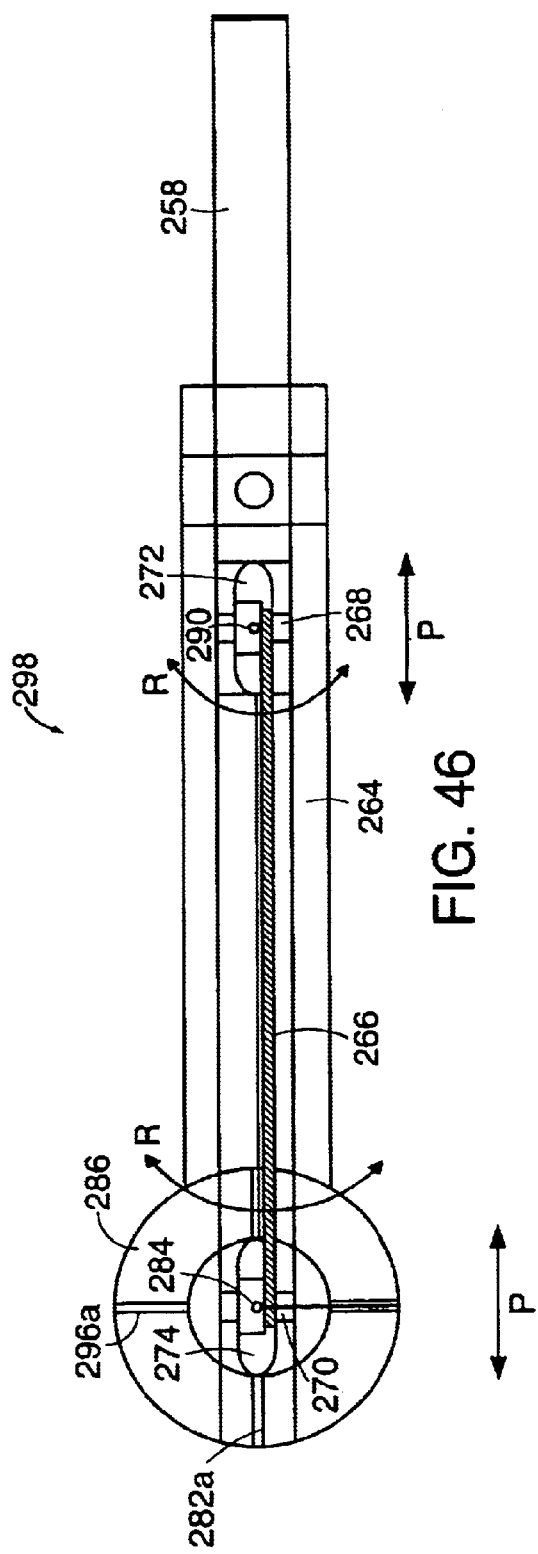
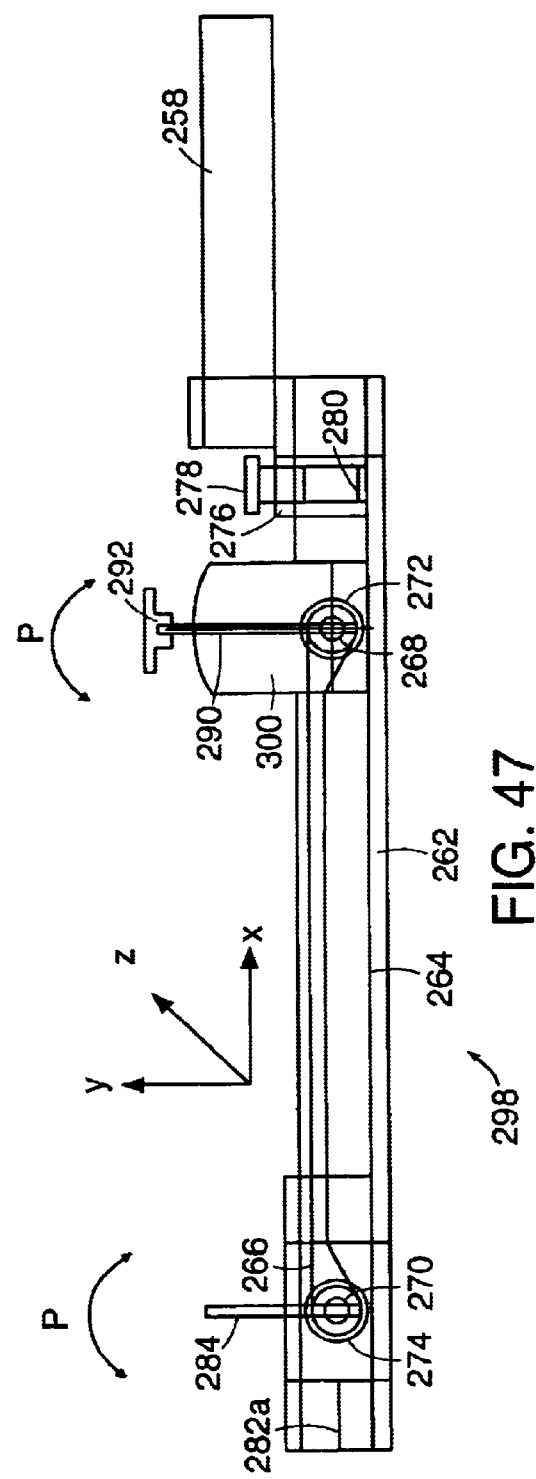

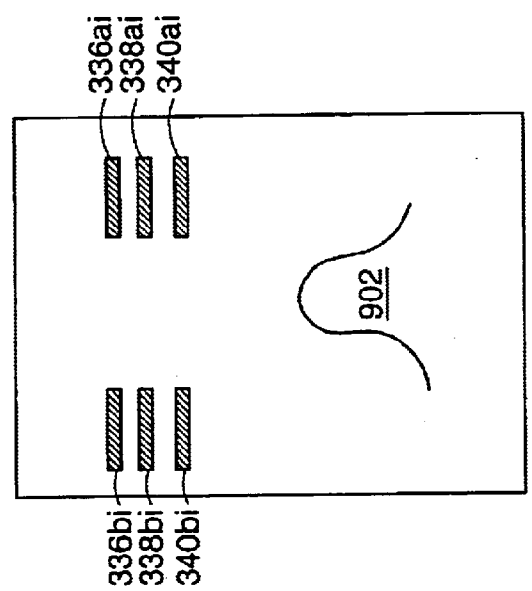
FIG. 49C
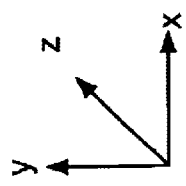
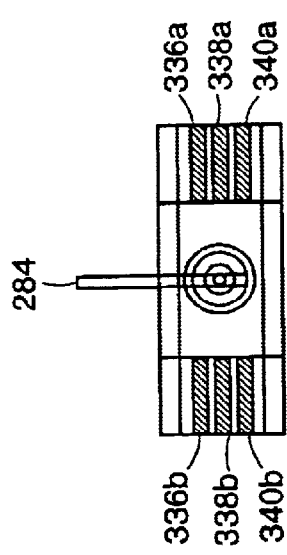
FIG. 49A
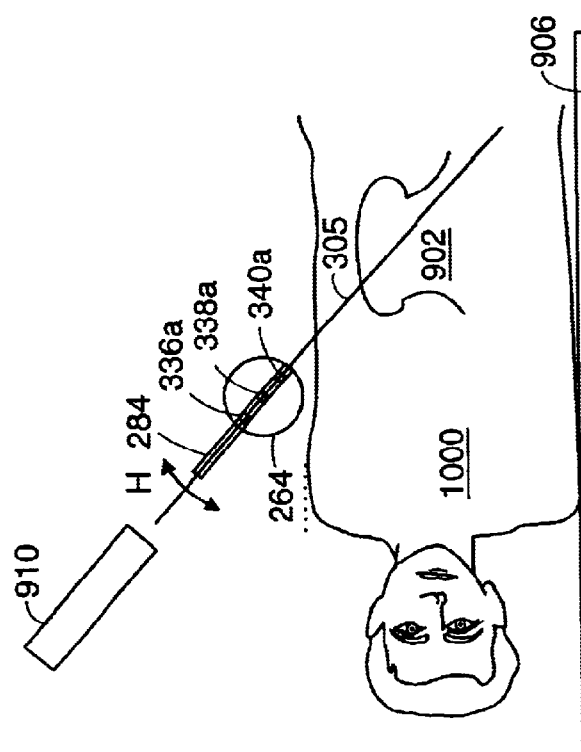
FIG. 49B

APPARATUS AND METHODS FOR GUIDING A NEEDLE

CROSS-REFERENCE TO RELATED APPLICATIONS

The present application claims priority to and the benefit of U.S. provisional patent application serial No. 60/131,058, filed Apr. 26, 1999, and U.S. provisional patent application serial No. 60/136,291, filed May 27, 1999. The entire disclosure of each of these provisional patent applications is incorporated herein by reference.

TECHNICAL FIELD

The present invention relates to apparatus and methods for introducing a needle into a body. More particularly, the invention relates to apparatus and methods for introducing a needle into a body in a particular orientation and in a stable manner.

BACKGROUND INFORMATION

Many medical procedures are undertaken through small tracts formed within a patient's tissue. These procedures are minimally invasive. In order to form the tract running from outside of the patient to a target within the patient, a probe typically is inserted in the initial stages of a procedure. This probe will run from the surface of the patient's skin to the target. Later in the procedure, this initial insertion can be enlarged to accommodate other medical devices necessary for the procedure.

Typically, inserting the probe is a time-consuming procedure. The probe must be positioned properly, typically under the guidance of an energy emitting medical device, such as an x-ray emitting device. X-ray energy passes through the patient's body and differentially impinges on a fluoroscope screen, exciting fluorescent material, such as calcium tungstate, to create a screen display of the body and probe. The probe is visualized on the fluoroscope as it enters the patient on the display of the medical device. This probe can appear on the screen because it does not allow the energy to pass through it (i.e., it can be opaque).

SUMMARY OF THE INVENTION

The present invention allows for the positioning and insertion of a probe, such as a needle, into a patient. A medical professional manipulates devices according to the invention such that a properly aligned device will properly align an entry needle with a target in the patient's body. Some of the advantages of these devices include shortening the length of a procedure, allowing for a more precise positioning of an entry needle which can, for example, reduce trauma to tissue, and stabilizing the entry needle during placement. Specific embodiments can have these and other advantages described below.

In one aspect of the invention, a needle guiding apparatus includes a base defining an opening extending therethrough; a guide assembly including at least one passage and being disposed within the opening; and an imaging sight disposed adjacent at least one passage. The guide assembly is rotatable about at least one axis This aspect or any of the other aspects of the invention can have any of the following features. The guide assembly can include a first transmission element between a first location within the opening and a second location remote therefrom. The first transmission element can be for transferring angular movement between the second location and the first location, and the movement at the first location can occur about a first one of the axes. The first transmission element can include a first pulley proximate the first location and disposed coaxially with the first axis of rotation and/or can further include a guide shaft defining at least a portion of the at least one passage. Also, the first transmission element can include a belt for transferring angular movement between the first location and the second location and/or can include a control shaft connected to a second pulley proximate the second location. The needle guiding apparatus also can include a lock for preventing movement of the first transmission element.

The guide assembly can include a second transmission element for transferring angular movement about a second one of the axes. The second transmission element can include an adjustment rod rotatable about the second axis extending through the adjustment rod. The imaging sight can include a radiopaque core of the adjustment rod. The imaging sight can include at least two parallel bars disposed within the adjustment rod. The needle guiding apparatus can include a lock for preventing movement of the adjustment rod. The first axis and the second axis can be substantially perpendicular. The imaging sight can include a radiopaque band disposed within the base. The guide assembly can include an adjustment rod. The adjustment rod can be rotatable about an axis extending through the adjustment rod and/or can be rotatable about an axis extending through the passage.

The guide assembly can include a turret disposed within the opening. The turret can include an adjustment rod. The turret can be rotatable about an axis extending through the opening, and/or the adjustment rod can be rotatable about an axis extending through the adjustment rod. The guide assembly can include a guide needle. The guide assembly can include a ball and socket joint disposed within the base and can further include a guide shaft defining a portion of the passage and/or can further include a control arm connected to the guide assembly and/or can further include a second ball and socket joint connected to the control arm, thereby to replicate the movement of the second ball and socket joint at the guide assembly. The second joint can be capable of locking into a position.

The imaging sight can be disposed coaxially about at least one passage, and/or the imaging sight can include a ring, and/or the imaging sight can include at least one cross-hair. The imaging sight can include a material that is detectable with a fluoroscope, and the material that is detectable with a fluoroscope can include a radiopaque material. The guide assembly can include at least two of the passages, and the passages can be disposed at known angles relative to the base. The needle guiding apparatus can include at least one clamp for attaching the apparatus to a fixed surface. The guide assembly can be capable of locking into a position. At least two of the axes about which the guide assembly rotates can be substantially perpendicular The needle guiding apparatus can include an entry needle, the needle capable of inserting through the passage. Any entry needle can include radiopaque cross-hairs to aid with aligning a needle guiding apparatus and/or the entry needle. The entry needle can include a first assembly that includes a housing, a stylet extending into the housing and biased towards a distal end of the entry needle, and a hub adjacent the housing at a proximal end of the entry needle and in connection with the stylet, and the entry needle can include a second assembly that includes a cannula surrounding the stylet. The first assembly and the second assembly can seal together and can be separable. The hub can be movable from a first position to a second position, the hub in the first position indicating that the entry needle is impeded by a tissue and the hub in the second position indicating that the entry needle is not substantially impeded by the tissue. The stylet can include a blunt edge at its distal end, and/or the cannula can include an angled edge at its distal end, and/or the stylet can include an angled edge at its distal end, and/or the cannula can include a blunt edge at its distal end. The entry needle can include a connector connected with the cannula for attaching a medical device to the entry needle.

The entry needle can include an inner needle coaxially surrounded by a cannula having an outer wall defining a lumen. The cannula can have an opening in the outer wall proximate a distal end of the entry needle and a branch proximate a proximal end of the entry needle, the inner needle including a notch. The inner needle can be rotatable from a first position to a second position, the notched inner needle in the first position allowing communication between the opening and the branch and the notched inner needle in the second position preventing communication between the opening and the branch. The branch can be capable of attaching to a suction device.

The entry needle can include an electromagnetic energy sensor. The entry needle can include a chemical sensor. The guide assembly can be constructed such that it does not protrude past at least one side of the base.

In another aspect of the invention, a method for aiming a needle guiding apparatus includes the steps of providing a needle guiding apparatus that includes a base having an opening, a guide assembly defining at least one passage and disposed within the opening, the guide being rotatable about at least one axis, and an imaging sight disposed adjacent the at least one passage; aligning the imaging sight with at least a portion of a target, and with an energy source; and viewing the sight on a display. The providing step can include providing a needle guiding apparatus that includes an imaging sight that can be ring of radiopaque material, a bar of radiopaque material, a cross-hair of radiopaque material, cross-hairs of radiopaque material, perpendicular bars of radiopaque material, and/or a diamond shape of radiopaque material, and combinations thereof. The viewing step can include viewing the imaging sight on the display, the imaging sight appearing to surround at least the portion of the target and at least a portion of the guide assembly, thereby indicating proper alignment. The guide assembly can include a guide shaft, and the viewing step can include viewing the imaging sight on the display, the imaging sight appearing to surround the guide shaft and at least the portion of the target, thereby indicating proper alignment.

In another aspect of the invention, a needle guiding apparatus includes a base defining an opening extending therethrough; a guide assembly including a turret rotatably mounted in the opening and an adjustment rod rotatably mounted in the turret, the guide assembly including at least one passage therethrough; and an imaging sight disposed adjacent at least one passage. The turret can include a groove for interlocking with pins from the base, thereby to allow rotation of the turret within the base. Alternatively, the turret can be associated with the base using a friction fit, thereby to allow rotation of the turret within the base. The guide assembly can be constructed such that it does not protrude beyond at least one side of the base.

In another aspect of the invention, a needle guiding apparatus includes a base including a socket; a guide assembly including at least one passage therethrough and including a ball articulable within the socket and a guide shaft proximate the ball; and an imaging sight disposed adjacent at least one passage. The needle guiding apparatus also can include a connecting rod in operable connection with the guide assembly and with a mechanism, the mechanism being remote from the guide assembly, thereby to replicate movements of the mechanism at the guide assembly. The mechanism can include a base assembly that includes a socket, a ball being articulable in the socket, and a shaft proximate the ball. The needle guiding apparatus also can include a lock, thereby to prevent movement of the guide assembly. The base can include an opening extending therethrough and the guide assembly can be disposed within the opening.

In another aspect of the invention, a needle guiding apparatus includes a base, a dome, and a guide assembly that includes a stop and defines a passage, such that the guide assembly is positionable at various locations through the dome and the guide assembly does not protrude beyond at least one surface of the base. The dome can include an imaging sight.

In another aspect of the invention, a needle guiding apparatus includes a base defining an opening extending therethrough; a guide assembly including a turret rotatable within the opening, the turret defining at least two passages therethrough, the passages being at known angles of entry relative to the base; and an imaging sight adjacent at least one passage.

In another aspect of the invention, a needle guiding apparatus includes a base defining an opening extending therethrough; a guide assembly including a guide needle including a passage therethrough, the guide needle being rotatable about an axis that extends through the base and is substantially perpendicular to the guide needle; and an imaging sight adjacent the passage. The needle guiding apparatus also can include at least one driving bar for inserting an entry needle through the passage and/or can include at least one bar guide for sliding at least one driving bar along a predetermined range of motion. The needle guiding apparatus also can include at least one driving bar for applying force to the guide assembly and/or include at least one bar guide, such that at least one driving bar is affixed to the at least one bar guide and that applied force is conveyed from the at least one driving bar to the guide assembly.

In another aspect of the invention, a needle guiding apparatus includes a base defining an opening extending therethrough; a guide assembly including an adjustment rod rotatable about an axis extending through the adjustment rod and a guide needle extending through the adjustment rod and defining a passage extending therethrough; and an imaging sight adjacent the passage. The needle guiding apparatus also can include a lock for preventing movement of the alignment rod. The needle guiding apparatus also can include at least one driving bar associated with an entry needle for applying force to the entry needle, the entry needle passing through the passage, and/or at least one bar guide for sliding at least one driving bar along a predetermined range of motion. The needle guiding apparatus also can include at least one driving bar for applying force to the guide assembly, and/or at least one bar guide, such that at least one driving bar is affixed to the at least one bar guide and that applied force is conveyed from the at least one driving bar to the guide assembly.

In another aspect of the invention, an entry needle can include a first assembly that includes a housing, a stylet extending into the housing and biased towards a distal end of the entry needle, and a hub adjacent the housing at a proximal end of the entry needle and in connection with the stylet. The entry needle also can include a second assembly that includes a cannula surrounding the stylet. The first assembly and the second assembly can seal together and can be separable. The hub can be movable from a first position to a second position, the hub in the first position indicating that the entry needle is impeded by a tissue and the hub in the second position indicating that the entry needle is substantially unimpeded by the tissue. The stylet can include a blunt edge at its distal end, and/or the cannula can include an angled edge at its distal end, and/or the stylet can include an angled edge at its distal end, and/or the cannula can include a blunt edge at its distal end. The entry needle also can include a connector connected with the cannula for attaching a medical device to the entry needle.

In another aspect of the invention, a needle guiding apparatus includes a position holding device; a needle disposed within and coaxially with the position holding device; a front aiming device proximate a distal end of the needle guiding apparatus and disposed coaxially about the needle; and a rear aiming device proximate a proximal end of the needle driving apparatus and disposed coaxially about the needle. The position holding device can include a needle. At least a portion of the position holding device can be radiopaque. At least a portion of the needle can be radiopaque. At least a portion of the front aiming device can be radiopaque. The front aiming device can include a circular portion. At least a portion of the rear aiming device can be radiopaque. The rear aiming device can include at least one cross-hair. The needle guiding apparatus also can include a trigger for delivering the needle. The needle guiding apparatus also can include a cannula having an outer wall defining a lumen and being coaxially disposed about the needle. The cannula can have an opening in the outer wall proximate the distal end and a branch proximate the proximal end, and the needle can include a notch. The needle can be rotatable from a first position to a second position, the notched needle in the first position allowing communication between the opening and the branch and the notched needle in the second position preventing communication between the opening and the branch. The branch can be capable of attaching to a suction device. A cannula can include an electromagnetic energy sensor. A cannula can include a chemical sensor.

In another aspect of the invention, a method of aiming a needle guiding apparatus includes the steps of providing a needle guiding apparatus that includes a position holding device, a needle disposed within and coaxially with the position holding device, a front aiming device proximate a distal end of the needle driving apparatus and disposed coaxially about the needle, and a rear aiming device proximate a proximal end of the needle driving apparatus and disposed coaxially about the needle; aligning a distal end of the needle with a target; aligning an energy source with an axis of the needle and the target; and aligning the distal end of the needle, the center of the front aiming device, and the center of the rear aiming device with the target.

BRIEF DESCRIPTION OF THE DRAWINGS

The invention, and exemplary embodiments according to the invention, are more particularly described in the following description, taken in conjunction with the accompanying drawings.

In the drawings, like reference characters generally refer to the same parts throughout the different views. Also, the drawings are not necessarily to scale, emphasis instead generally being placed upon illustrating principles of the invention.

FIG. 12 depicts a schematic top view of a device with a turret containing passages at known angles relative to a base, according to the invention.

FIG. 13 depicts a schematic side view of the embodiment of FIG. 12.

FIG. 14 depicts a schematic side view of the dome of the embodiment of FIG. 12.

FIG. 18A depicts a schematic side view of a device with an adjustment rod and a guide needle, according to the invention.

FIG. 18B depicts a schematic cross-section taken through line B—B of the embodiment of FIG. 18A.

FIG. 19A depicts a schematic top view of the embodiment of FIG. 18A;

FIG. 19B depicts a schematic partial side view of the embodiment of FIG. 19A.

FIG. 20 depicts a schematic top view of the embodiment of FIG. 18A relative to a patient's skin and a target.

FIG. 21 depicts a schematic representation of a screen display of the embodiment of FIG. 18A while the device is in use.

FIG. 26 depicts a schematic side view of a device for driving an entry needle.

FIG. 27 depicts a schematic view through a cross-section of a sight along line A—A of the embodiment of FIG. 26.

FIG. 32 depicts a schematic top view of the needle guide apparatus of FIG. 31.

FIG. 33 depicts a schematic side view of the needle guide apparatus of FIG. 31 without the entry needle.

FIG. 37A depicts a schematic view of a display in which a guide shaft of the embodiment of FIG. 31 is symmetric about a first axis.

FIG. 37B depicts a schematic view of a display in which a guide shaft of the embodiment of FIG. 31 is not symmetric about a first axis.

FIG. 37C depicts a schematic view of a display in which a guide shaft of the embodiment of FIG. 31 is symmetric about a first and second axis.

FIG. 37D depicts a schematic view of a display in which a guide shaft of the embodiment of FIG. 31 is not symmetric about a first axis.

FIG. 40A depicts a schematic end view of a slightly altered embodiment of the device of FIG. 31 with a guide shaft that is not aligned with a target.

FIG. 40B depicts a schematic image display with the device of FIG. 40A in the position indicated in FIG. 40A.

FIG. 41A depicts a schematic end view of a slightly altered embodiment of the device of FIG. 31 with a guide shaft that is aligned with a target.

FIG. 41B depicts a schematic image display with the device of FIG. 41A in the position indicated in FIG. 41A.

FIG. 44A depicts a schematic sectional view of the embodiment of FIG. 42A as the entry needle enters a kidney.

FIG. 44B depicts a schematic sectional view of the embodiment of FIG. 42A as the entry needle enters a target calyx.

FIG. 44C depicts a schematic sectional view of the embodiment of FIG. 42A as the stylet is removed from the cannula.

FIG. 44D depicts a schematic sectional view of the embodiment of FIG. 42A after the stylet is removed and the cannula with connector is left behind.

FIG. 46 depicts a schematic top view an embodiment similar to that of FIG. 31 having a slightly different control for guiding an entry needle.

FIG. 47 depicts a schematic side view of the embodiment of FIG. 46.

FIG. 49A depicts a schematic side view of a portion of a slightly altered embodiment of the device of FIG. 31 for use with an MRI device or a CAT-scan device.

FIG. 49B depicts a schematic end view of a slightly altered embodiment of the device of FIG. 31 that is aligned with a target and that is for use with an MRI device or a CAT-scan device.

FIG. 49C depicts a schematic image display with the device of FIG. 49A in the position indicated in FIG. 49B.

DESCRIPTION

Figure 1:
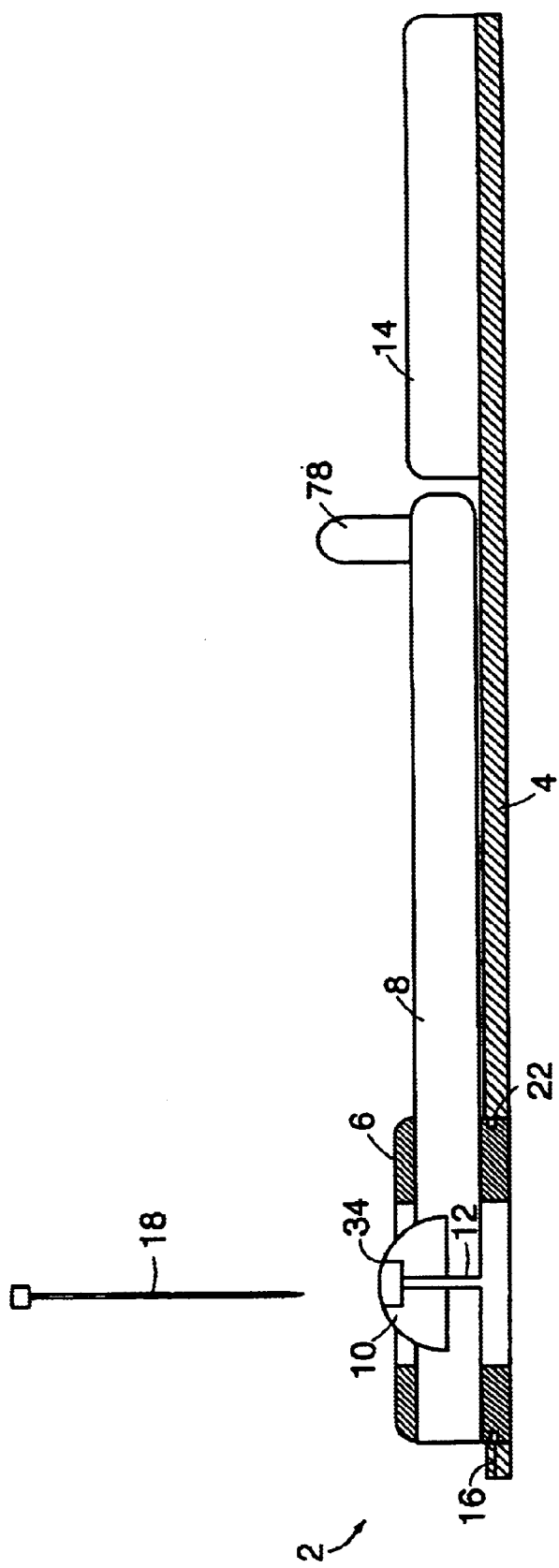
FIG. 1 depicts a schematic side view of a device with a turret and an adjustment rod, according to the invention.
Figure 2:
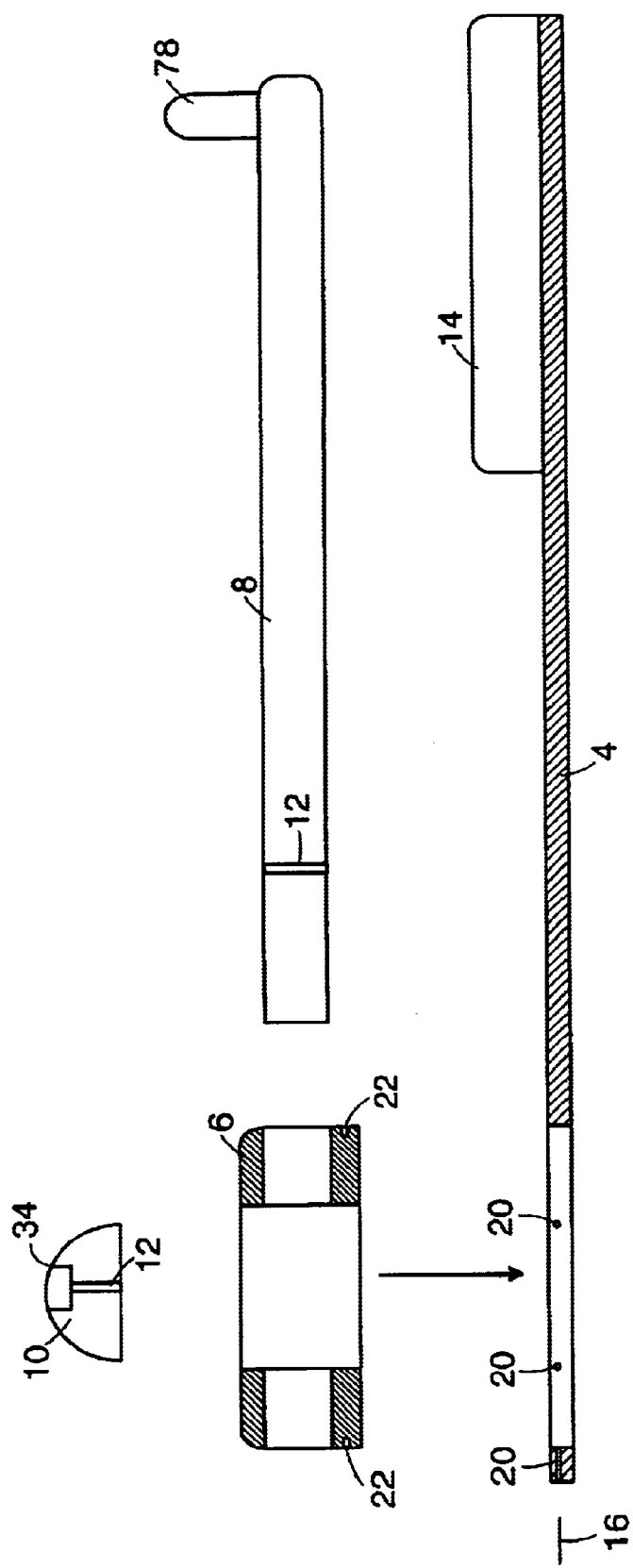
FIG. 2 depicts a schematic exploded side view of the device of FIG. 1.
Figure 3:
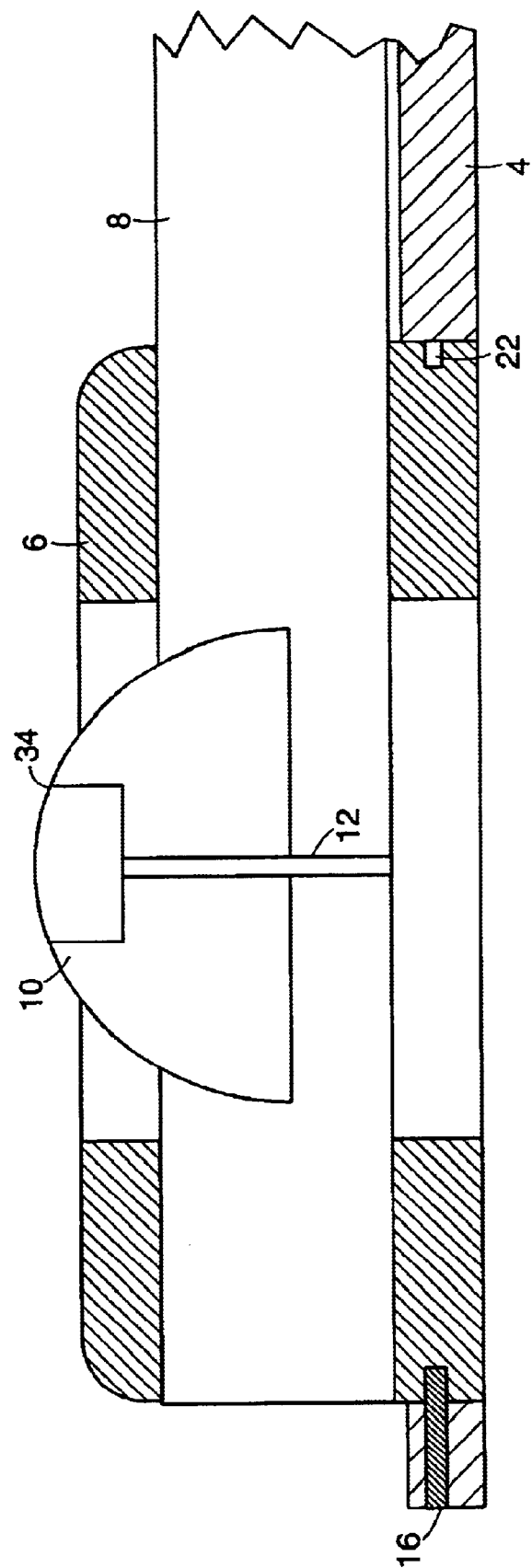
FIG. 3 depicts a schematic enlarged side view of the device of FIG. 1.

Devices and methods according to the present invention allow a medical professional to accurately and rapidly place a probe, such as a needle, in a patient. Some of these devices allow a medical professional to adjust the trajectory of an entry needle such that a target within the body is quickly located and the needle is rapidly inserted through a patient's tissue to the target area. For example, devices of the present invention allow medical professionals to gain easier, faster antegrade access during a percutaneous nephrolithotomy ("PCNL") procedure. While placement of the entry needle is described herein mainly as relating to a PCNL procedure, devices and methods according to the invention are useful in many medical procedures involving placement of a probe. For example, insertion of an entry needle into a patient's spinal column is just one example of other medical procedures that are applicable to the present invention.

Several techniques are currently used to perform PCNL procedures. Antegrade access to a kidney involves a medical professional inserting a needle through a patient's back and into his kidney. Typically, a medical professional will guide an entry needle to a target calyx within the kidney under the guidance of a fluoroscope or a similar device. Briefly, a fluoroscope is a device that is used with an x-ray emitting device in order to visualize body structures and/or medical instruments. The x-ray energy is either transmitted through material that is transparent to the energy or is modulated by radiopaque material. After the x-ray energy is either transmitted or modulated, the fluoroscope detects at least some of the energy. Radiopaque material appears as an image on a display of the fluoroscope, while other transparent materials that are not radiopaque do not appear on the display. For example, medical devices can be constructed of radiopaque and/or transparent material, depending upon whether or not they are to be visualized during a procedure. Additionally, radiopaque contrast dyes can be injected into a body structure or tissue, such as a target calyx in a kidney, so that the structure or tissue can be visualized on the screen of the fluoroscope display. The term "radiopaque" generally refers to a substance that at least partially prevents transmission (by blocking, reflecting, absorbing, defracting, and/or any similar phenomenon) of at least one type of electromagnetic radiation, such that an image of the substance will appear on a display. In the embodiments described herein, the most typical use of radiopaque materials is in conjunction with an x-ray emitting device and/or a fluoroscope. However, other energy emitting devices and/or visualization devices similar to a fluoroscope are suitable for use with apparatus and methods according to the invention. Additionally, although the embodiments described herein usually refer to radiopaque materials for use as an imaging sight, the embodiments can include imaging sights that can be used with devices other than an x-ray emitting device and/or a fluoroscope (such as an MRI device or a CAT-scan device). If the materials used for the imaging sight are changed from, for example, a metal to, for example, a fluid-filled or a gas-filled material with a known density, then such materials can be seen with the MRI device or CAT-scan device but may not be able to be seen with a fluoroscope.

One type of PCNL procedure typically is performed using a triangulation technique which utilizes a needle that is 18 to 21 gauge, an x-ray emitting device, and a fluoroscope. The medical professional first aligns the tip of the needle (on the patient's back) with the target calyx (visualized by injecting a radiopaque dye into the kidney) in a vertical position with the x-ray emitting portion of the x-ray device ("x-ray head") and the fluoroscope also in the vertical position, defining the needle's point of entry. ("Vertical" typically means an axis extending perpendicular from the point of entry. When the needle is in a vertical position, it can be aligned along this axis with the x-ray head and the fluoroscope at certain points of the procedure). The medical professional will then reposition the x-ray head and the fluoroscope to a 30 degree angle from the vertical position while keeping the needle in the vertical orientation (or at a slight angle from the vertical position). By using the x-ray head and the fluoroscope in the vertical and 30 degree positions and viewing the needle on a display associated with the fluoroscope, the medical professional will approximate the desired needle entry angle and trajectory to reach the target calyx as well as the needle's depth in the patient's tissue. The medical professional then pushes the needle through the entry point, towards the target calyx. As necessary, the medical professional moves the x-ray head and the fluoroscope between the two views and the needle trajectory can be adjusted to successfully achieve access into the head of the target calyx. Typically, multiple rounds of trajectory adjustment are necessary in order to achieve access, and this process is often time consuming. The medical professional uses tactile feedback and the two views to determine when the target calyx has been successfully reached by the tip of the needle. The final check to confirm access into the kidney is performed by the physician removing the needle (the needle typically is disposed within a trocar having a hub), attaching a syringe to the hub, and aspirating. If urine is aspirated, kidney access has been achieved. If access has not been achieved, the entry needle must be repositioned and syringe reattached for further aspiration. One difficulty with this procedure is performing three dimensional access using two dimensional views.

A second technique for performing a PCNL procedure is known as the "bullseye" technique. A patient is typically oriented on his/her side at an angle to an operating table such that a target calyx is generally aligned with the operating table (for example, the calyx is perpendicular to the table). A medical professional attempting kidney access with this technique will typically first align the tip of a guide needle on the patient's back with the target calyx (visualized by injecting a radiopaque dye into the kidney) using the x-ray head and the fluoroscope in vertical position, defining the needle's point of entry. The medical professional will then insert the guide needle, for example a 13 gauge needle, vertically through this entry point and about 2–3 cm into the patient's fatty tissue layers. This needle acts as the guide for an entry needle. A physician typically will clamp a pair of forceps around the 13 gauge needle and hold the forceps at their proximal end, allowing the physician to adjust the orientation of the 13 gauge needle while keeping his/her hands out of the fluoro field (i.e., the field of energy given off by the x-ray emitting device). When the medical professional has aligned the radiopaque hub of the 13 gauge needle with the target calyx, and with the x-ray head and the fluoroscope in vertical orientation, an 18 gauge entry needle is inserted through the 13 gauge needle, into and through the patient's tissue, and into the patient's kidney. A properly aligned guide needle, which can have a radiopaque outer wall, will appear in the screen display of the fluoroscope as a circle that circumscribes at least a portion of a target calyx with an entry needle, which also can be radiopaque, in the center of the circle. The medical professional typically uses tactile feedback to determine if access into the kidney is achieved. The medical professional typically confirms that access into the kidney is achieved by removing an inner portion of the entry needle, attaching a syringe, and aspirating for urine through the space left by the removed portion of the entry needle. The presence of urine confirms access into the kidney. Many variations on this technique are possible. This technique also may require multiple attempts at positioning the entry needle and connecting and disconnecting a syringe for access confirmation, and this technique, too, is a time consuming process.

The present invention saves procedure time and improves targeting accuracy by giving the medical professional a tool to better control and align the movement of the entry needle through the back and into the target calyx of the kidney. In certain embodiments, a medical professional can use devices according to the invention while keeping his or her hands away from the energy given off by an x-ray (or other energy) emitting device, and/or the medical professional can maintain the ability to have tactile feedback during insertion of the entry needle. Additionally, in certain embodiments, the medical professional can lock the needle guiding apparatus (or components thereof) into alignment with the target calyx, and/or can stabilize the apparatus by attachment to a fixed object (such as an operating table). A medical professional also can have the ability to remove his/her hands from certain embodiments according to the invention without movement of the entry needle trajectory. Also, the entry needle to be inserted through certain embodiments of the invention can travel through about 60 degrees of rotation in all planes from vertical (and more than about 60 degrees or less than about 60 degrees in certain embodiments) and/or can be inserted completely into target calyx. Devices according to the invention can accommodate, for example, but without limitation, 18 to 21 gauge entry needles, and can have the ability for the handle design to prevent interference with the surface of the skin (e.g., winged handles).

Referring to FIGS. 1–7, one needle guiding apparatus 2 according to the invention includes a base 4, a turret 6, and an adjustment rod 8. At one end of the base 4, a ring 24 is formed from the base 4 or attached to the base 4. At the other end of the base 4, a handle 14 is applied to or formed from the base 4. The turret 6 has a groove 22 along one edge and is mounted inside of and rides within the ring 24. Pins 16 protrude through the ring 24 at holes 20 through the ring 24 and into the groove 22. These pins 16 secure the turret 6 within the base 4. Alternatively, the turret 6 can fit within the ring 24 with a friction fit.

The adjustment rod 8 is inserted through the turret 6 such that the adjustment rod 8 contacts the turret 6 and is held within the turret 6, but is still free to rotate. For example, a groove can be cut into the surface of and around the entirety of the adjustment rod 8. In this instance, the adjustment rod 8 is held in place by one or more pins inserted through one or both of the top and the bottom of the turret 6 (similar to how the turret 6 is held in the ring 24). Alternatively, the adjustment rod 8 can be held within the turret 6 with a friction fit. Atop the adjustment rod 8, a dome 10 having a radiopaque sight 34 is affixed to or is a unitary member of the adjustment rod 8. The sight 34 can be formed from the dome 10 if it is itself radiopaque, either partially or totally, or the dome can have radiopaque markings applied to it. For example, the radiopaque sight 34 on the dome 10 can be circular (such as a "donut" or a ring) to facilitate location of a target calyx 902 in a manner similar to the bullseye technique. Alternatively or in addition, the sight can be a diamond shape, in the shape of a cross-hair, in the shape of a perpendicular cross-hair, or any combination, such that device alignment is facilitated. A guide shaft 12 extends through the dome 10 and the adjustment rod 8. When the needle guiding apparatus 2 is properly aligned, described more fully below, this guide shaft 12 is aligned with the target calyx 902 and allows a medical professional to insert an entry needle 18 through the guide shaft 12 that provides a straight path into a patient as described more fully below. The guide shaft 12 can be relatively longer than the one shown and/or can include an extension. Typically, transparent components of the needle guiding apparatus 2 are manufactured from a plastic through an injection-molding process. However, the adjustment rod 8 can be radiopaque and, in that case, can be constructed from a metal such as stainless steel. Also, the sight, if radiopaque, is made from a radiopaque material such as a metal or a metalized coating.

Figure 4:
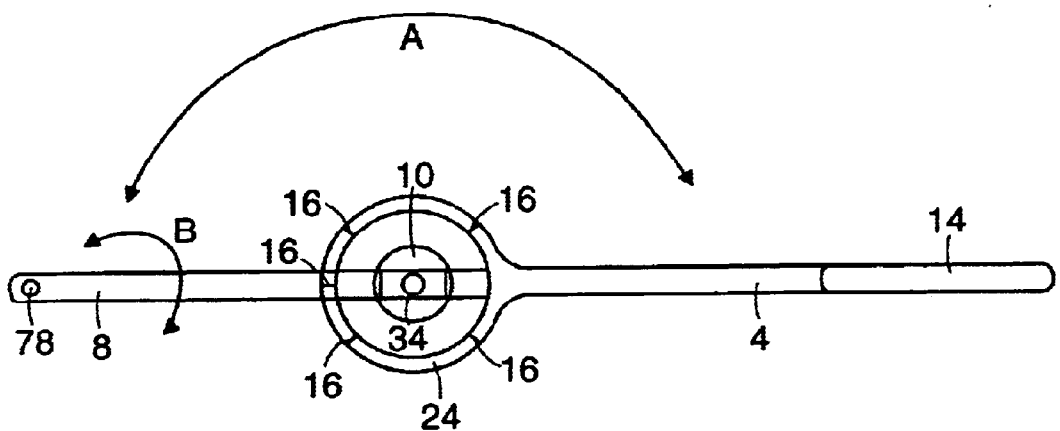
FIG. 4 depicts a schematic top view of the device of FIG. 1.
Figure 5:
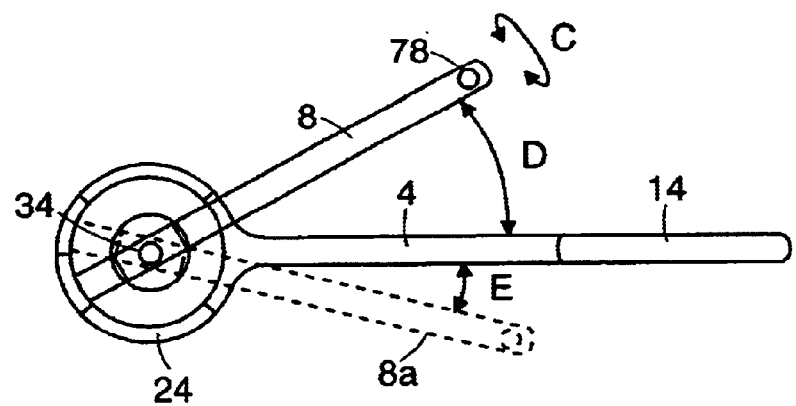
FIG. 5 depicts a schematic top view of the device of FIG. 1.

The turret 6 rotates 360 degrees about its axis, best shown in FIGS. 4 and 5. For example, in FIG. 4, the turret 6 is shown rotated 180 degrees from the handle 14, as indicated by arrow A. In addition to rotating in a counter-clockwise direction, as shown by arrows A and D in both FIGS. 4 and 5, the turret 6 can rotate in a clockwise direction as shown by arrow E between an outline of the adjustment rod 8a and the base 4. Additionally, the adjustment arm 8 itself rotates about its own axis, as shown by arrows B and C. The adjustment arm 8 can rotate in both a clockwise and a counter-clockwise direction about its own axis (arrows B and C). In this embodiment, a medical professional can use two hands. One hand steadies the device 2 at the handle 14, for example, while the other hand adjusts the alignment rod 8 along directions of travel A, B, C, D and/or E.

Figure 6B:
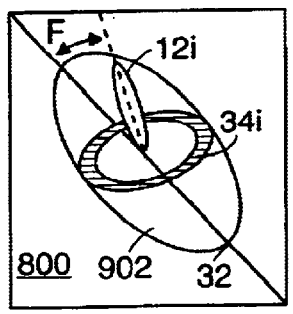
FIG. 6B depicts a schematic display screen view of an unaligned device of FIG. 1.
Figure 6C:
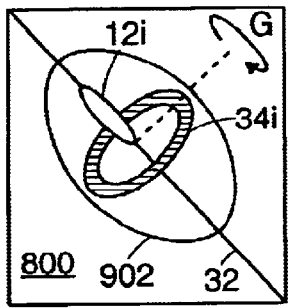
FIG. 6C depicts a schematic display screen view of a partially unaligned device of FIG. 1.
Figure 6D:
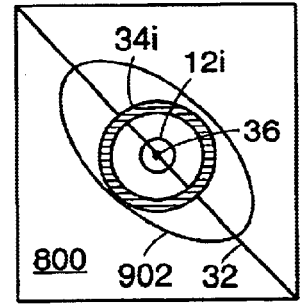
FIG. 6D depicts a schematic display screen view of a properly aligned device of FIG. 1.
Figure 6A:
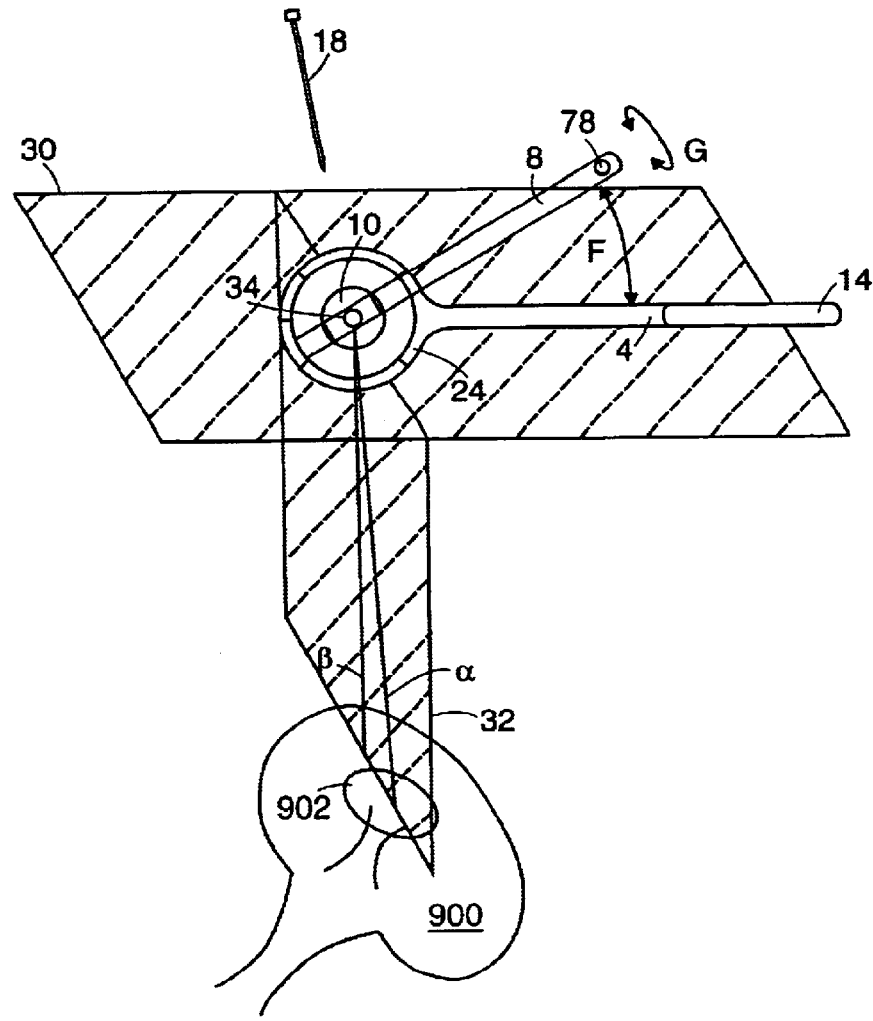
FIG. 6A depicts a schematic top view of the device of FIG. 1 in relation to a patient's skin and a target.
Figure 7:
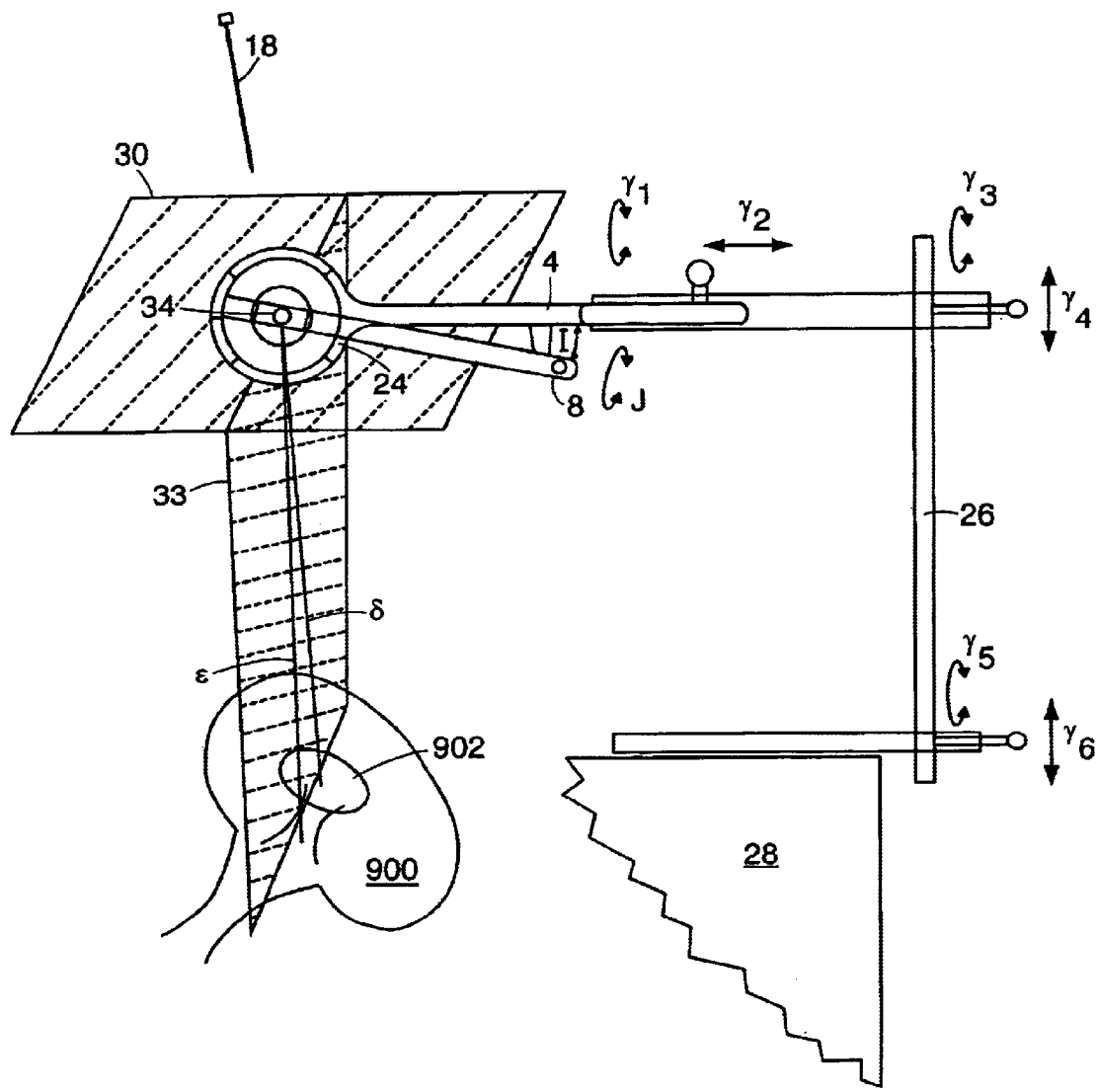
FIG. 7 depicts a schematic top view of the device of FIG. 1 in relation to a patient's skin and a target, the device attached to a fixed surface.

In operation, the apparatus 2 typically lies in the plane 30 of a patient's skin, shown in highly schematic fashion in FIGS. 6A and 7. A plane drawn through the ring 24 is parallel to the plane of the skin 30. Additionally, the base 4 typically either touches a patient's skin or is just adjacent to the skin. No needle is necessary to hold the device onto a patient's skin (although one could be used in this embodiment or any embodiment). The device 2 is operable with a single hand, especially when moving the adjustment rod 8 short distances from being aligned with the base 4 and handle 14. The medical professional typically presses the device 2 onto the top surface of the patient's skin while holding the handle 14 and controls the alignment rod 8 with his thumb. Pushing the tip of a rotation knob 78 will rotate the alignment rod 8 in the direction of arrow G. Pushing near the base of the rotation knob 78 will rotate the alignment rod 8 about the center of the ring 24 (arrow F). For larger movements, the alignment rod 8 can be adjusted with the medical professional's other hand.

In one method, the medical professional identifies the entry site and a needle plane 32 on the patient's back by laying the bottom of the base 4 flat (or nearly flat) against the skin layer and aligning the radiopaque sight 34 on the dome 10 with the target calyx 902 using an x-ray emitting device and a fluoroscope. The needle plane 32 in this case is along the long axis of the target calyx 902. Typically, a medical professional chooses this axis for easy visual reference on the fluoroscope screen, but any axis through a calyx can be chosen to define the needle plane. Rotation (arrow F) of the turret 2 and alignment rod 8 about the center of the ring 24 aligns the needle plane 32 through which the entry needle 18 passes. Rotation (arrow G) of the alignment rod 8 about its own axis, controls the trajectory of the guide shaft 12 and the entry needle 18, which is inserted through the guide shaft 12 and into a patient. This trajectory occurs within the needle plane 32. Briefly, the medical professional checks the intended entry trajectory or plane alignment and adjusts the apparatus 2 by matching the angle of the x-ray head and the fluoroscope to the angle of the optionally radiopaque guide shaft 12, the radiopaque sight 34 on the dome 10, and the target calyx 902. Once correct alignment is confirmed on the fluoroscope display screen, the medical professional can lock the alignment rod 8 into position. For example, a screw can lock the alignment rod 8 into place. The entry needle 18 is positioned into the guide shaft 12 and advanced towards the target calyx 902. The medical professional can use the fluoroscope to confirm the advancement of entry needle 18 into the target calyx 902.

When properly aligned, the apparatus 2 is adjusted to a position such that the entry needle follows a particular trajectory a in the plane 32, leading to the target calyx 902 of the kidney 900. One improperly aligned setting of the apparatus 2 is shown with the entry needle trajectory along a trajectory $\beta$ in the same plane 32 as the proper trajectory $\alpha$. The improper trajectory $\beta$, while in the same plane as the proper trajectory a, is not aligned with the target calyx 902. This improper alignment can be corrected by rotating the adjustment rod 8 clockwise (direction of travel G) to achieve the proper trajectory $\alpha$.

These properly and improperly aligned states are shown as screen displays on, for example, a screen display 800 of a fluoroscope, in FIGS. 6B and 6C, respectively. In FIG. 6B, the image 34i of the imaging sight 34 appears atop the target calyx 902 in the screen display 800 of the fluoroscope. The image 12i of the guide shaft 12 is not in alignment with the needle plane 32. The guide shaft is moved in direction F as the turret 2 is moved in direction F. Rotation in direction F brings the image 12i of the guide shaft 12 into alignment with the needle plane 32 (FIG. 2C). Although the guide shaft 12 is in the needle plane 32 at this point, the guide shaft 12 is aligned along the improper trajectory $\beta$. In fact, in one of many incorrect orientations, the guide shaft 12 is not aligned with the center of the sight 34, such that the image 12i of the guide shaft 12 appears outside the image 34i of the sight 34, unaligned with the center of the target calyx 902. Additionally, the image 34i of the sight 34 appears non-circular (e.g., elliptical) because the sight 34 is not completely perpendicular to the proper trajectory axis $\alpha$, and, hence, the guide shaft 12 (about which the sight 34 is disposed) also appears non-circular and is not aligned with the target calyx 902. When this improperly aligned image appears, the device 2 is further aligned by moving the adjustment rod 8 in direction G until the screen display image looks like the one shown in FIG. 6D. In FIG. 6D, the entry needle 18 (located at least partially within the guide shaft 12) along a properly aligned trajectory a appears as a needle tip 36 in the screen display 800. If shown in an enlarged image, the needle tip 36 can appear circular. This tip 36 is surrounded by a circular image 12i of the guide shaft 12 and a circular image 34i of the sight 34 above the target calyx 902. The image 34i of the sight 34 and the image 12i of the guide shaft 12 appears circular with the tip 36 in their center when the x-ray head and the fluoroscope are held along the same axis $\alpha$ as the entry needle 18 (and guide shaft 12) and when the sight 34 of the dome 10 is in a plane that is perpendicular to the axis $\alpha$. Hence, the guide shaft 12 (about which the sight 34 is disposed and through with the entry needle is inserted) is aligned with the target calyx 902. This easy adjustment of an improperly aligned device can save procedure time and can increase accuracy in targeting the target calyx.

Now referring to FIG. 7, a second example of proper $\delta$ and improper $\epsilon$ device alignment is shown. However, these trajectories $\delta$, $\epsilon$ are attained with the adjustment rod 8 in a different position than in FIG. 6A. The plane 33 in which the needle trajectories $\delta$, $\epsilon$ fall in FIG. 7 is rotated from the plane 32 in which the needle trajectories $\alpha$, $\beta$ fall by the same amount that the adjustment rod 8 is rotated from its position in FIG. 6A to its position in FIG. 7. Adjustment of the needle trajectories $\delta$, $\epsilon$ and the needle plane 33 is accomplished by moving the adjustment rod 8 along directions of movement I and J, as described for directions of movement F and G, respectively, in FIG. 6A above. A screen display while adjusting an improperly aligned device to a properly aligned device changes and appears similar to those shown in FIGS. 6B, 6C and 6D.

Additionally, the apparatus 2 is attached to a stand 26 with various adjustments possible $\gamma_1$, $\gamma_2$, $\gamma_3$, $\gamma_4$, $\gamma_5$, and $\gamma_6$. The stand 26 is attached to a fixed surface 28, such as an operating table. This attachment may be advantageous for stabilizing the device 2 because, in some instances, the surface of the skin can move. Also, the medical professional can remove his hands from the device 2 without disturbing a desired needle trajectory. The stand 26 could be secured such that the device 2 rests on the surface of the skin or slightly above.

Figure 8:
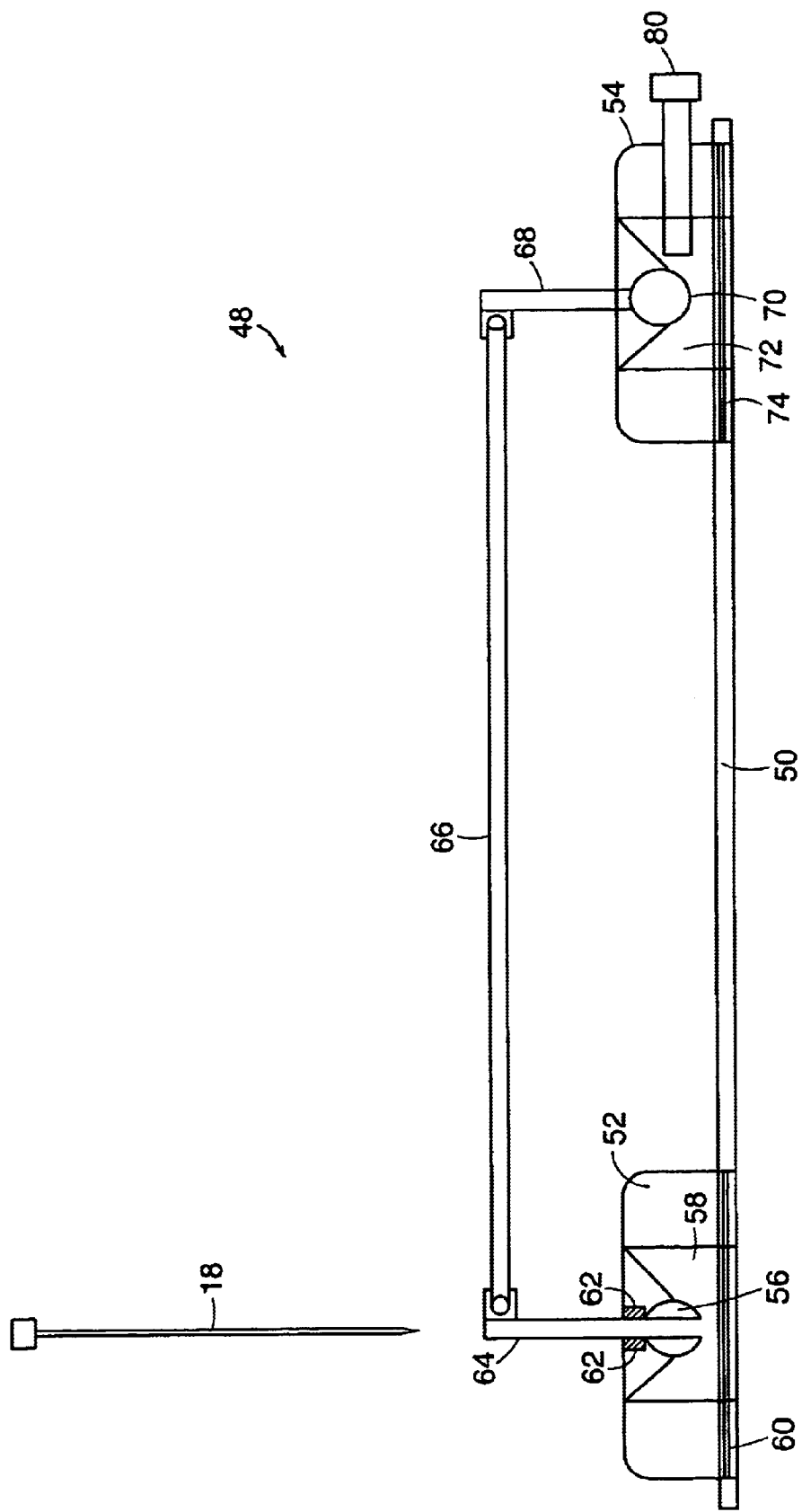
FIG. 8 depicts a schematic side view of a device including a ball and socket joint and a movement duplicating mechanism, according to the invention.

Now referring to FIG. 8, another embodiment of a needle guiding apparatus 48 is depicted. The apparatus 48 has a base 50. The base 50 has one opening at either end. One opening contains a guide component 52 and the other opening contains a base component 54. Each of the guide component 52 and the base component 54 have a groove (60, 74 respectively) that holds each assembly in the base in the manner described for the turret of the apparatus in FIGS. 1–7. Alternatively, each component 52, 54 can be held in the base 50 by a friction fit, can be bonded to the base 50, and/or can be the same piece of material as the base 50.

The guide component 52 contains a socket 58. A ball 56 fits within the socket 58, and a guide shaft 64 extends from the ball 56. A radiopaque sight 62 surrounds the guide shaft 64 on top of the ball 56. The guide shaft 64 has a passageway extending through it and in alignment with a passageway through the ball. The entry needle 18 can be inserted through these passageways. With the guide shaft 64 in place, the ball 56 articulates in the socket 58 in all directions, the range of motion limited only by the guide shaft 64 coming into contact with the upper edge of the guide component 52 and/or the socket 58. A control arm 66 is connected with the guide shaft 64 at a joint. At the other end of the control arm 66, an extension 68 is connected to the control arm 66 at a second joint. The extension 68 is attached to a ball 70 that articulates in a socket 72 and is contained within the base component 54 in a similar fashion to the ball 56 and socket 58 located within the guide component 52. When a medical professional moves, for example, the extension 68, the movement is replicated at the guide shaft 63 which ultimately also duplicates the rotational angle of the extension 68. The medical professional adjusts the plane in which the entry needle 18 travels and the trajectory along which the entry needle 18 travels with a single movement of the extension 68 (i.e., control is not separated into two process as described above in the embodiment of FIGS. 1–7). A lock 80 can be used to prevent the ball 70 and extension 68 from moving in order to lock the guide shaft 64 into its intended trajectory. The lock 80 can be, for example, a screw.

Figure 9:
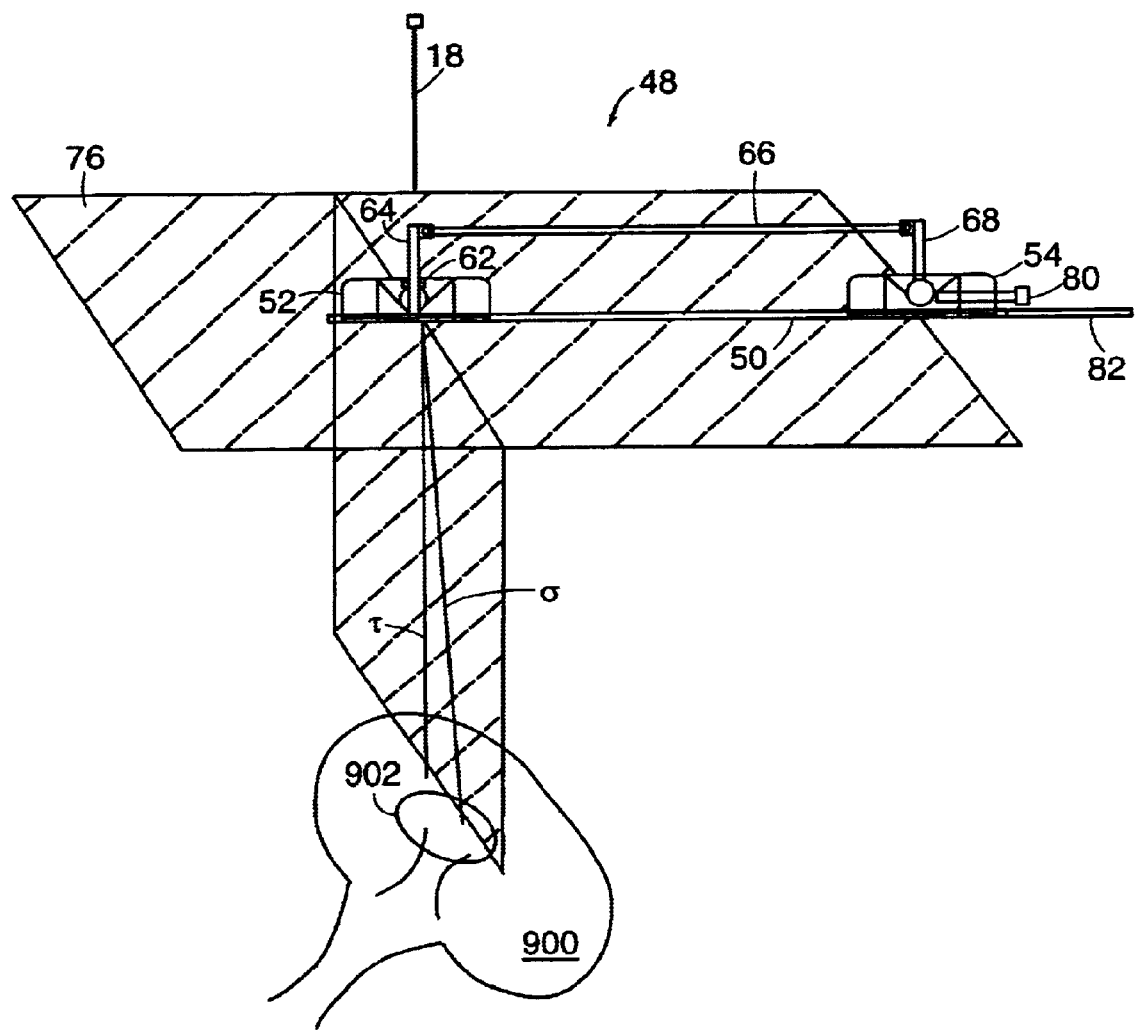
FIG. 9 depicts a schematic side view of the device of FIG. 8 in relation to a patient's skin and a target.

Now referring to FIG. 9, the apparatus 48 is placed on, or in close proximity to, a patient's skin, represented by a plane 76. Thus, the apparatus 48 lies flat (or nearly flat) against the patient's skin. The apparatus 48 can include a handle 82 or be attached to a stand, as described above. A medical professional manipulates the extension 68 (or similar structures such as a "joy stick") and the movement is translated, through the control arm 66, to the guide shaft 64 and ball 56. Positioning the passage through the guide shaft 64 and ball 56 properly allows the entry needle 18 to be properly positioned within a patient. When properly positioned, the apparatus 48 guides an entry needle 18 along a proper trajectory σ to reach the target calyx 902. If not properly positioned, the apparatus 48 will guide an entry needle 18 along in improper trajectory τ, and the entry needle 18 will not reach the targeted area. The apparatus 48 has a sight 62 located coaxially with and disposed about the guide shaft 64. The medical professional adjusts the needle guiding apparatus using a fluoroscope display screen in a manner similar to that described for FIGS. 6B, 6C, and 6D above, where the proper trajectories α, σ shown in FIGS. 6A and 9 correspond with each other and the improper trajectories β, τ shown in FIGS. 6A and 9 correspond with each other. This embodiment also can increase the accuracy with which the entry needle is placed and can decrease procedure time by allowing more rapid placement and access to the target calyx.

Figure 10:
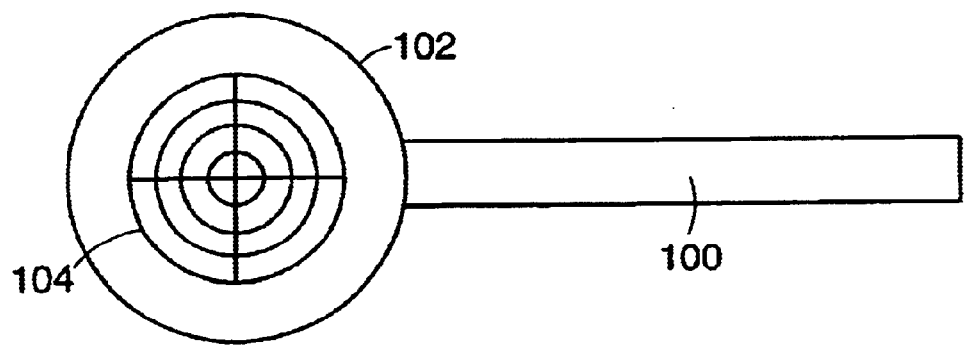
FIG. 10 depicts a schematic top view of a domed device, according to the invention.
Figure 11:
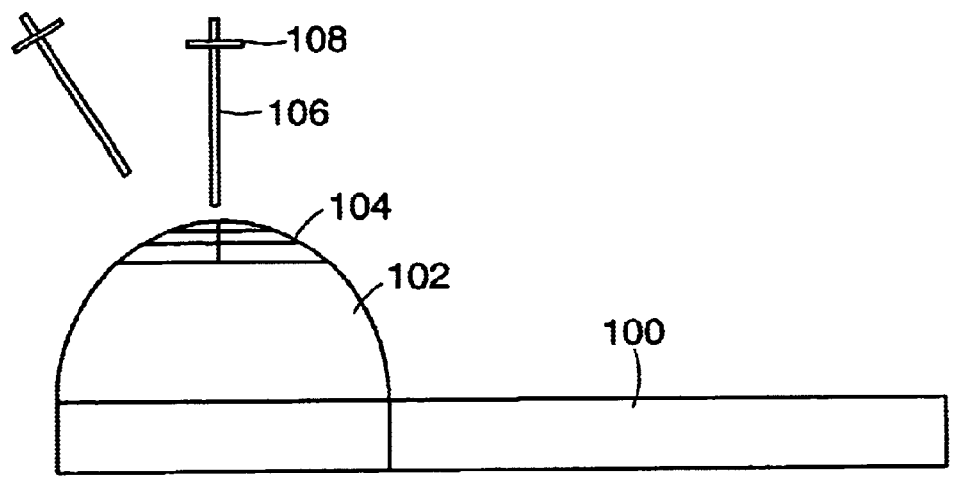
FIG. 11 depicts a schematic side view of the embodiment of FIG. 10.

In another embodiment of the invention, and referring to FIGS. 10 and 11, a dome 102 is disposed within or attached to a base 100. A radiopaque sight 104 is applied to or is integral with the dome 102. In operation, a medical professional inserts a guide needle 106 into the dome 102 under the guidance of a fluoroscope. The guide needle 106 is hollow and includes a guide needle stop 108 that, in conjunction with the dome's 102 shape, prevents the guide needle 106 from penetrating a patient's skin surface prior to alignment of the device. The medical professional checks the intended entry trajectory and/or alignment of the guide shaft 106 for the entry needle by approximately matching the angle of the x-ray head and the fluoroscope to the angle of the optionally radiopaque guide needle 106, radiopaque sight 104 and the target calyx and viewing the fluoroscope display, as described above. An entry needle can be inserted through the properly aligned guide needle 106.

In another embodiment, and referring to FIGS. 12, 13, and 14, a needle guiding apparatus 132 includes a turret 122 that rotates within a ring 130 of a base 120. The turret 122 includes guide shafts 124, 126, 128 (not all guide shafts are labeled). Radiopaque material can align with the walls defining the guide shafts 124, 126, 128 such that the material forms a ring, and/or at least a portion of the walls of the guide shafts 124, 126, 128 can be constructed from a radiopaque material. A medical professional can rotate the turret 122 by grasping the protrusion containing guide shafts 124, 126, 128 and twisting the turret 122 (arrow K) in either a clockwise or counter-clockwise direction. Each guide shaft 124, 126, 128 extends through the turret 122 and is disposed at a different angle relative to the base 120. For example, two guide shafts 124, 126 that are adjacent to each other have different angles relative to the base (φ, χ, respectively, as shown in FIG. 14). Thus, rotating the turret 122 can change the plane in which an entry needle will travel, but the needle trajectory is determined by the angle of the particular guide shaft. In use, the medical professional substantially matches the angle of the x-ray head and the fluoroscope with the angle of the guide shaft being used, such that a screen display shows the calyx circumscribed within a circular image of the radiopaque material when the device is properly aligned.

Figure 31:
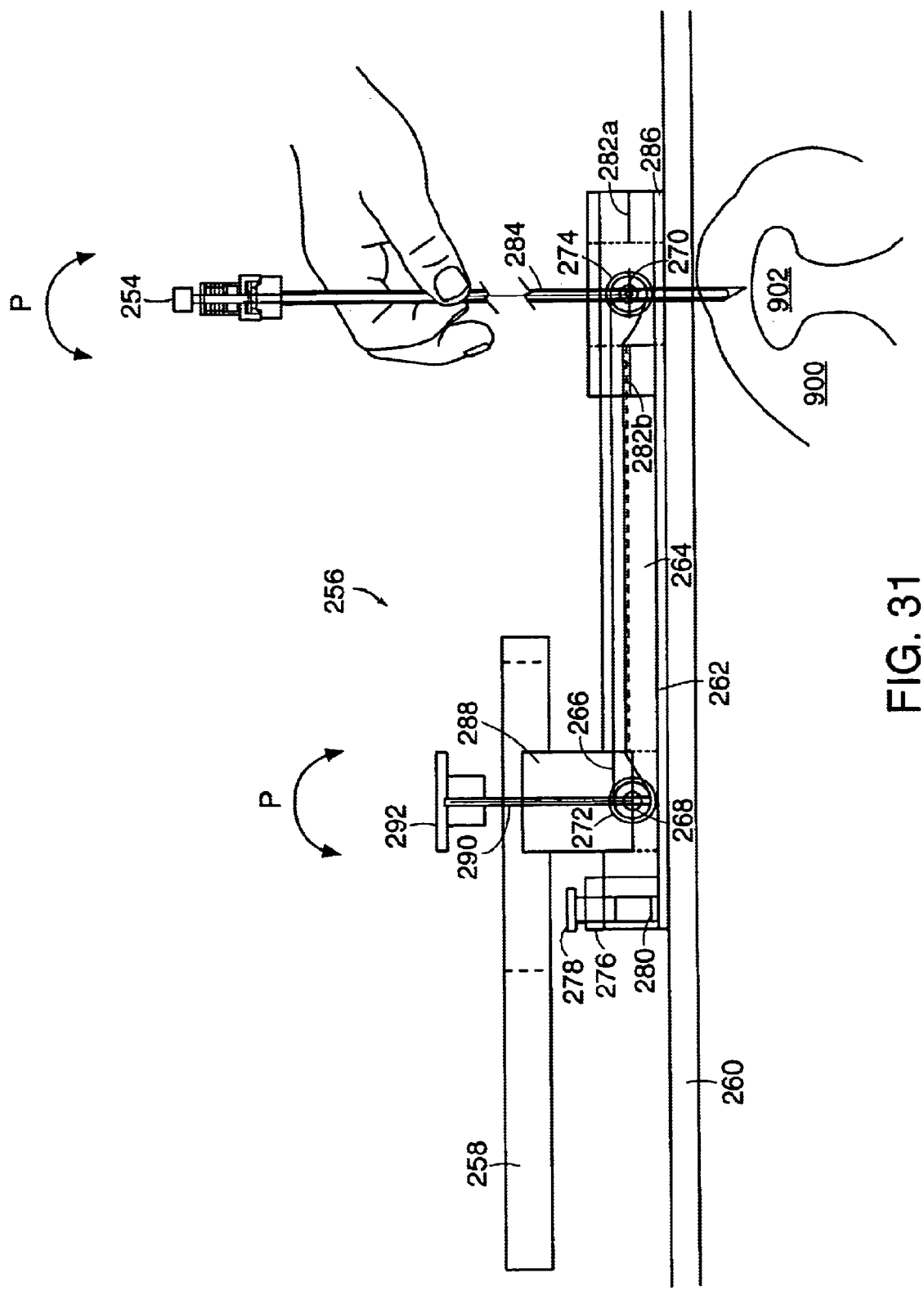
FIG. 31 depicts a schematic side view of one embodiment of a needle guide apparatus and an embodiment of an entry needle in use.

Now referring to FIGS. 31–33, another embodiment of the invention, shows a needle guiding apparatus 256 capable of directions of movement P and R. A handle 258 is connected with an adjustment rod 264 through a connector 288. Within the adjustment rod 264, a pulley 272, optionally with a gear, is connected to an axial 268 extending through the pulley 272 so that the pulley 272 can rotate about the axial 268. A control shaft 290 runs through the handle 258 and axial 268, and a control nut 292 is threaded onto the control shaft 290 so that the control nut 292 can be tightened against the handle 258 to hold the control shaft 290 in a particular position. A base 262 runs along the bottom of the device 256 and at one end, opposite the handle 258, opens into a ring 286. The ring 286 can have bars of radiopaque material 282a, 282b, 296a, 296b disposed on or within it. The sections of radiopaque material can be situated such that the material 282a, 282b, 296a, 296b forms cross-hairs (for example, they are perpendicular) and can be aligned in the same horizontal plane as an axis extending through the center of the adjustment rod 264. Alternatively, radiopaque material can be located in the core of the adjustment rod 264. For ease of description, the sections (or bars) of radiopaque material 282a, 282b that are aligned with the axis of the adjustment rod 264 will be referred to as a first band of radiopaque material, and the sections (or bars) of radiopaque material 296a, 296b that are perpendicular to the first band will be referred to as a second band of radiopaque material. A radiopaque marker shape 275 is located on the ring 286 and aids a medical professional in orienting the needle guiding apparatus 256 with the patient's body under fluoroscopic guidance by providing a point of reference.

Inside the ring 286, a second pulley 274, optionally connected with a gear, is connected to a second axial 270 that extends through the pulley 274 so that the pulley 274 can rotate about the axial 270. The second axial 270 rotates about the axis formed by the second band of radiopaque material 296a, 296b and about the axis formed by the axis extending through the adjustment rod 264 and the first band of radiopaque material 282a, 282b. An optionally radiopaque guide shaft 284 runs through the second axial 270, and the guide shaft 284 defines a passage extending through it. The guide shaft 284 is perpendicular to the axis through the second axial 270 (the axis that is aligned with the second band of radiopaque material 296a, 296b). An entry needle 254 can be inserted through the guide shaft 284, out the opening in the base 262 created by the ring 286, into a patient's skin 260, and into a target calyx 902 in the patient's kidney 900. A belt 266 located within the alignment rod 264 connects the first pulley 272 and the second pulley 274. This belt 266 transfers angular movement about the axials 268, 270 such that movement at one axial is transferred to the other axial. This movement is indicated as direction of movement P. The control shaft 290 can be used to move the axials 268, 270, pulleys 272, 274, and belt 266 so that the guide shaft 284 moves. The movement of the control shaft 290 can be replicated at the guide shaft 284 in a 1:1 ratio, or the movement can be transferred such that a small movement at the control shaft 290 produces a large movement at the guide shaft 284, or the movement can be transferred such that a large movement at the control shaft 290 produces a small movement at the guide shaft 284. The control nut 292 can be fastened when the medical professional has selected a desired position of the guide shaft 284 along direction of movement P. Other components can be used to transfer angular momentum from a control shaft to a guide shaft. For example, a pulley can include a groove or teeth so that the belt can ride in the groove or that grooves or teeth on the belt can enmesh with the teeth on the pulley. Alternatively, a series of gears can be used to transfer movement along the device, without a belt. Also, gears can be used with the belt and pulley system so that greater than or less than a 1:1 ratio of movement at the control shaft and guide shaft is produced, allowing for fine gradations of movement at the guide shaft. Also, linkage arms can be used to connect and transfer movement between the control shaft and the guide shaft.

The device 256 includes components that are moveable about an axis that is perpendicular to the axis about which movement P is generated. The handle 258 is connected to the adjustment rod 264 through the connector 288 such that as the handle 258 is moves, it moves in an arc that has its center aligned with the axis of the adjustment rod 264. Thus, moving the handle 258, in turn, rotates the adjustment rod 264. Moving the handle 258 and adjustment rod 264 moves the guide shaft in direction R and, also, moves the control shaft in direction R. The transmission elements, including the axials 268, 270, pulleys 272, 274, and belt 266, are housed within the adjustment rod 264 and rotate with the adjustment rod 264 along its axis. This direction of movement R is perpendicular to direction of movement P. A lock 276 has a screw 278 that tightens onto the adjustment rod 264 that fits within a groove 280, to prevent the adjustment rod 264 from moving and, thus, prevent the guide shaft 284 from moving.

Directions of movement P and R typically are indicated as an arrow with two heads in the drawings, because, typically movement can occur in a "positive" or "negative" direction. For example, direction of movement P can have a positive and negative direction. Thus, in relation to direction of movement P, positive movement is in the opposite direction from negative movement but occurs along the same line or same arc of rotation (direction P) as the negative movement. However, in some instances, as described throughout the specification, while "positive" or "negative" movement in a given direction (such as +P, –P or +R, –R) is indicated in the Figures and is possible, movement in only the positive or negative direction may be appropriate. This explanation applies to the other directions of movement described in the other embodiments according to the invention (for example, A, B, C, D, E, F, G, H, I, J, K, L, Q, S, and T can have positive or negative directions of movement). The terms "positive" and "negative" are arbitrary and are meant merely to convey the concept of opposite directions of movement.

In a variation on this embodiment, an embodiment shown in FIGS. 46 and 47 is a device 298 has essentially the same components as the embodiment of FIGS. 31–33 and moves in both the P and R directions in a similar manner. However, the device 298 that has the direction of movement R controlled in a slightly different manner. Rather than the handle 258 rotating with the adjustment rod 264, the control shaft 290, housed in a control shaft housing 300, also can be moved in direction R to control the rotation of the adjustment rod 264 in direction R, transferring movement in the R direction to the guide shaft 284. Either one or both of the control shaft 290 and control shaft housing 300 can move in direction R. The same movement of the adjustment rod 264 in direction R is generated as would be generated with the handle 258 in the embodiment shown in FIGS. 31–33. This movement of the control shaft 290 in both the R and P directions simultaneously moves the guide shaft 284 in the same directions (R and P). Only one control lever is needed to control movement of the guide shaft 284 in both directions (R and P). Movement of the guide shaft 284 in the P direction in this alternative embodiment is controlled similarly to the embodiment in FIGS. 31–33. The embodiments shown in FIGS. 31–33 and 46–47 can either have a sharp object (not shown) that inserts into a patient's skin to facilitate holding the device along the patient's skin or it can lack such a sharp object with the device held in place by the medical professional and/or an attachment that stabilizes the device in association with a object that is fixed in position, such as an operating table.

Now referring to FIGS. 34–41B, operation of the needle guide apparatus 256 of FIGS. 31–33 is described stepwise as a medical professional might perform a procedure on a patient 1000 with the device 256. FIGS. 34–41B are oriented such that the patient 1000 is laying on the patient's right side, facing the medical professional, so that the patient's 1000 left kidney 900 is positioned above the patient's right kidney (not shown). The patient would face away from the physician, with the right kidney positioned over the left kidney, if the right kidney is to be accessed. Also, in some instances, a kidney is accessed with the patient laying on his/her stomach. This procedure is described for a right-handed medical professional such that the medical professional holds the apparatus 256 in his/her left hand and inserts an entry needle (not shown) through the guide shaft 284 with his/her right hand. One can easily discern a procedure for a left-handed medical professional who would hold the apparatus in the right hand and the entry needle in the left hand.

Figure 34:
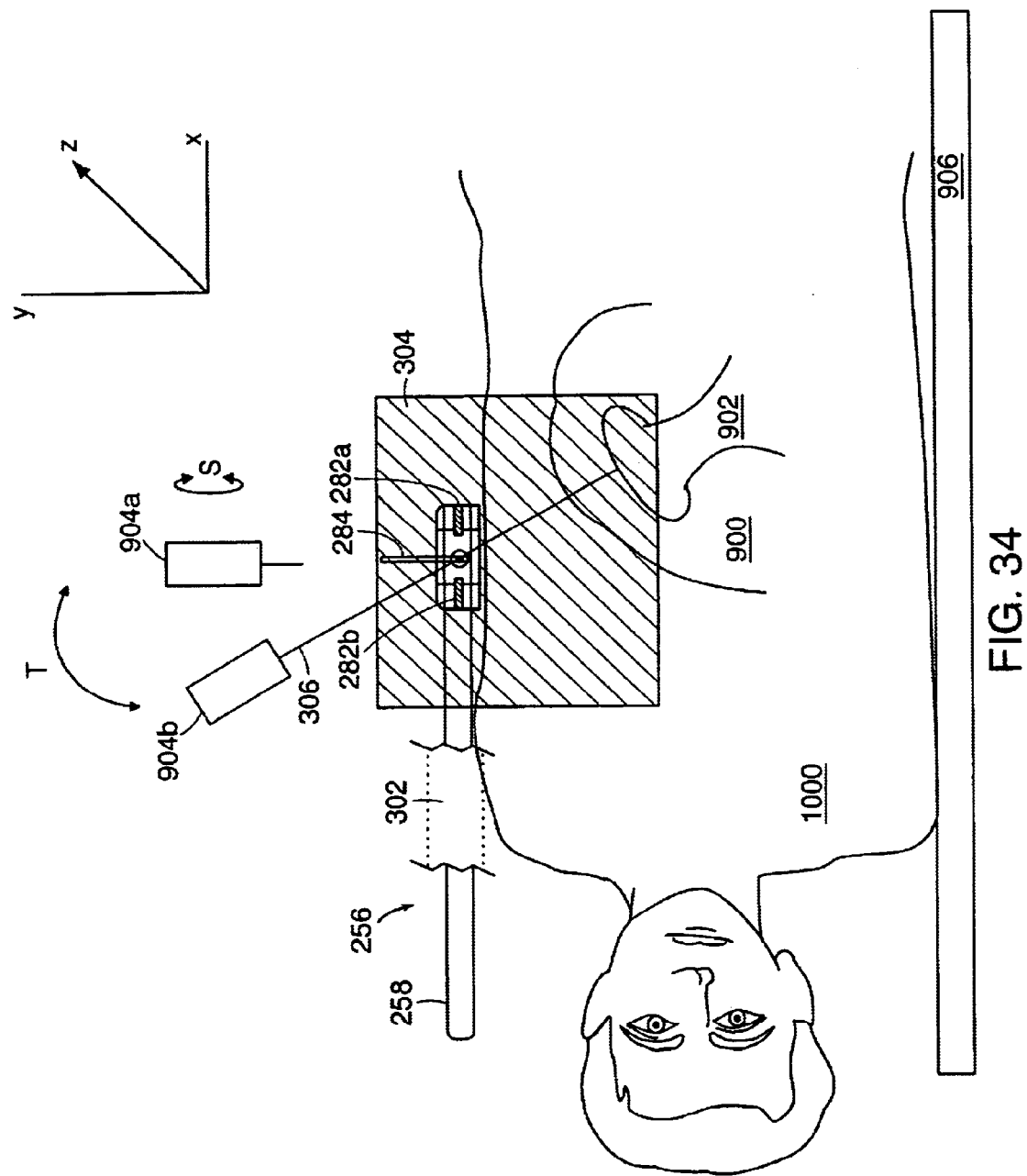
FIG. 34 depicts a schematic side view of the embodiment of FIG. 31 in use.
Figure 35:
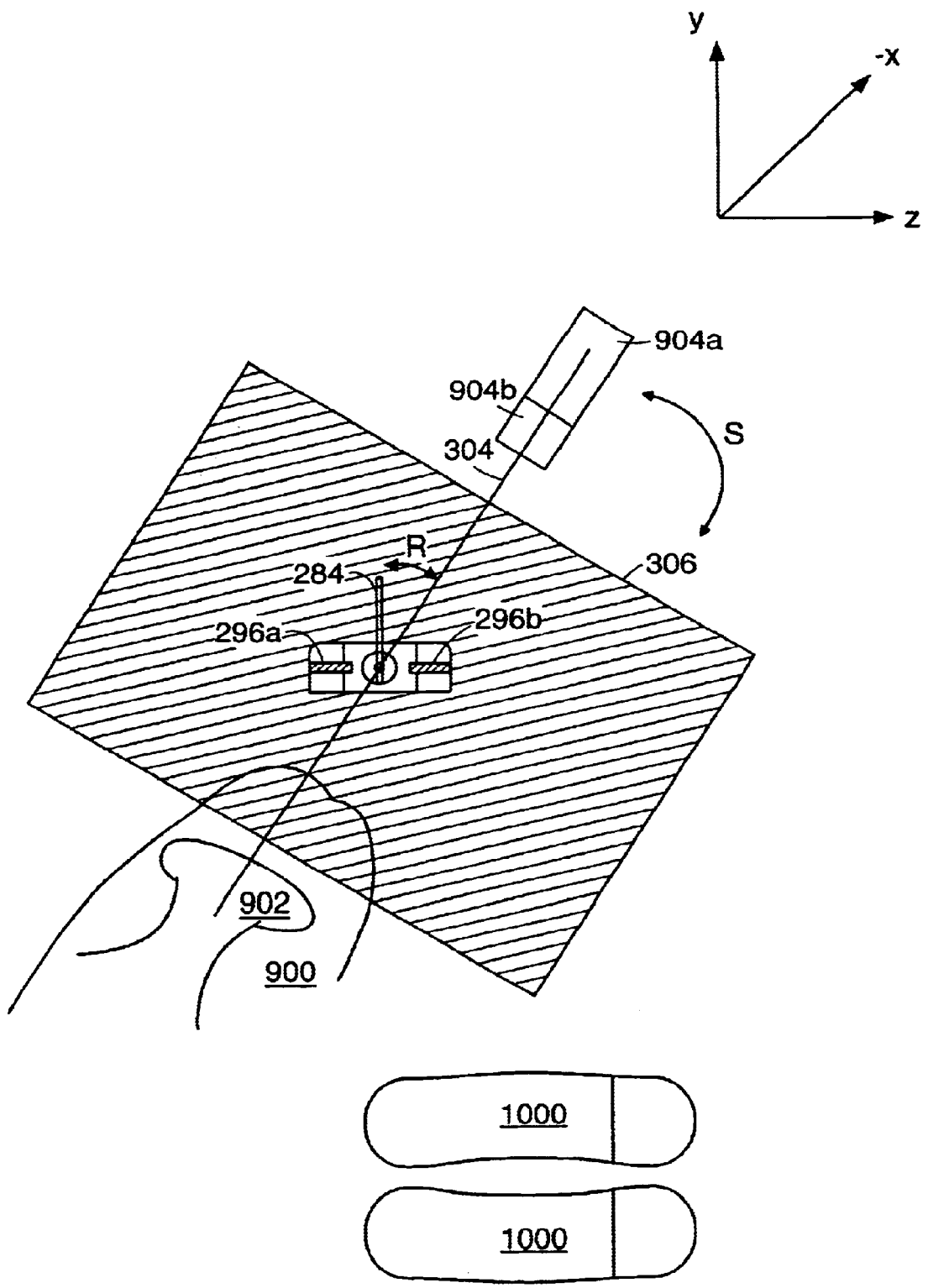
FIG. 35 depicts a schematic end view of the embodiment of FIG. 31 in use.
Figure 36:
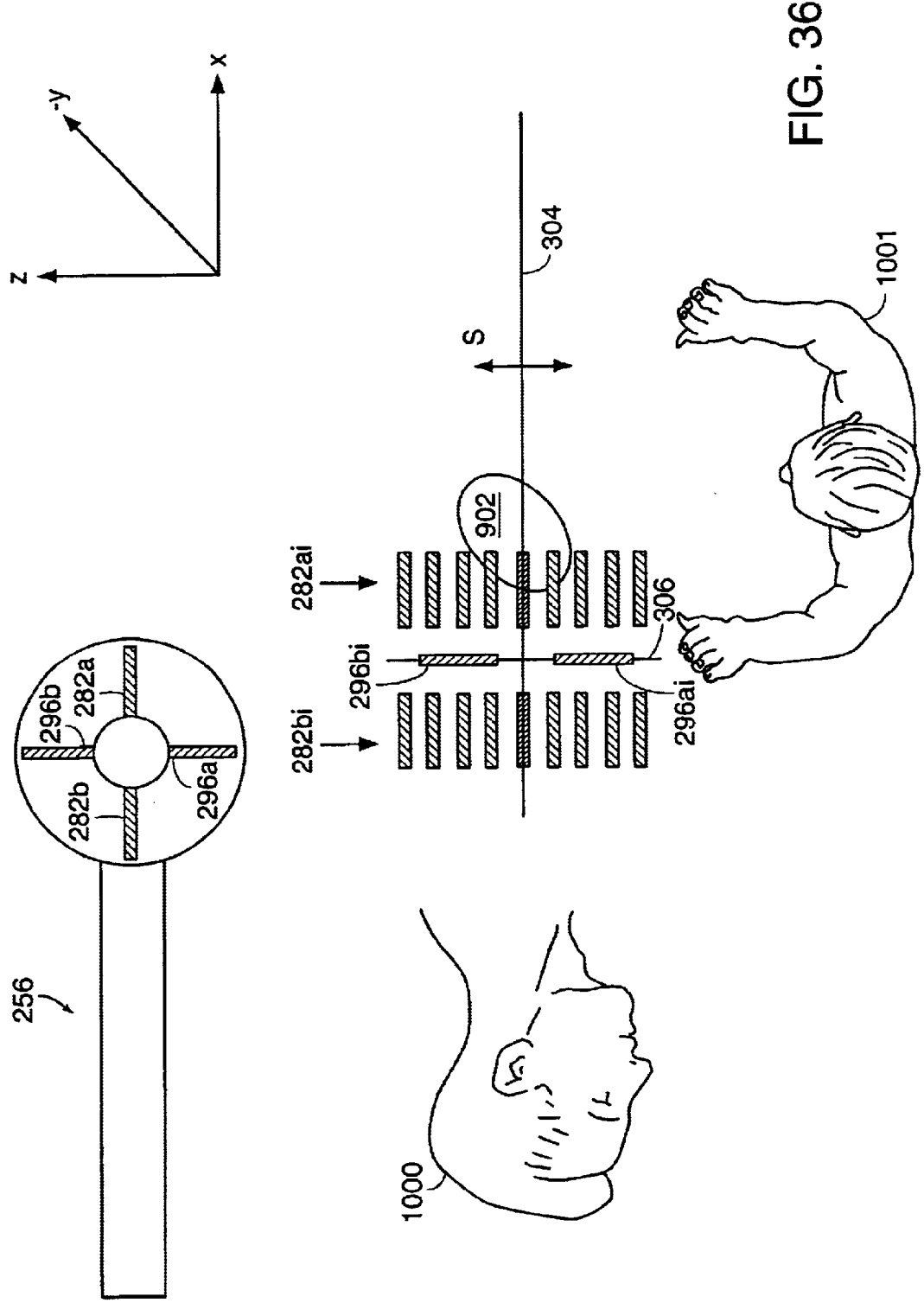
FIG. 36 depicts a highly schematic top view of the device of FIG. 31 in relation to a patient and a medical professional, and a schematic image display seen by the medical professional while positioning the device and/or components of the device in relation to a first axis.

In FIG. 34, a needle guiding apparatus 256 is situated above a patient's 1000 left side, with the patient 1000 facing the medical professional. The entire apparatus 256 is not shown, as designated by a blank area 302. A source of energy, such as an x-ray head 904 of an x-ray emitting device, projects energy. The x-ray head 904 is shown in two different positions 904a and 904b. The medical professional identifies an entry site based on a patient's anatomy (e.g., the region near the twelfth rib is one appropriate entry site) and positions the apparatus 256. The apparatus 256 is horizontal and parallel to the length of an operating table 906 in the x-axis direction and either touches or is close to the patient 1000. The medical professional 1001 first determines the intended needle trajectory through a first plane 304 by rotating the x-ray head 904 in a first position 904a (direction S) in a y-z plane. A view from the perspective of the patient's feet of the same situation is shown in FIG. 35. The two positions 904a, 904b of the x-ray head 904 are along the first plane 304 and appear to overlap although the x-ray head 904 in a second position 904b is behind the x-ray head 904 in a first position 904a in this view. As shown in FIG. 36, the radiopaque bars of the first band 282a, 282b form images 282ai, 282bi on a display screen when the fluoroscope is in operation. The orientation of the needle guiding device 256 (shown in a highly schematic fashion) is shown relative to the screen display. As the x-ray head 904 positioned in the first position 904a is rotated in direction S, images 282ai, 282bi of the radiopaque bars 282a, 282b of the first band move in the fluoroscope display (shown as multiple bar images 282ai, 282bi). The rotation of the x-ray head 904

(direction S) is continued until at least one of the images 282*ai*, 282*bi* of the bars 282*a*, 282*b* of the first band is aligned with the target calyx 902, shown, for example, as the darkened image bars 282*ai*, 282*bi*. Images 296*ai*, 296*bi* of the bars 296*a*, 296*b* of the second band are in an arbitrary position. When the images 282*ai*, 282*bi* of the bars 282*a*, 282*b* of the first band are aligned, the x-ray head 904 is locked in place and cannot rotate in direction S. This procedure defines the first plane 304.

Next the angle of the guide shaft 284 is adjusted so that it is in the first plane 304. The angle of the guide shaft 284 is adjusted in the first plane 304 (direction R) by turning the handle 258 (direction R). A mark (not shown) on the end of the adjustment rod 264 can align with angle markings (not shown) provided on the lock 276 such that the mark moves as the handle 258 is turned (direction R) and aligns with the angle markings on the lock 276. When the angle indicated by the alignment of the mark and the angle marking matches the angle of the x-ray head 904, the guide shaft 284 is considered aligned with the first plane 304 (for example, as in FIG. 35, the guide shaft 284 might be moved in direction R to come into alignment with first plane 304). At that point, the medical professional tightens the screw 278 to lock the guide shaft 284 in position in the first plane 304.

The angle of the guide shaft 284 also can be aligned in the first plane 304 by using the image of the guide shaft 284*i* and the radiopaque bars 282*ai*, 282*bi*, as shown in FIGS. 37A–37D. FIGS. 37B and 37D show an image 284*i* of the guide shaft 284 that is not symmetrical about the axis of the image 282*ai*, 282*bi* of the first band. This type of image indicates that the guide shaft 284 is not in the first plane 304. In order to align the guide shaft 284, it is rotated in direction R, for example, with the handle 258. The rotation of the guide shaft 284 (i.e., rotation of the handle 258) is stopped when the image 284*i* of the guide shaft 284 is symmetrical about the axis formed by the image 282*ai*, 282*bi* of the first band, as shown in FIGS. 37A and 37C. In FIG. 37A the image 284*i* of the guide shaft 284 is symmetrical about the axis formed by the image 282*ai*, 282*bi* of the first band, while the image 284*i* of the guide shaft 284 is symmetrical about both the axis formed by the image 282*ai*, 282*bi* of the first band, and the axis formed by the image 296*ai*, 296*bi* of the second band in FIG. 37C. Once the image 284*i* of the guide shaft 284 is aligned along the axis formed by the image 282*ai*, 282*bi* of the first band, the screw 278 is tightened to lock the guide shaft 284 in position in the first plane 304. The result in FIG. 37C (proper alignment in both the first plane 304 and a second plane 306) may occur in some instances without additional alignment steps, but, if less than proper alignment in both planes 304, 306 occurs, such as shown in FIG. 37A, then further alignment steps may be used.

Figure 38:
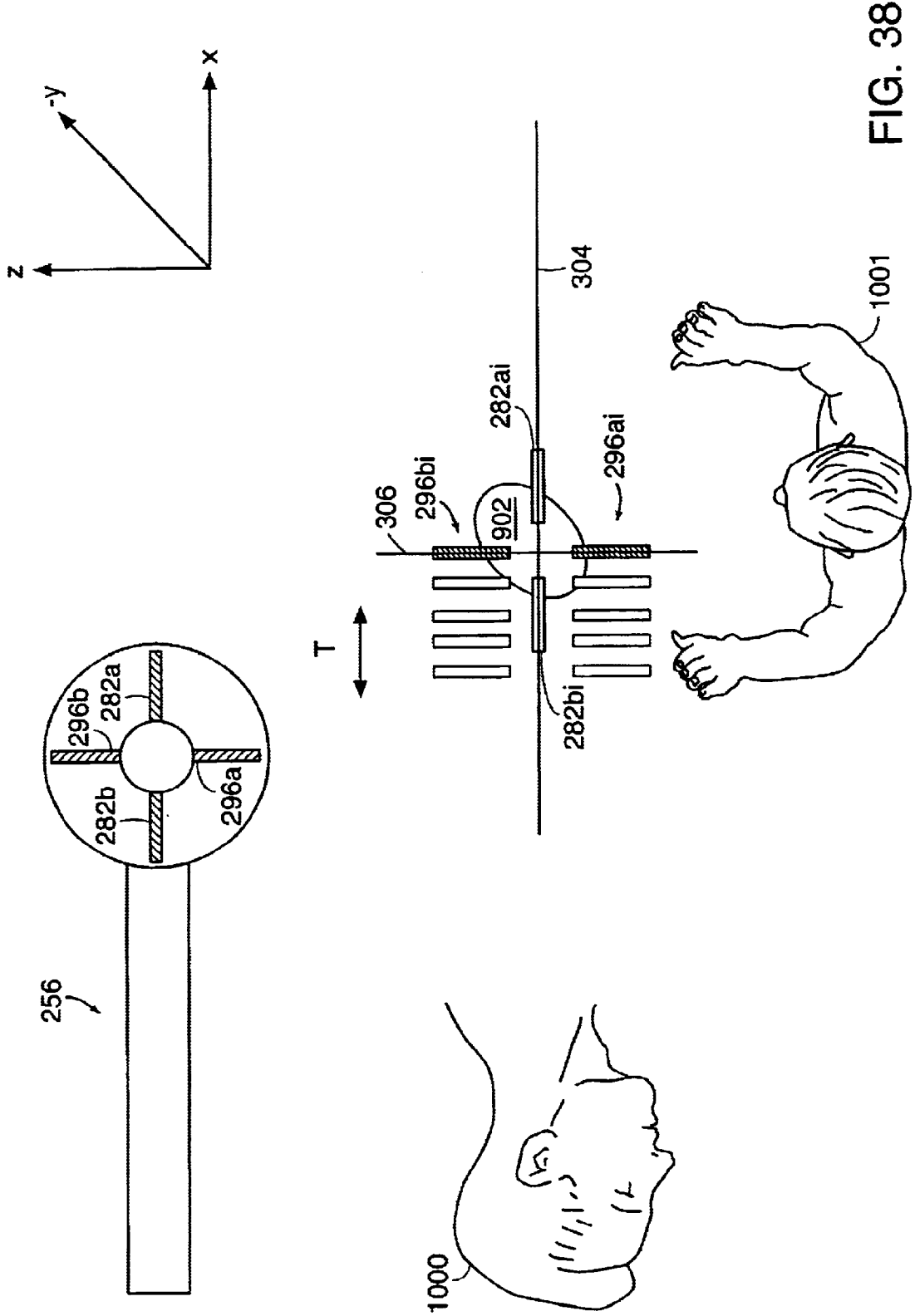
FIG. 38 depicts a highly schematic top view of the device of FIG. 31 in relation to a patient and a medical professional, and a schematic image display seen by the medical professional while positioning the device and/or components of the device in relation to a second axis.

Once the guide shaft 284 is aligned along the axis formed by the image 282*ai*, 282*bi* of the first band, the second plane 306 can be determined. With the x-ray head 904 of the fluoroscope locked in the first plane 304, the x-ray head 904 is rotated in the first plane 304 (for example, from the first x-ray head position 904*a* to the second x-ray head position 904*b*, i.e., direction T, as shown in FIG. 34). The direction of movement T in the first plane 304 generally is along the length of the patient 1000, from the head to toe, and vice versa. As shown in FIG. 38 in relation to a highly schematic depiction of the needle guiding device 256, patient 1000, and medical professional 1001, the radiopaque bars of the second band 296*a*, 296*b* form images 296*ai*, 296*bi* on a display screen when the fluoroscope is in operation. As the x-ray head 904 is rotated in direction T, images 296*ai*, 296*bi* of the radiopaque bars 296*a*, 296*b* of the second band move in the fluoroscope display (shown as multiple bar images 296*ai*, 296*bi*). The rotation of the x-ray head 904 (direction T) is continued until at least one of the images 296*ai*, 296*bi* of the bars 296*a*, 296*b* of the second band is aligned with the target calyx 902, shown, for example, as the darkened image bars 296*ai*, 296*bi*. When the images 296*ai*, 296*bi* of the bars 296*a*, 296*b* of the second band are aligned, the x-ray head 904 is locked in place and cannot rotate in direction T. This procedure defines the second plane 306. At this point, the first plane 304 and the second plane 306 are perpendicular.

Next the angle of the guide shaft 284 is adjusted so that it is in the second plane 306. The angle of the guide shaft 284 is adjusted by moving the control shaft 290 (direction P) in the first plane 304. Angle markings (not shown) can be provided on the handle 258 and/or the connector 288 and/or the control shaft housing 300 such that as the control shaft 290 is moved (direction P) it aligns with the angle markings, indicating the angle of the control shaft 290 (and the guide shaft 284). When the indicated angle matches the angle of the x-ray head 904, then the guide shaft 284 is aligned with the second plane 306. At that point, the medical professional tightens the control nut 292 to lock the guide shaft 284 in position in the second plane 306 while the guide shaft 284 is already locked in position in the first plane 304.

Figure 39C:
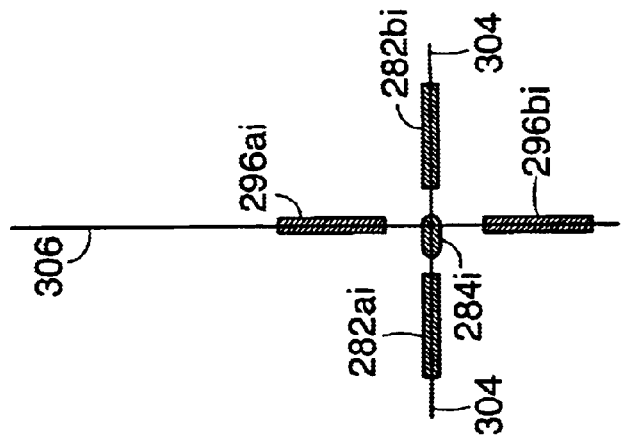
FIG. 39C depicts a schematic view of a display in which a guide shaft of the embodiment of FIG. 31 is not symmetric about a second axis.
Figure 39B:
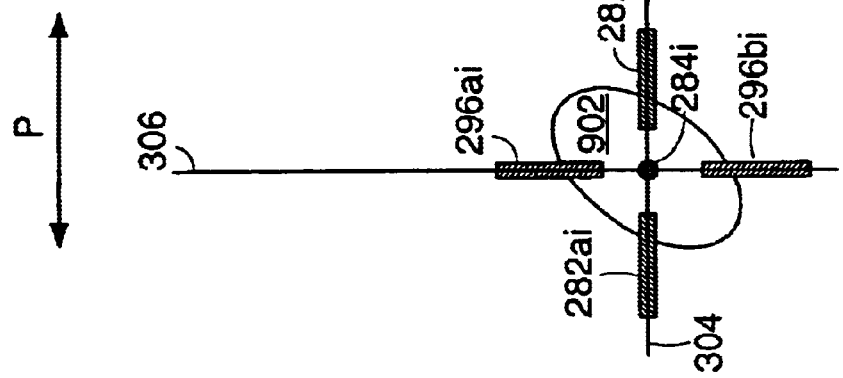
FIG. 39B depicts a schematic view of a display in which a guide shaft of the embodiment of FIG. 31 is symmetric about a first and second axis.
Figure 39A:
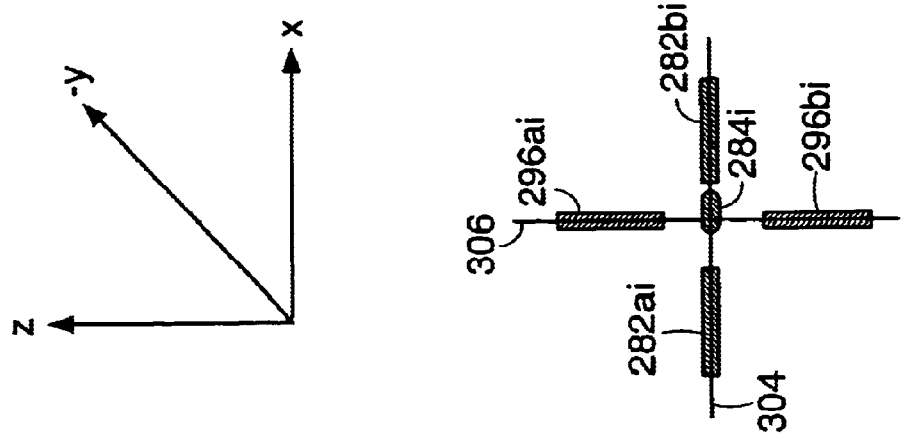
FIG. 39A depicts a schematic view of a display in which a guide shaft of the embodiment of FIG. 31 is not symmetric about a second axis.

The angle of the guide shaft 284 also can be aligned in the second plane 306 by using the image of the guide shaft 284*i* and the radiopaque bars 296*ai*, 296*bi*, as shown in FIGS. 39A–39C. In each of FIGS. 39A–C, the image 284*i* of the guide shaft 284 is already symmetrical about the first plane 304 due to previous alignment steps, discussed above. FIGS. 39A and 39C show an image 284*i* of the guide shaft 284 that is not symmetrical about the axis formed by the image 296*ai*, 296*bi* of the second band. This image situation indicates that the guide shaft 284 is not properly aligned in the second plane 306. In order to align the guide shaft 284, it is rotated in the first plane 304 (direction P), for example, with the control shaft 290. The rotation of the guide shaft 284 (i.e., movement of the control shaft 290) is stopped when the image 284*i* of the guide shaft 284 is symmetrical about the axis formed by the image 296*ai*, 296*bi* of the second band, as shown in FIG. 39B. In FIG. 39B the image 284*i* of the guide shaft 284 is now symmetrical about both the axis formed by the image 282*ai*, 282*bi* of the first band and the axis formed by the image 296*ai*, 296*bi* of the second band. Once the image 284*i* of the guide shaft 284 is aligned along the axis of the image 296*ai*, 296*bi* of the second band, the control nut 292 is tightened to lock the guide shaft 284 in position in the second plane 306. A proper entry needle trajectory to the target calyx is determined. At this point an entry needle, such as the one 254 shown in FIG. 31, can be inserted into the guide shaft 284 and through the patient's 1000 tissue to the target calyx 902. If the angle marker method of guide shaft 284 alignment is used, proper alignment (i.e., attainment of proper entry needle trajectory) can be confirmed by viewing the positioned device 256 on the display screen. A properly aligned device should appear as shown in FIG. 39B. If it is not aligned, the process can be repeated. This embodiment also can increase the accuracy with which the entry needle is placed and can decrease procedure time by allowing more rapid and accurate placement and access to the target calyx. A medical professional's hands are kept out of the x-ray field and tactile feedback as the entry needle is advanced into the patient and the target calyx is maintained.

An alternative method of aligning the guide shaft 284 in the first plane 304 that uses a slightly altered version of the needle guiding apparatus 256 of FIGS. 31–33 is shown in FIGS. 40A–41B. In this embodiment, the needle guiding apparatus can be horizontal to the operating table but need not be horizontal. In this situation, in addition to the first band of radiopaque material 282a, 282b in the device, two more bars 308a, 310a of radiopaque material are located, for example, in the alignment rod 264. These extra bars 308a, 310a of radiopaque material are situated such that they are parallel to the first band of radiopaque material 282a, 282b. In FIG. 40A, the x-ray head 904 is aligned along the first plane 304 with the target calyx 902. However, the guide shaft 284 is not properly aligned with the target calyx 902. As a result, the images 282ai, 308ai, 310ai of the three radiopaque bars 282a, 308a, 310a, shown in FIG. 40B, appear as three separate images. The adjustment rod 264 is rotated in direction R, for example with handle 258, and brought into proper alignment with the first plane 304, as shown in FIG. 41A. As a result, the images 282ai, 308ai, 310ai of the three radiopaque bars 282a, 308a, 310a, shown in FIG. 41B, are superimposed and appear as a single image. In certain other embodiments, the devices of the invention can have two parallel radiopaque bars (rather than three) or can have more than three parallel radiopaque bars. Again, alignment of the guide shaft 284 is indicated when the images of the bars are superimposed.

Two other alternative methods of aligning the guide shaft 284 in an image plane 305 that use slightly altered versions of the needle guiding apparatus 256 of FIGS. 31–33 are shown in FIGS. 48A–50 and FIGS. 51A–51F. These two embodiments are designed for use with an MRI device or a CAT-scan device, rather than for use with an x-ray emitting device and a fluoroscope. When using such devices, the device can be immediately aligned with the target calyx in a single image plane 305 (i.e., the procedure can be performed without the step of perpendicular aligning bars contained within the base, as was done with bars 282a, 282b, 296a, 296b above, to define the first plane 304 and the second plane 306). Embodiments for use with an MRI device or a CAT-scan device do not use radiopaque materials, such as metals, for an imaging sight because metal produces a distorted screen display image. These embodiments instead would use a material with a particular density, such as a fluid-filled or gas-filled structure. Additionally, because the energy field produced by an MRI device or a CAT-scan device is not as harmful to human tissue as the energy field produced by an x-ray emitting device, embodiments of needle guiding apparatus for use with an MRI device or a CAT-scan device can be constructed such that they do not have handle extensions or remote needle guiding capability. For example, medical professional could directly manipulate a guide shaft. However, for the sake of simplicity, the two alternative embodiments shown in FIGS. 48A–50 and FIGS. 51A–51F are presented as essentially the same as that shown in FIGS. 31–33 except for the placement of and material composition of the imaging sight. Also, rather than the medical professional placing the device in the orientation shown in FIGS. 34–39C, the device is rotated 90 degrees from that orientation. Although the device still moves in directions P and R, the directions of movement P and R have been relabeled as Q and H, respectively, because directions of movement P and R are rotated 90 degrees relative to those shown in FIGS. 34–39C due to the 90 degree rotation of the device. Thus, directions of movement Q and H are rotated 90 degrees from directions of movement P and R, but the device still produces rotational movement as described above. These embodiments also can increase the accuracy with which the entry needle is placed and can decrease procedure time by allowing more rapid placement and access to the target calyx.

Figure 50:
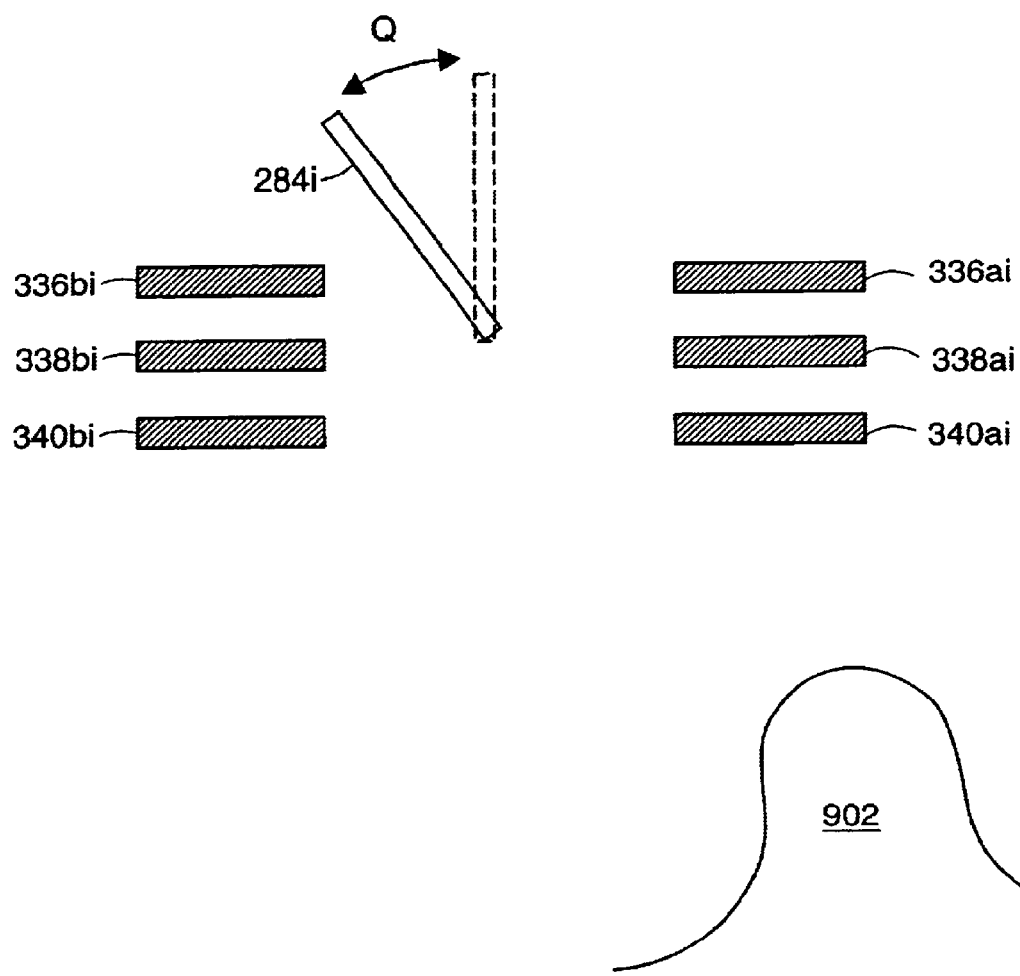
FIG. 50 depicts a schematic image display of the device in FIG. 49A in the position indicated in FIG. 49B and with the image of a guide shaft shown.

Now referring to FIGS. 48A–50, a needle guiding apparatus has three sets of parallel density bars 336a, 336b, 338a, 338b, 340a, 340b. One set of density bars 336a, 336b forms a first density band, a second set of density bars 338a, 338b forms a second density band, and a third set of density bars 340a, 340b forms a third density band. These density bands are disposed within the adjustment rod 264 and are located symmetrically about the guide shaft 284. In FIG. 48B, the MRI device or CAT-scan energy source 910 is aligned along the image plane 305. The second density band is also in the image plane 305. The needle guiding apparatus is situated above the patient's 1000 left side with the patient 1000 facing the medical professional. The needle guiding apparatus is horizontal as well as perpendicular to the length of the operating table 906 in the z-axis direction. The guide shaft 284 is not aligned within the image plane 305. Thus, as shown in FIG. 48C, an image (taken as a section through the image plane 305) shows only the images 338ai, 338bi of the density bars 338a, 338b of the second density band because only that density band is in line with the section taken by the MRI device or the CAT-scan device. However, as shown in FIGS. 49A–49C, the guide shaft 284 can be rotated (direction of movement H) to bring it into alignment with the image plane 305. Now, an image taken as a section will show all density bands because they are all aligned along the section line (i.e., the image plane 305). When the guide shaft 284 is aligned as shown in FIG. 49B, the image of the density bands changes such that the images 336ai, 336bi of the density bars 336a, 336b of the first density band are parallel with the images 338ai, 338bi of the density bars 338a, 338b of the second density band and are parallel with the images 340ai, 340bi of the density bars 340a, 340b of the third density band. This change in alignment can occur, for example, as shown in FIG. 50 where an image 284i of the guide shaft 284 is shown in relation to the images 336ai, 336bi, 338ai, 338bi, 340ai, 340bi of the density bars 336a, 336b, 338a, 338b, 340a, 340b of the three density bands and the target calyx 902. Also, in FIG. 50, the image 284i of the guide shaft 284 can be moved in direction Q from a position similar to that shown in FIG. 49B (dotted outline of the image of a guide shaft in FIG. 50) to a position aligned with the target calyx 902 similar to that shown in FIG. 50. Once the guide shaft 284 is fully aligned by moving the guide shaft 284 in both the H and Q directions of movement, an entry needle can be inserted through the guide shaft 284.

Another layout of density bars 350a, 350b, 352a, 352b, 354a, 354b for the embodiment shown in FIGS. 51A–51F is useful for bringing the center of the guide shaft 284 into alignment with the image plane 305. As shown in FIGS. 51A–51D, the embodiment has the same layout of components as the embodiment shown in FIGS. 31–33, except the density bands 350a, 350b, 352a, 352b, 354a, 354b, that are viewed on the MRI device or CAT-scan device, are different in orientation and composition from the radiopaque bands shown in FIGS. 31–33. A first density band is made up from the top two density bars 350a, 350b, a second density band is made up from the middle two density bars 352a, 352b, and a third density band is made up from the bottom two density bars 354a, 354b. As seen in the various views, the density bars 352a, 352b of the second density band are parallel with the first and third density bands, but are situated such that they are at an angle relative to an axis formed through the density bars 350a, 350b of the first density band and are at the same angle relative to an axis formed through the density bars 354a, 354b of the third density band.

Figure 51A:
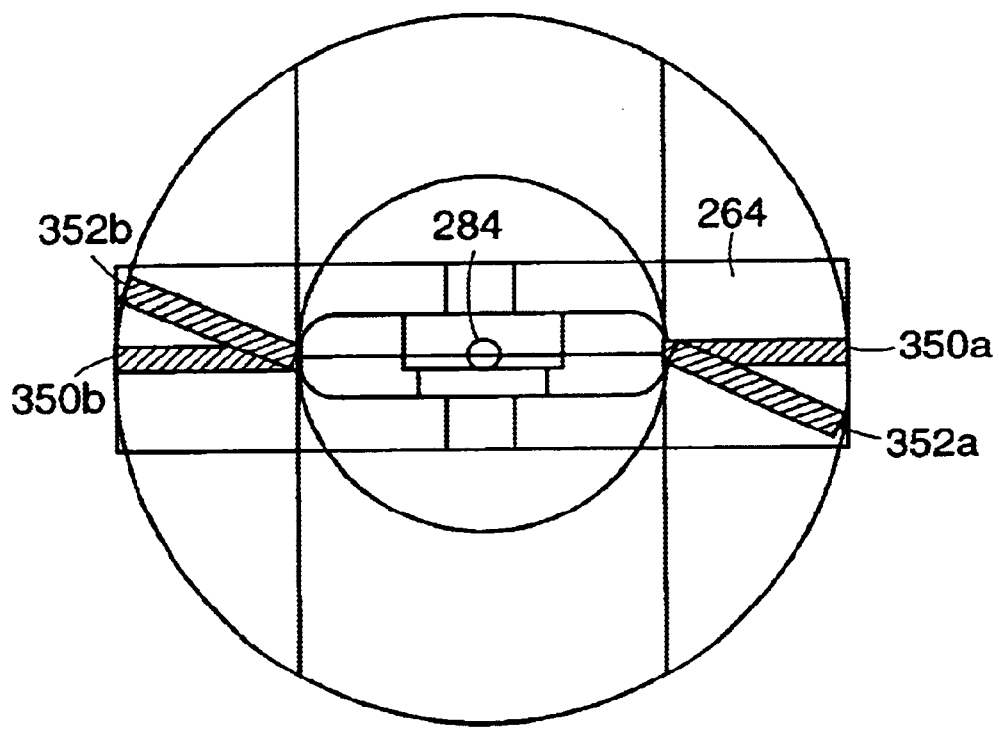
FIG. 51A depicts a schematic top view of a slightly altered embodiment of the device of FIG. 31 for use with a magnetic resonance imaging device ("MRI device") or a computerized axial tomography scanning device ("CAT-scan device").
Figure 51C:
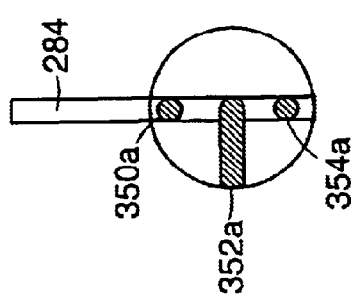
FIG. 51C depicts a schematic section view taken at a point where an alignment bar reaches an edge of a ring of the embodiment of FIG. 51A.
Figure 51B:
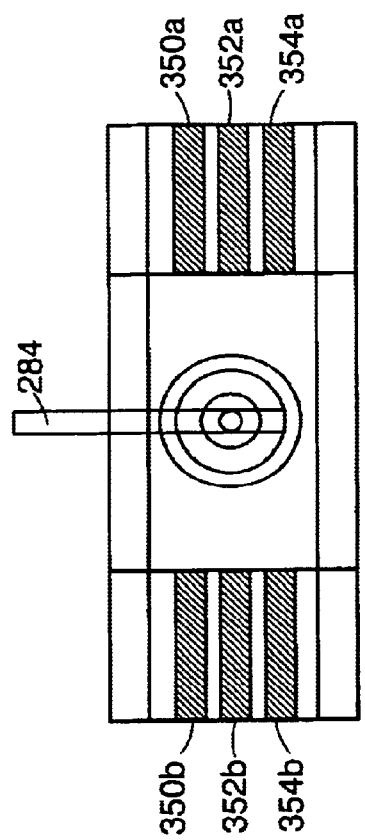
FIG. 51B depicts a schematic side view of the embodiment of FIG. 51A.
Figure 51D:
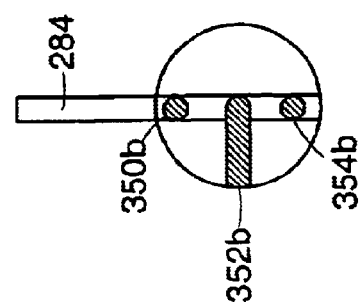
FIG. 51D depicts a schematic section view taken at a point where an alignment bar reaches an edge of a ring (on the opposite side of the ring from FIG. 51C) of the embodiment of FIG. 51A.
Figure 51E:
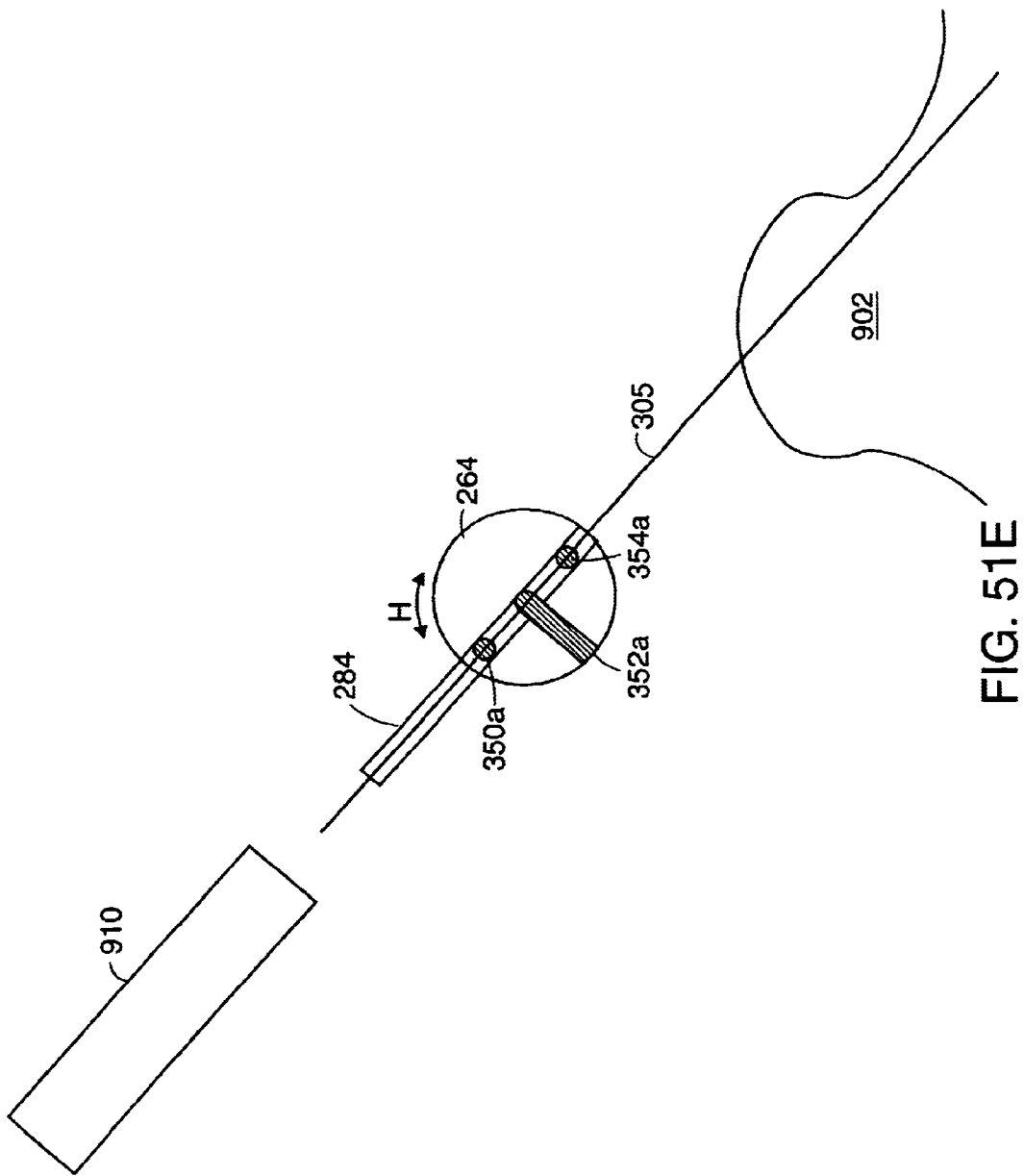
FIG. 51E depicts the embodiment of FIG. 51A that is aligned with a target.
Figure 51F:
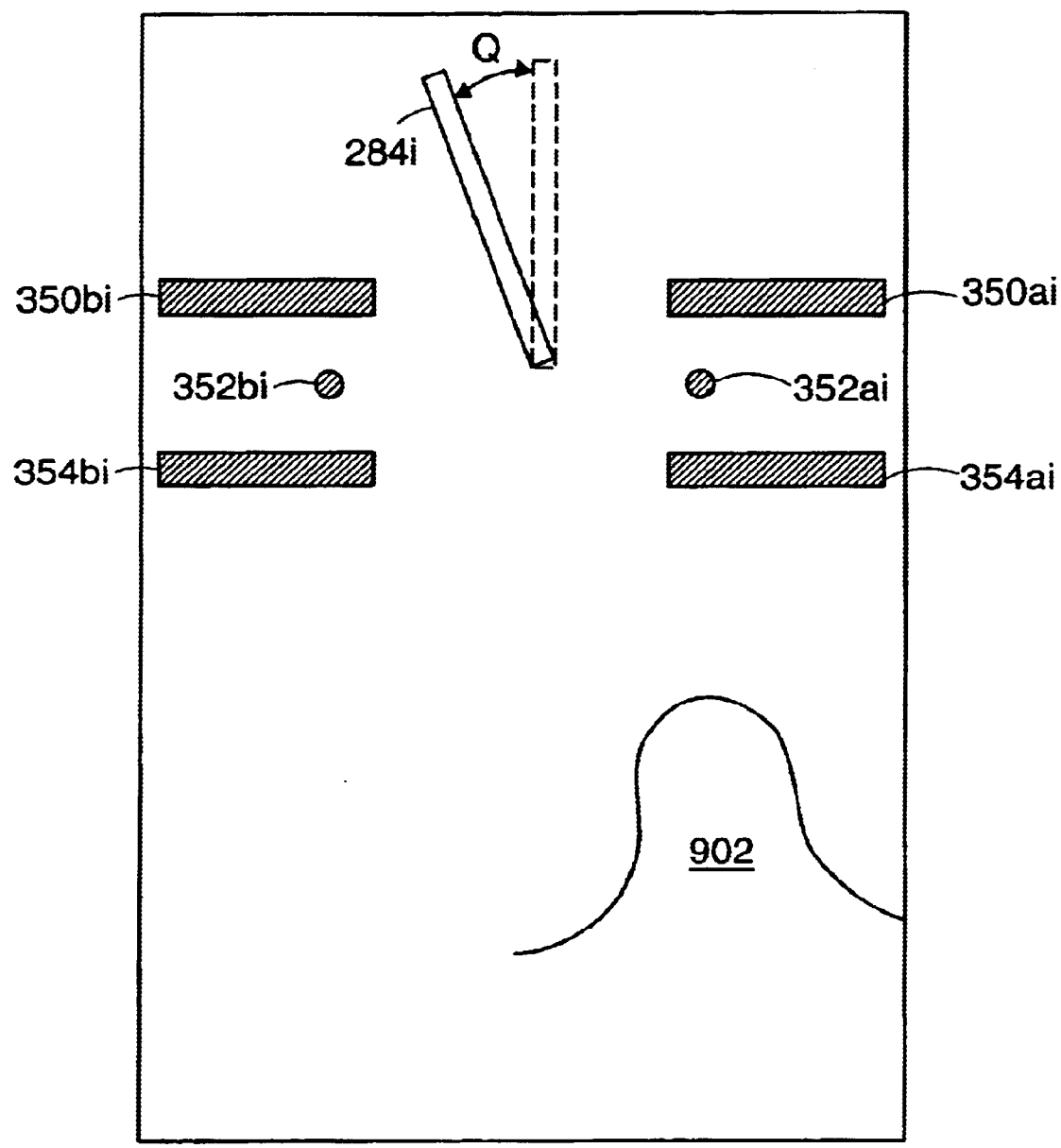
FIG. 51F depicts a schematic image display of the embodiment of FIG. 51A in the position shown in FIG. 51E.

First, the needle guiding apparatus is placed on or near the patient. Under the guidance of an MRI device or a CAT-scan device, the medical professional discerns the image plane 305 by aligning the second density band with the target calyx. If two spots, corresponding to the two density bands 252a, 252b of the second density band, are seen in alignment with the target calyx 902, then the imaged section corresponds with the image plane 305. If one or no spots are seen in alignment with the target calyx, then another section is viewed until an aligned state is observed. Once the image plane 305 is defined, the guide shaft 284 is aligned within the image plane 305 (for example, by rotating the adjustment rod 264 in direction H or shifting the device along the patient's skin). When the guide shaft 284 is aligned with the target calyx 902 and the MRI device source or CAT-scan source 910 along the image plane 305, as shown in FIG. 51E, a particular image is formed. The image shown in FIG. 51F indicates that, when aligned, the section image taken by the MRI device or CAT-scan device down the image plane 305 will show the first density band as two bar-shaped images 350ai, 350bi on the top of the image, the second density band as two spot shaped-images 352ai, 352bi in the middle, and the third density band as two bar-shaped images 354ai, 354bi on the bottom. The image 284i of the guide shaft 284 is aligned with the target calyx 902. Also, if the guide shaft 284 is in the image plane 305 but not aligned with the target calyx 902, the dotted image of the guide shaft 284 indicates how a guide shaft 284 might be moved along direction Q to bring the guide shaft into alignment with the target calyx 902. Once the guide shaft 284 is aligned, an entry needle can be inserted through the guide shaft 284.

Figure 15B:
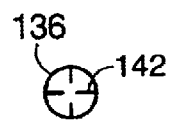
FIG. 15B depicts a top view of an entry needle in the embodiment of FIG. 15A.
Figure 15A:
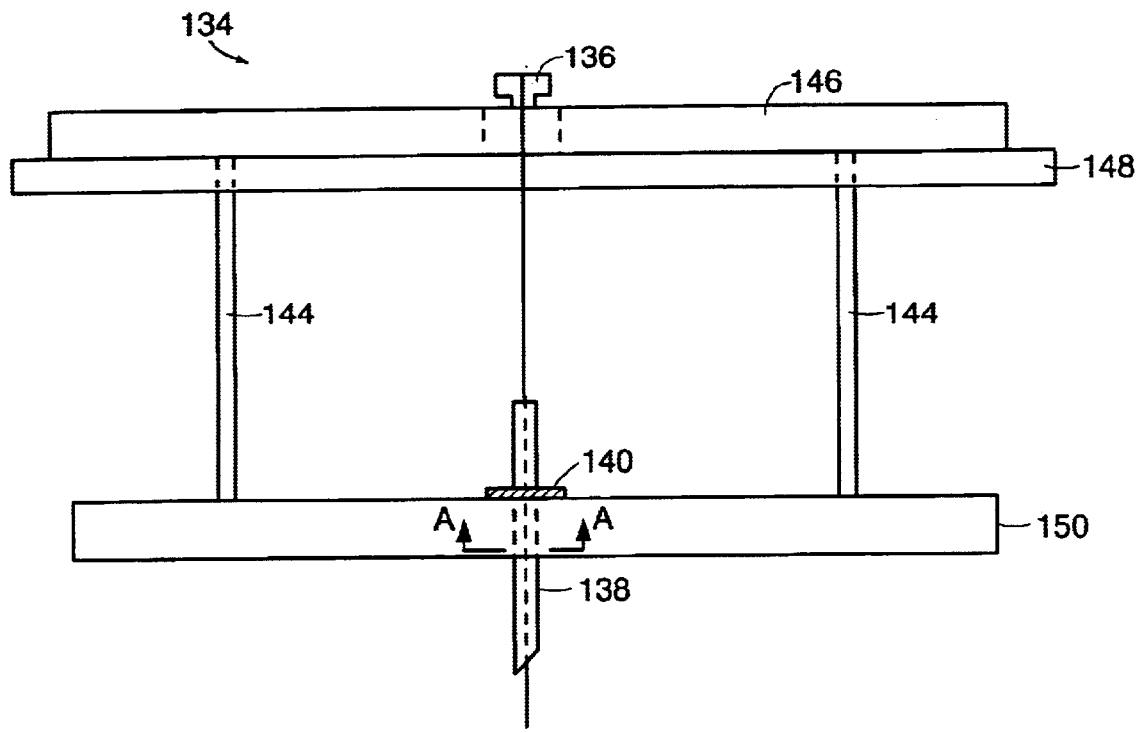
FIG. 15A depicts a schematic side view of a device with an adjustable guide needle, according to the invention.
Figure 16:
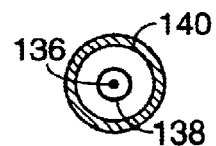
FIG. 16 depicts a schematic cross-section taken through line A—A of the embodiment of FIG. 15A.

Another embodiment of the invention, shown in FIGS. 15A–17, is a needle guiding apparatus 134 that has several components: an entry needle 136, a guide needle 138, a radiopaque donut 140, radiopaque crosshairs 142, bar guides 144, an upper driving bar 146 (alternatively called the "upper bar"), a lower driving bar 148 (alternatively called the "lower bar"), and an adjustment rod 150. The entry needle 136 is affixed in perpendicular fashion in the lower bar 148 and passes through a hole in the upper bar 146. The upper driving bar 146 is fixed to the bar guides 144 which are fixed to the cylindrical adjustment rod 150. The guide needle 138 is fixed in perpendicular fashion to the adjustment rod 150. The radiopaque donut 140 is affixed to the adjustment rod 150 or on or around the guide needle 138. The upper bar 146 is used to push the guide needle 138 into place. The lower bar 148 is used to drive the entry needle 136 through the guide needle 138 as it slides down the bar guides 144. The coaxial arrangement of the radiopaque donut 140, guide needle 138, and entry needle 136 is shown in FIG. 16 as a section taken through line A—A of FIG. 15A.

Figure 17:
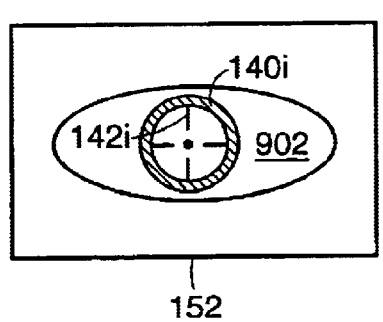
FIG. 17 depicts a schematic representation of a screen display of the embodiment of FIG. 15A while the device is in use.

The apparatus 134 provides a means of aligning the entry needle 136 with a target calyx. The entry site on the patient's back is identified by aligning the radiopaque donut 140 on the distal end of the apparatus 134 with the radiopaque crosshairs 142 on the proximal end of the apparatus 134 and with the target calyx. This alignment can be viewed on the screen of a fluoroscope 152, and one example of the screen display of an aligned device 134 is shown in FIG. 17. An image 142i of the cross-hairs 142 is shown encircled by a circular image 140i of the radiopaque donut 140 and aligned with the target calyx 902.

The angle of the x-ray head and the fluoroscope must approximately match the angle of the apparatus 134 with respect to the point of entry on the patient and match the entry needle's 136 intended entry trajectory. The device may be used in vertical orientation or most other orientations that the medical professional may desire. Because the apparatus 134 has the ability for the needle 136 to enter in at an angle other than vertical, the medical professional can better customize the needle's 136 approach into the kidney. An angle indicator can be included (not shown), for example, on the adjustment rod 150 to allow a physician to discern the guide needle's 136 angle relative to the surface of the patient's skin. The guide needle 138 is advanced about 2–3 cm into the patient's back by the medical professional pushing on the upper driving bar 146 which is fixed to the vertical guides 144 and cylindrical adjustment rod 150. Alternatively, the guide needle 138 may be advanced by the medical professional grasping the adjustment rod 150 at either end and pushing the adjustment rod 150 down on the patient's back. The depth to which the guide needle 138 advances into the patient can be adjustable. In this design, the adjustment rod 150 is of sufficient length to allow the medical professional to use the device 134 with his/her hands out of the x-ray field. The upper driving bar 146 can be, for example, but without limitation, approximately 10 inches in length, thereby allowing the medical professional to use the device 134 without having his/her hands in the x-ray field. Once the guide needle 138 has been positioned, the medical professional may re-check the alignment of the entry needle 136 using the distal radiopaque donut 140 and the proximal radiopaque crosshairs 142. The entry needle 136 can be advanced by the medical professional pushing down on the lower driving bar 148, and the lower driving bar 148 moves over the vertical guides 144. The lower driving bar 148 is slightly longer than the upper bar 146 to allow the medical professional to push it down without also pushing the upper bar 146. This design allows the lower bar 148 to be moved independent of the upper bar 146. Alternative designs can involve locking and unlocking the upper 146 and lower 148 bars to allow dependent or independent use and may be accomplished in a variety of ways. The lower bar 148, similar to the upper 146, is of sufficient length to allow the medical professional to use the device without exposing his/her hands to the x-ray field. Prolonged exposure to x-rays are not desirable due to health risks. Therefore, any features which allow the medical professional to keep his/her hands out of the x-ray field are advantageous.

In addition to keeping a medical professional's hands away from the x-ray field, the present device 134, with greater stability than conventional techniques, allows the medical professional to retain tactile feedback and also allows a syringe (not shown) to be attached for aspiration of urine. The device 134 also may be used while performing triangulation access if the medical professional so desires. Lastly, the device 134 or the entry needle 136 may have a feature which allows the medical professional to detect when the target calyx has been pierced, reducing the medical professional's reliance on tactile feedback.

Another embodiment of the invention, shown in FIGS. 18A–21, is a needle stage 154 and a separate entry needle 136. The needle stage 154 includes a base 156, an alignment rod 150, a guide needle 138, a radiopaque donut 140 and a locking mechanism 160. The cylindrical alignment rod 150 is free to rotate about its axis in the base 156 of the needle stage 154 (as indicated with arrow L in FIG. 18A). The guide needle 138, typically 12–14 gauge in diameter, is fixed in perpendicular fashion through the center of the alignment rod 150. The radiopaque donut 140 is fixed on the alignment rod 150 or is fixed on or around the guide needle 138. The locking mechanism 160 (such as a screw) interacts with the base 156 and alignment bar 150 to prevent the components from moving relative to one another.

The medical professional typically will hold the device by grasping the ends of the alignment rod 150. The alignment rod 150 can be, for example, but without limitation, approximately 10 inches in length, thereby allowing the medical professional to use the device 154 without exposure of his/her hands to the x-ray field. The physician can rotate the alignment rod 150 and thereby rotate the entry angle of the guide needle 138. The entry site on the patient's back will be identified by aligning the image of the radiopaque donut 140 on or around the image of the guide needle 138 with the target calyx 902. The angle of the x-ray head and the fluoroscope must approximately match the entry angle of the guide needle 138 and the entry needle's 136 intended entry trajectory. Once the radiopaque donut 140 is aligned with the target calyx 902, the medical professional may advance the guide needle 138 into the patient's back by pushing down on the cylindrical alignment rod 150. When the guide needle 138 is advanced 2–3 cm, the base 156 will bottom out on the surface of the patient's skin. The position of the guide needle 138 may then be locked into place by activating the locking mechanism 160. This locking mechanism 160 can be, for example, but without limitation, a screw which drives through the base 156 and exerts perpendicular force onto the outer diameter of the cylindrical alignment rod 150. The base 156 may also have a sticky underside which would provide another means of securing it to the patient's skin or drape. An angle indicator 162 can be included, for example, on the alignment rod 150 to allow a medical professional to discern the guide needle's 138 angle relative to the surface of the patient's skin (FIG. 19B). The depth to which the guide needle 138 advances into the patient can be adjustable.

Once the base 156 has been locked into position, the medical professional may insert the entry needle 136, typically 18–22 gauge in diameter, into the guide needle 138. Variations of this entry needle 136 are described throughout the specification. A conventional, commercially available entry needle may be advanced through the guide needle 138. Additionally, an entry needle with radiopaque crosshairs on its proximal end may be advanced through the guide needle 138, allowing the medical professional to monitor the alignment of the needle during advancement. An entry needle 136 that may include radiopaque crosshairs 142 (shown as a section taken along line B—B through the entry needle 136 in FIG. 18B) may optionally be affixed in perpendicular fashion to a driving bar 158 (FIG. 18A) that is similar to the one shown in FIGS. 15A–17, allowing the medical professional to drive the entry needle 136 while keeping his/her hands out of the fluoro field. A driving bar 158 may be provided which includes radiopaque crosshairs and allows attachment to a commercially available needle. The radiopaque crosshairs would align with the axis of the attached entry needle (in a manner similar to that shown in FIG. 21), allowing any needle to have improved targeting capabilities. A screen display of a fully aligned device 154 is shown in FIG. 21. A circular image 140i of the radiopaque donut 140 encircles the image 136i of the entry needle 136 and is aligned with an image 142i of the radiopaque cross-hairs and the target calyx 902. The initial alignment of the device (without the entry needle 136) would appear on the screen display as the circular image 140i of the radiopaque donut 140 encircling the target calyx 902. This alignment would indicate that the guide needle 138 was in line with the target calyx 902 and that the entry needle 136 could be inserted through the guide needle 138 in a proper trajectory to reach the target calyx 902.

Another embodiment (not shown) of the invention adds the base 156 and the locking mechanism 160 of the embodiment shown in FIGS. 18A–21 onto the embodiment shown in FIGS. 15–17. The base 156 is disposed about the adjustment rod 150 in a similar manner to the way the base 156 is shown disposed about the alignment rod 150 in FIGS. 18–21. The locking mechanism 160 an operate in the same manner as described above.

Generally, the invention can save procedure time by giving the medical professional a tool to better control and align the movement of an entry needle through a patient's back and into the target calyx of a kidney. Additionally, the embodiment shown in FIGS. 15A–17 provides the advantages of allowing activation of the device 134 without having a medical professional's hands in the x-ray field, allowing access to the target at an angle other than vertical, and allowing the medical professionals to have tactile feedback during access. The embodiment shown in FIGS. 18A–21 provides an additional advantage by allowing the medical professional to lock the position of the guide needle 138. Finally, the embodiment combining the embodiment shown in FIGS. 15A–17 with the embodiment shown in FIGS. 18A–21 provides at least the advantages described above, in a single device.

Another embodiment of the invention, shown in FIGS. 28–30B, consists of a gun-like device 168 that has a housing 170 that contains the inner workings of the device 168. A hole 182 on one end of the device 168 accepts an entry needle (shown in FIGS. 29 and 30A as needle 184, 186, respectively), the device 168 provides a way to align the needle 168 with, for example, a target calyx. Radiopaque crosshairs 176 are disposed adjacent the hole 182. The entry site on the patient's back will be identified as described above, using a guide needle 180 (for example, a 14 gauge needle) which extends from the tip of the gun 168. The entry needle (for example, an 18 gauge entry needle) is locked into the gun 168 on the same axis as the guide needle 180, such that, when the gun 168 is activated by moving the trigger 172 in direction M, the entry needle will pass through the guide needle 180. A disc 178 with spokes surrounds the guide needle 180 coaxially. The gun 168 has a radiopaque donut (not shown) on its distal end that is used with the radiopaque crosshairs 176 on its proximal end to align the entry needle in the gun 168 with the target calyx.

Once the gun 168 is rotated (with the x-ray head and the fluoroscope vertical), such that the target calyx and radiopaque crosshair 176 are aligned in the radiopaque donut, the guide needle 180 will be pushed vertically through the patient's skin and fatty tissue. The guide needle 180 will act as a guide for the entry needle to pass through it. Once the tip of the guide needle 180 is pushed into place, approximately 2½–3 cm below the surface of the skin, the gun 168 is ready for activation. When the gun 168 is fully aligned, the entry needle will be driven into the target calyx through the guide needle by manually squeezing the gun's trigger 172 in direction M. Guide needles and entry needles of sizes other than 14 gauge and 18 gauge, respectively, are envisioned, and these needles may be coaxial, with one needle passing through the other needle, as described above. Additionally, many types of entry needles with various functionalities are possible. For example, the entry needle 184 shown in FIG. 29 can sample fluids at its distal end and the entry needle 186 shown in FIG. 30A can detect light, particularly light produced by a light source 188 shown in FIG. 30B. These entry needles and other types of entry needles are described in more detail below. The gun 168 can also be used while performing triangulation access rather than a variation of the bullseye technique, if the medical professional so desires. Lastly, the device 168 can optionally have a datum window 174. The datum window 174 can, for example, display at least one piece of datum, to allow the medical professional to detect, for example, when the target calyx has been pierced.

The device 192 shown in FIGS. 26–27 is simpler than the device shown in FIGS. 28–30B and also can be used to drive an entry needle 194 in accordance with the invention. The entry needle 194 includes a small diameter needle 206 (e.g., a 19 gauge needle) contained within a larger diameter trocar 198 (e.g., an 18 gauge needle) having a hub 196. The entry needle 194 is driven through a guide needle 202 at the distal end of the device 192. In operating the device, a medical professional would grasp a distal handle 204 in one hand and move a proximal handle 208 towards the distal handle 204, in direction N. This movement advances the entry needle 194 through the guide needle 202. The guide needle 202 can be positioned in the patient in the manner as described for the embodiment shown in FIGS. 28–30B, such that the advanced entry needle 194 is driven into the patient's tissue. This device 192 has radiopaque crosshairs 208 disposed within the device (shown in cross section A—A in FIGS. 26 and 27) towards its proximal end and has a radiopaque donut 200 disposed toward the distal end of the device 192. This sighting arrangement is similar to the embodiment described in FIGS. 28–30B. Except for the manner of advancing the entry needle 194, the device 192 is targeted and used in a similar manner to that described for the device 168 described in FIGS. 28–30B.

Additionally, once a medical professional believes a target calyx has been located with the entry needle through, for example, positioning under the guidance of a fluoroscope or tactile feedback, the medical professional will confirm access. One manner of confirming access with entry needles that are currently used is to remove an inner portion of the entry needle, attach a syringe, and to aspirate fluid from the tip of the entry needle. Blood in the syringe indicates that the target has not been reached while urine or contrast dye (previously injected into the kidney to allow visualization of the kidney on the fluoroscope display) in the syringe indicates that the target has been reached.

Several embodiments of an entry needle are shown in FIGS. 22–25. Now referring to FIGS. 22 and 23, an entry needle 184 includes a cannula 224 in connection with (or as a single piece with) a "Y" shaped hub 228. The hub 228 has a branch 230 with a connector 222 at the proximal end of the branch 230. The cannula 224, which can be made of stainless steel, has an opening 210 at its distal end and contains a notched needle 214. The notched needle 214 rotates about an axis extending through the center of the cannula 224, and the notched needle can be about 18 to about 21 gauge. The notched needle 214 is a hollow needle, with a portion of the wall of the needle 214 removed (i.e., a notch 212). In a first position (FIG. 22), the portion of the notched needle 214 that is not notched is aligned with the opening 210, preventing fluid located outside of the entry needle 184 from entering into the cannula 224. In a second position (FIG. 23), the notched portion 212 of the notched needle 214 is aligned with the opening 210, allowing fluid located outside of the entry needle 184 to enter the cannula 224. A knob 216 with markings for "on" 218 and "off" 220 is attached to the notched needle 214 such that when the knob 216 is rotated, the notched needle 214 is rotated. Specifically, the "on" marking 218 is aligned with an indicator (not shown) when the notched needle is in the second position and the "off" marking 220 is aligned with the indicator when the notched needle is in the first position. When in the second position, the notch 212 also is aligned with the branch 230 in the "Y" shaped hub 228 at the proximal end of the entry needle 214. Thus, fluid entering the cannula 224, travels along the inside of the cannula 224 and the notched needle 214 until it reaches the branch 230 and is diverted into the branch 230. A seal 226 at the proximal end of the cannula 224 prevents fluid from escaping at the end of the cannula 224. The seal 226, for example, can be an "O-ring" disposed about the notched needle 214. Once fluid has entered the cannula 224 it flows and/or is drawn towards the proximal end of the entry needle 184. Fluid can be conducted along the cannula 224 by attaching a syringe (not shown) to the connector 222, drawing back on the plunger in the syringe to create a vacuum, and drawing fluid through the device 184 towards the proximal end.

Figure 22:
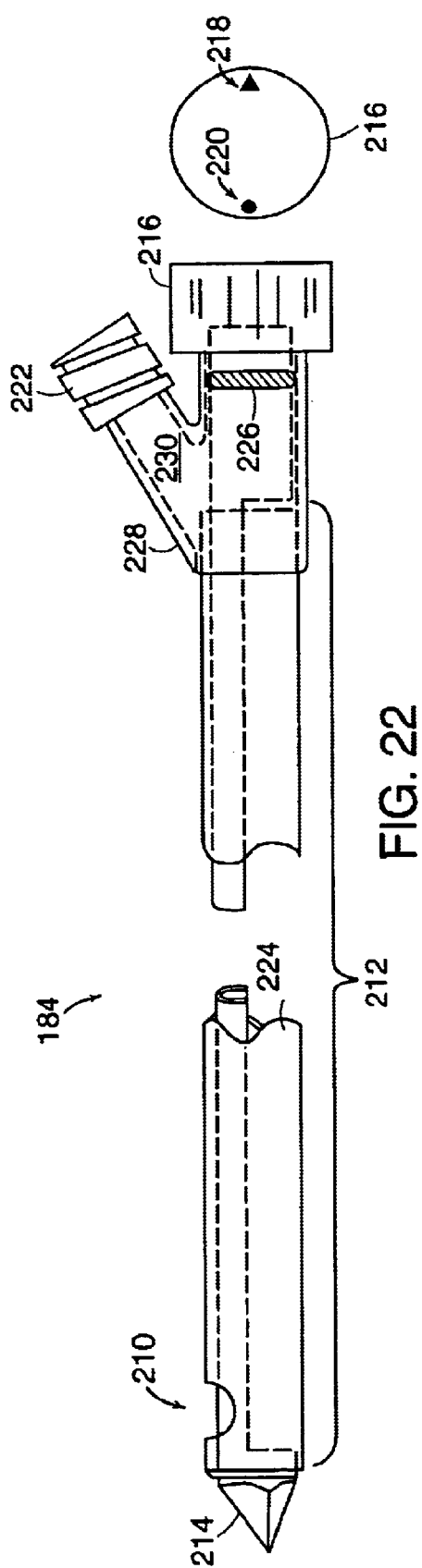
FIG. 22 depicts a schematic side view of an entry needle in an "off" position.
Figure 23:
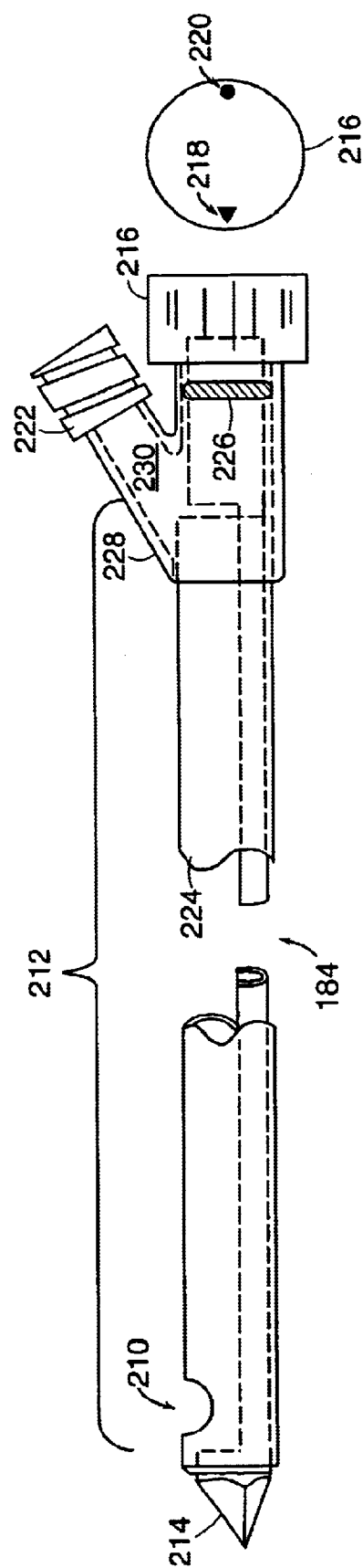
FIG. 23 depicts a schematic side view of the embodiment of FIG. 22 in an "on" position.

The entry needle 184 shown in FIGS. 22 and 23 avoids having to remove the inner portion of the entry needle in some current entry needle designs by allowing for selectable fluid access at the turn of a knob. Removing this extra removal step can save time during the procedure. Also, the syringe can be continuously attached to the connector 222 to avoid having to continually attach and disengage the syringe if kidney access must be confirmed multiple times. Additionally, the syringe can be used to introduce materials (such as additional contrast dye that is used to visualize the kidney on a fluoroscope) into a patient through the cannula. Also, the notched needle 214 can be removed once access is obtained and replaced with other medical instruments and/or a guide wire.

Figure 24:
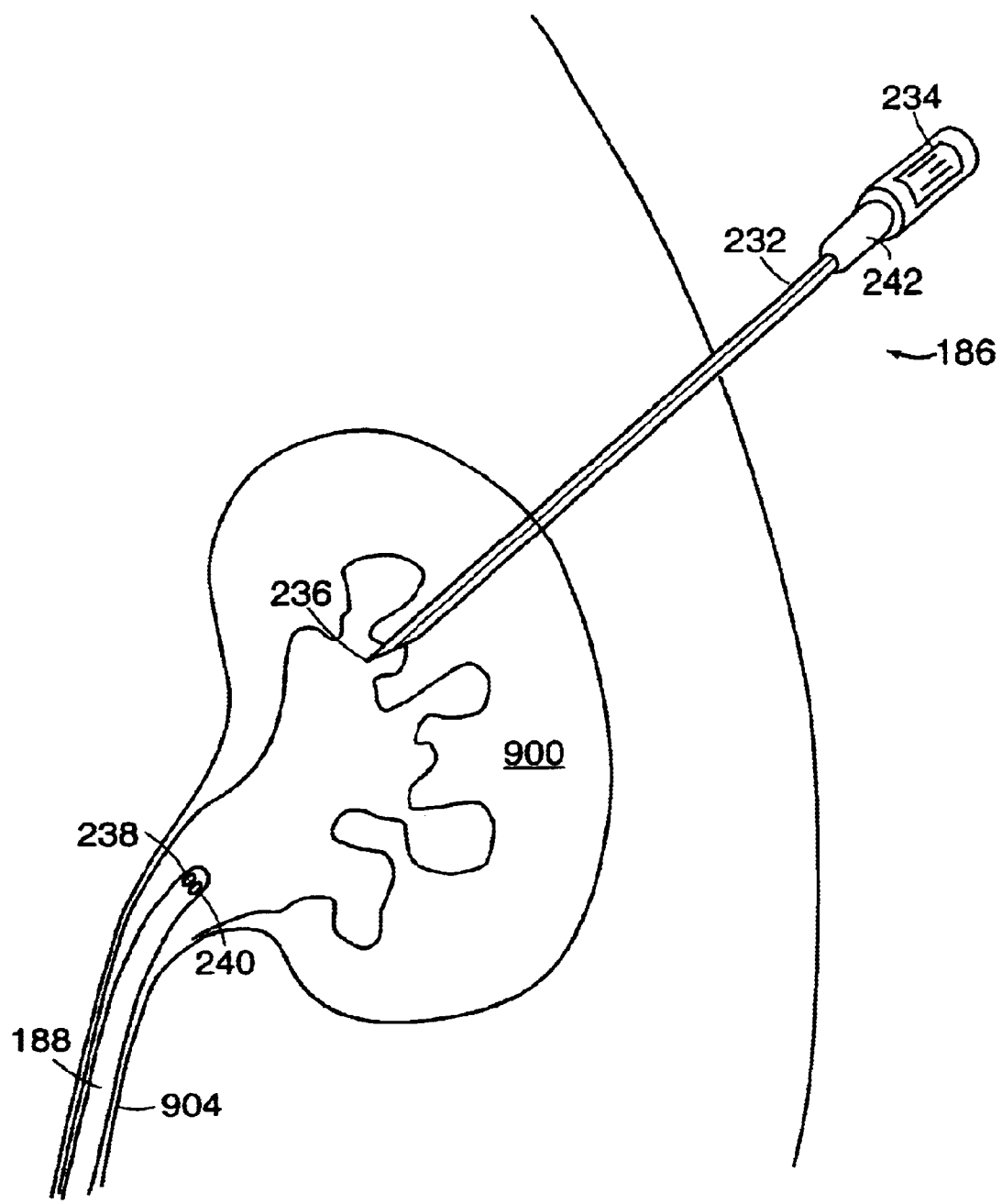
FIG. 24 depicts a schematic side view of an entry needle that senses electromagnetic radiation.

In another embodiment of a of an entry needle 186, shown in FIG. 24, the entry needle 186 is capable of sensing entry into the target calyx of a kidney 900 by sensing, for example, light. A fiber optic light source 188 can be inserted into the kidney 900, for example through a ureter 904 into the kidney 900, and can emit light. The fiber optic light source 188 can have other optional functions, for example, the source 188 can include a passage 240 for delivering contrast dye to the kidney 900 to visualize the kidney under the fluoroscope and/or the source 188 can have an inflatable balloon (not shown) for inflating and blocking dye from exiting the kidney 900 through the ureter 904. The entry needle 186 has a cannula 232 connected with a hub 242. Inside the cannula, a fiber optic core 236 for sensing light within the kidney 900 is provided. The core 236 transmits light through the cannula 232 to the hub 242. In the hub 242, a device 234, such as a light magnifier, magnifies the light received through the core 236 for display to a medical professional. Again, this embodiment can save time during the procedure because target access can be confirmed without the additional steps required by current designs.

Figure 25:
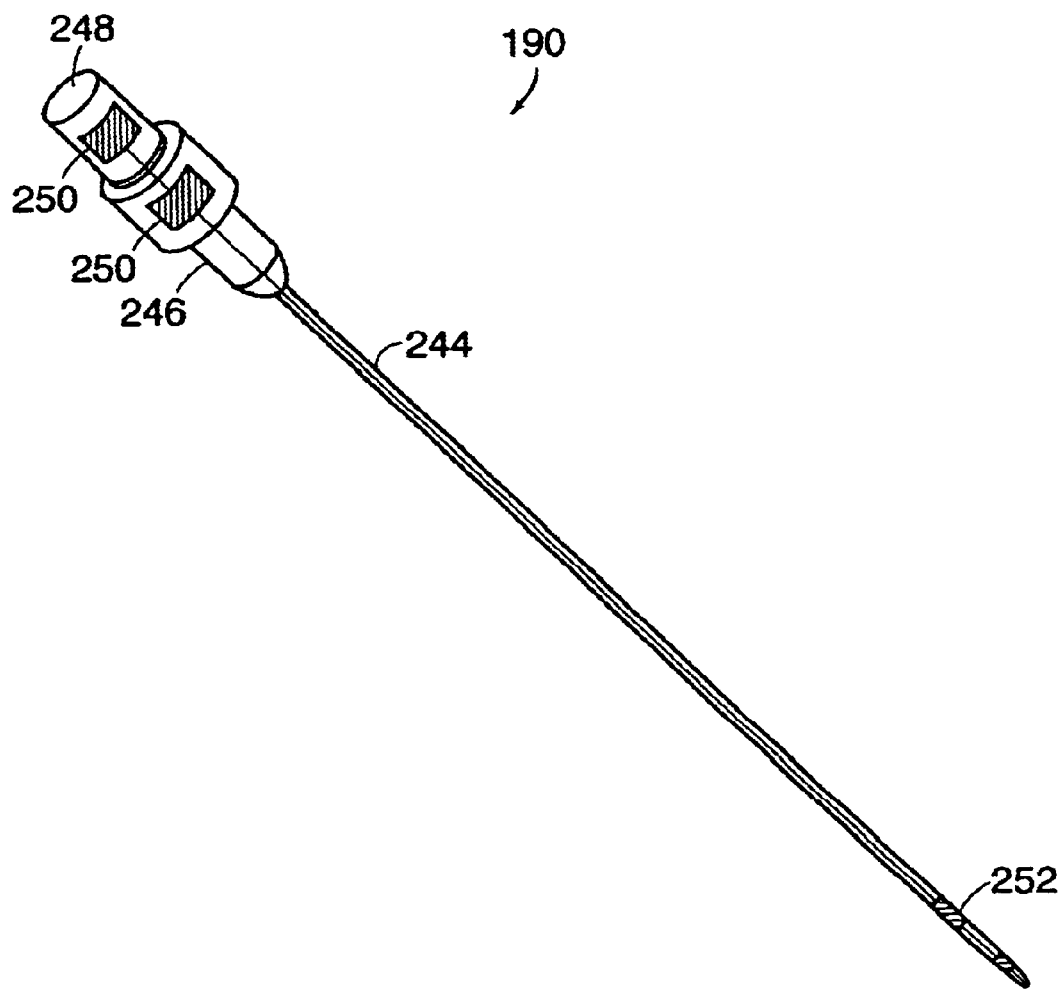
FIG. 25 depicts a schematic side view of an entry needle that has a chemical reaction sensor.
Figure 28:
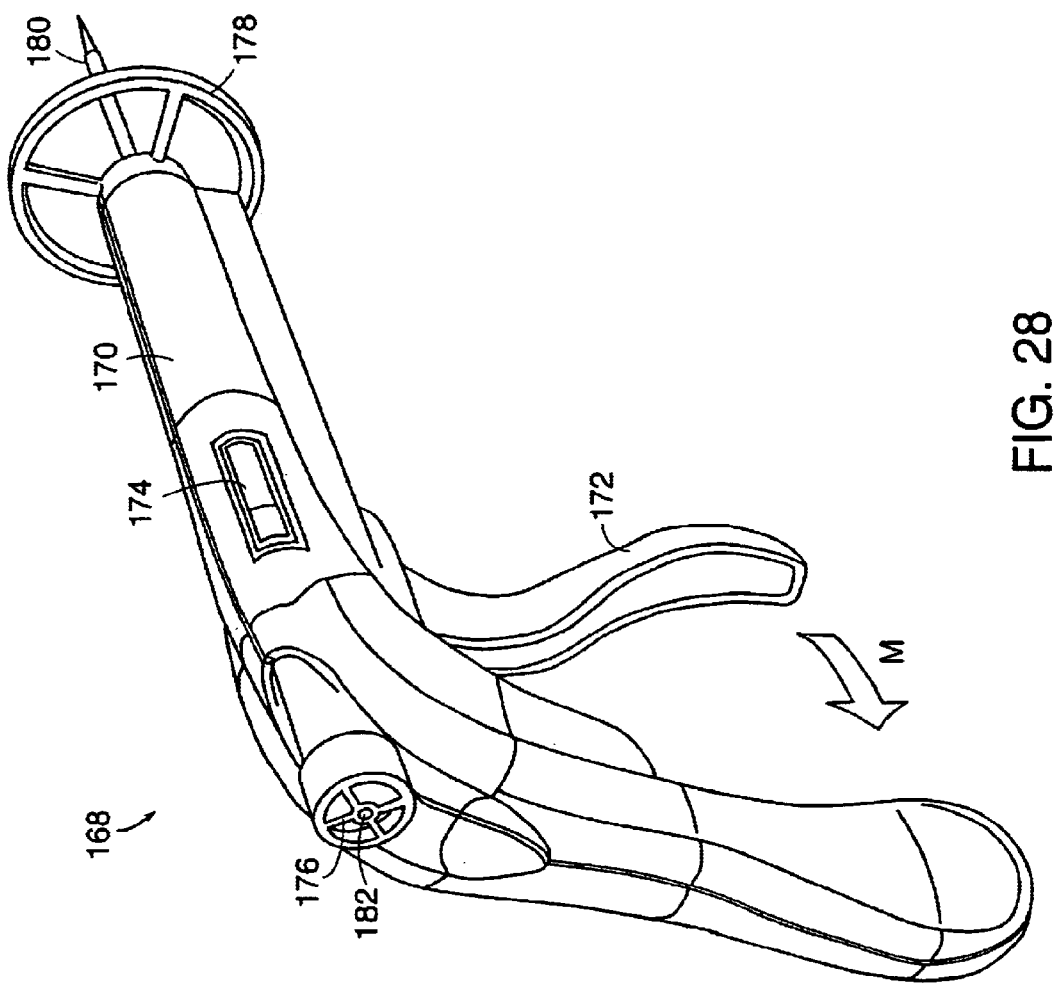
FIG. 28 depicts a schematic perspective view of a device having a trigger for driving an entry needle.
Figure 29:
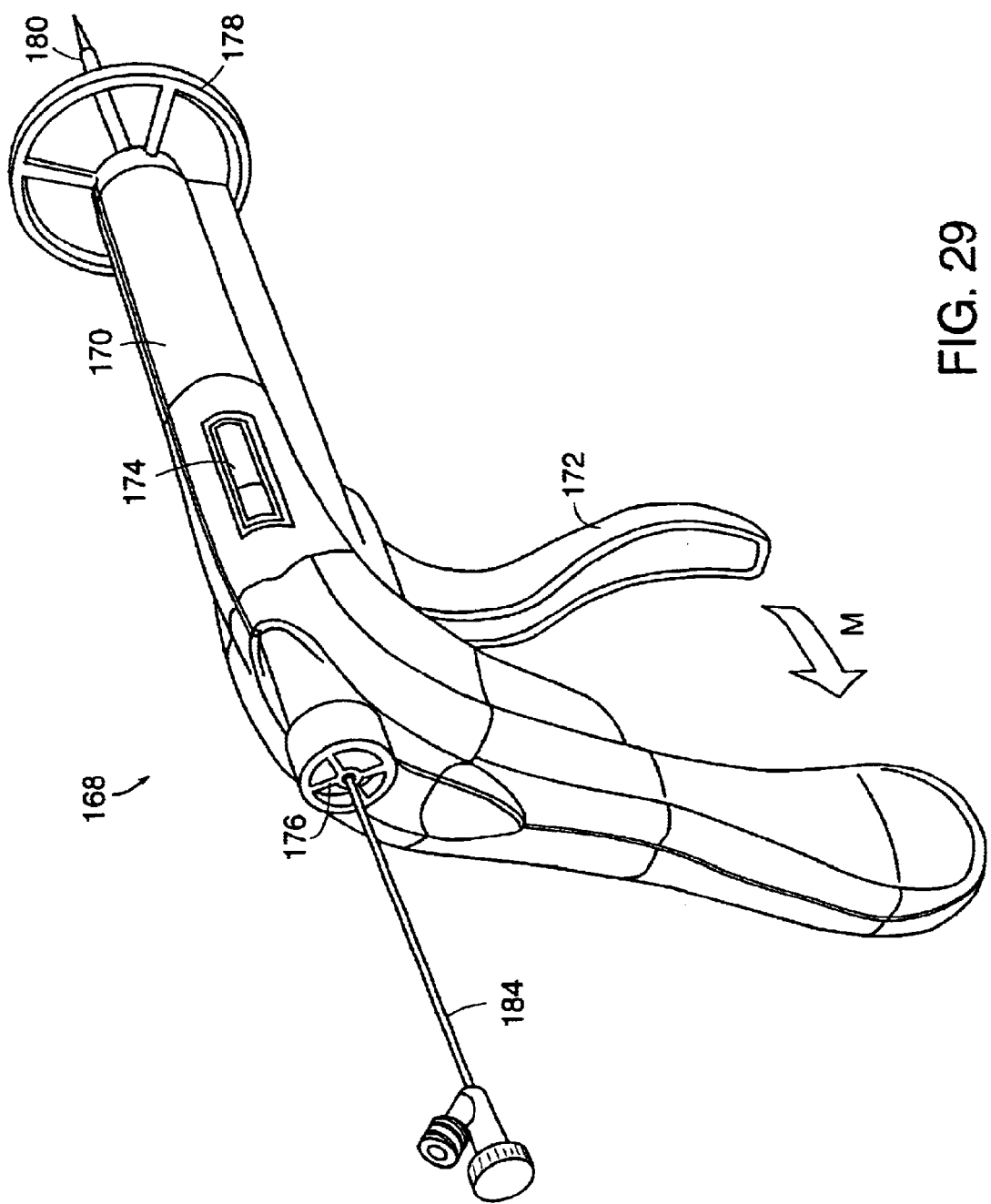
FIG. 29 depicts a schematic perspective view of the device of FIG. 28 with an entry needle of FIG. 22.
Figure 30:
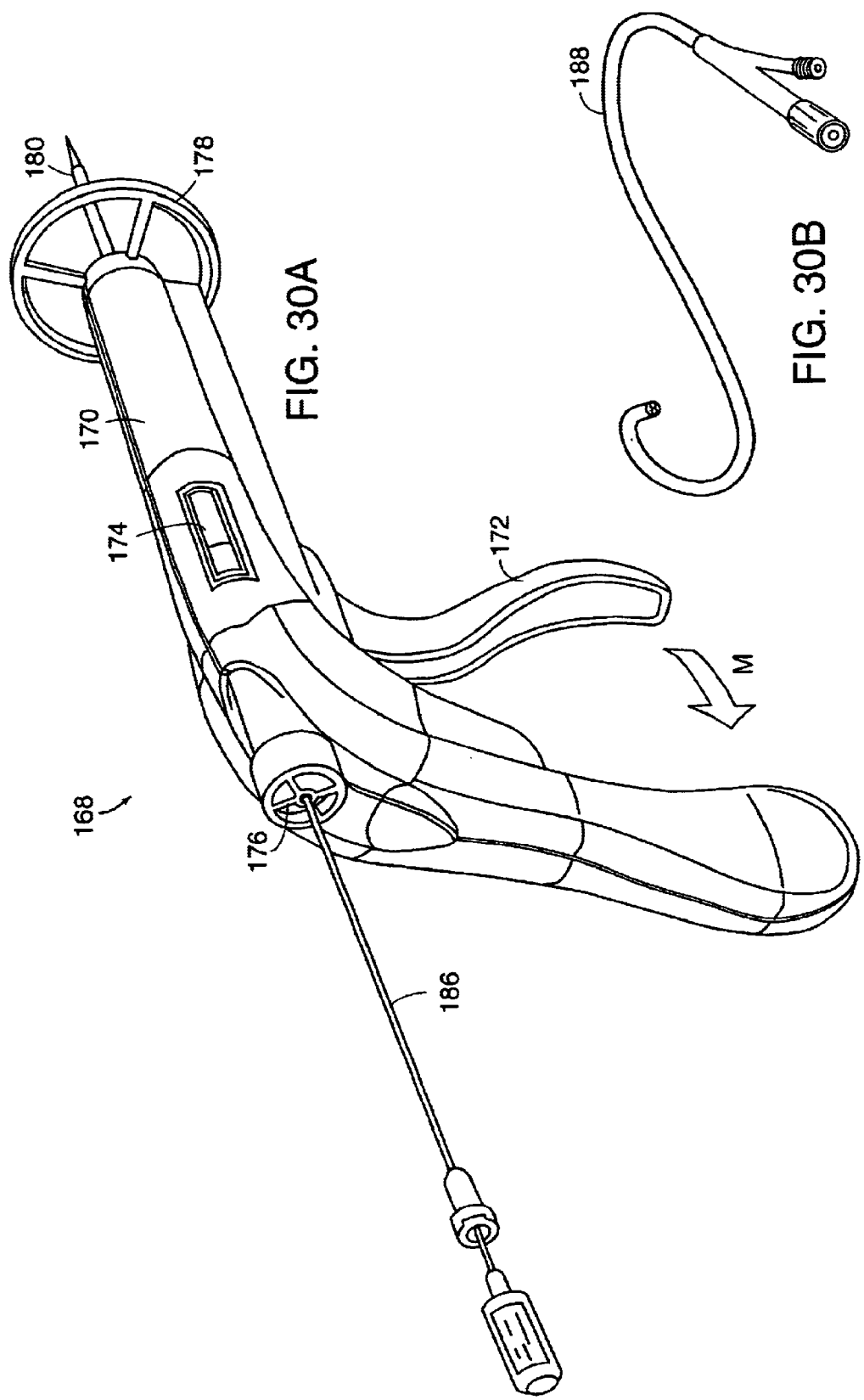
FIG. 30A depicts a schematic perspective view of the device of FIG. 28 with an entry needle of FIG. 24.
FIG. 30B depicts a schematic view of a device to provide electromagnetic radiation to the device of FIG. 30A.

In another embodiment of an entry needle 190, shown in FIG. 25, the entry needle 190 is capable of sensing entry into the target calyx of a kidney with, for example, a chemical reaction. The entry needle 190 has a cannula 244 connected to a hub 246 at the proximal end of the entry needle 190. An inner needle with a cap 248 (needle portion not shown) is located within the cannula 244 and is selectively removable to, for example, insert a guide wire. A reaction center 252 is located at the distal end of the cannula 224. This reaction center 252 can operate in a variety of manners such that a signal is produced at an indicator 250. The indicator 250 can be located at one of or both of the hub 246 or the cap 248. A chemical reaction can occur at the tip of the needle 190 to produce a signal at the hub 246 or cap 248. For example, urine and/or contrast dye in the kidney could react with a substance at the tip of the needle 190 such that the reaction completes a circuit or allows a circuit to be completed so that an indicator 250 illuminates with the completion of a circuit (or the device vibrates or the device makes an audible noise with the completion of a circuit). The reaction center 252 can be made to distinguish between the inside of a kidney (with such contents as urine and/or contrast dye) and the surrounding tissue (including blood). Alternatively, the reaction center 252 could sense an optical property at the tip of the needle 190, and if the optical property met a certain criterion or criteria, then a signal would be generated in the proximal portion of the needle 190, such as at the hub 246 or cap 248. For example, the needle 190 could detect light absorbance at certain wavelengths or reflection of high energy electromagnetic radiation pulses (e.g., laser pulses), with the light absorbance at a particular wavelength or the reflection of energy being indicative of the presence of a substance such as a contrast dye, indicating access to the target. In another embodiment, fluid can be drawn into the cannula, and the chemical reaction can take place anywhere along the length of the needle. Again, this embodiment can save time during the procedure because target access can be confirmed without the additional steps required by current designs.

Figures 42A, 42B, 42C:
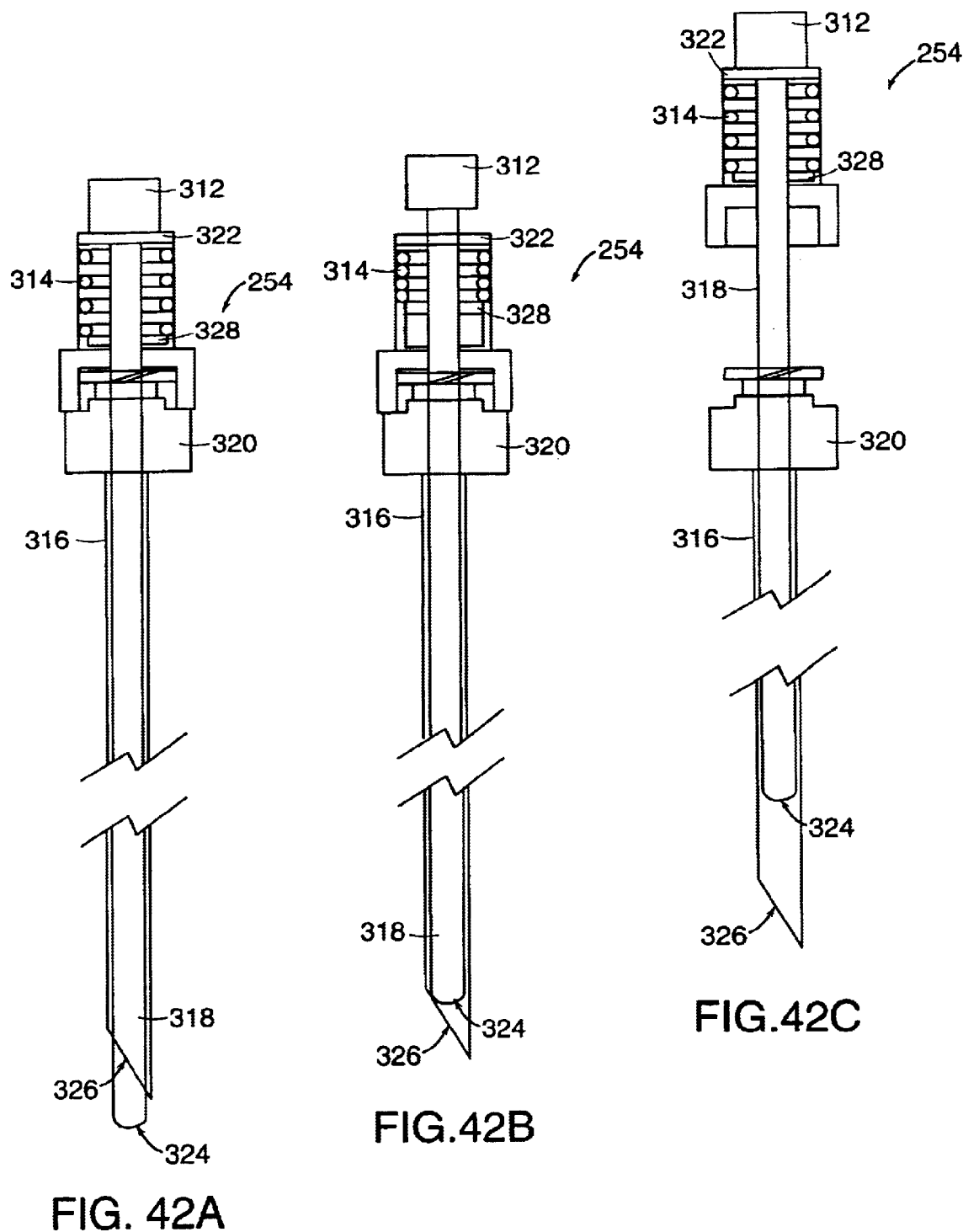
FIG. 42A depicts a schematic sectional view of one embodiment of an entry needle with a blunt-edged stylet and an angled-edge cannula.
FIG. 42B depicts a schematic sectional view of the embodiment of FIG. 42A with the stylet pushed proximally.
FIG. 42C depicts a schematic sectional view of the embodiment of FIG. 42A as the stylet is removed from the cannula.

In another embodiment of an entry needle 254, shown in detail in FIGS. 42A–42C, the entry needle 254 can indicate entry into a target structure such as a target calyx. Now referring to FIG. 42A, a housing 322 contains a spring 314 surrounding a stylet 318. The stylet 318 is attached to a hub 312. A structure (not shown) may intervene between the stylet and the hub so that they are not in direct contact, but they are connected. The stylet 318 has an extension 328 (for example, a piece of material that is connected with or a unitary part of the stylet 318 and that may encircle all or a portion of the stylet 318) that contacts the spring 314, such that the spring 314 is enclosed within the housing 322 and contacts the housing 322 at the proximal end of the housing 322 and contacts the extension 328 at a more distal position in the housing 322. The stylet 318 is disposed within a cannula 316. In this embodiment the stylet 318 is coaxially disposed within the cannula 316. A connector 320 is located at the proximal end of the cannula 316 such that it seals with the cannula 316. The housing 322 has a distal portion that engages the connector 320. The spring 314 biases the stylet 318 and hub 312 towards the distal end of the entry needle 254. The stylet 318 has a blunt edge 324 at its distal end, and the cannula 316 has a angled edge 326 (that can be sharp) at its distal end. The angled edge 326 of the cannula 316 can facilitate movement through a patient's tissue. When the entry needle 254 is inserted into tissue, the stylet 318 is pushed towards the proximal end of the entry needle 254 by the tissue (shown in FIG. 42B). Due to resistance from the tissue against the stylet 218, the spring 314 is compressed as the extension 328 is pushed proximally along with the rest of the stylet 318. Additionally, as the stylet 318 is pushed distally, the hub 312 raises from the housing 322 in a proximal direction, indicating the presence of tissue at the distal end of the entry needle 254. Additionally, as shown in FIG. 42C, the housing 322, stylet 318, and hub 312, as an assembly, can be removed from the cannula 216 and connector 320. Removal can occur, for example, when the cannula 216 is desired to be connected to a syringe (not shown) to sample fluids at the distal tip of the cannula 326 and/or when a guide wire is to be inserted through the cannula 316.

Figure 45:
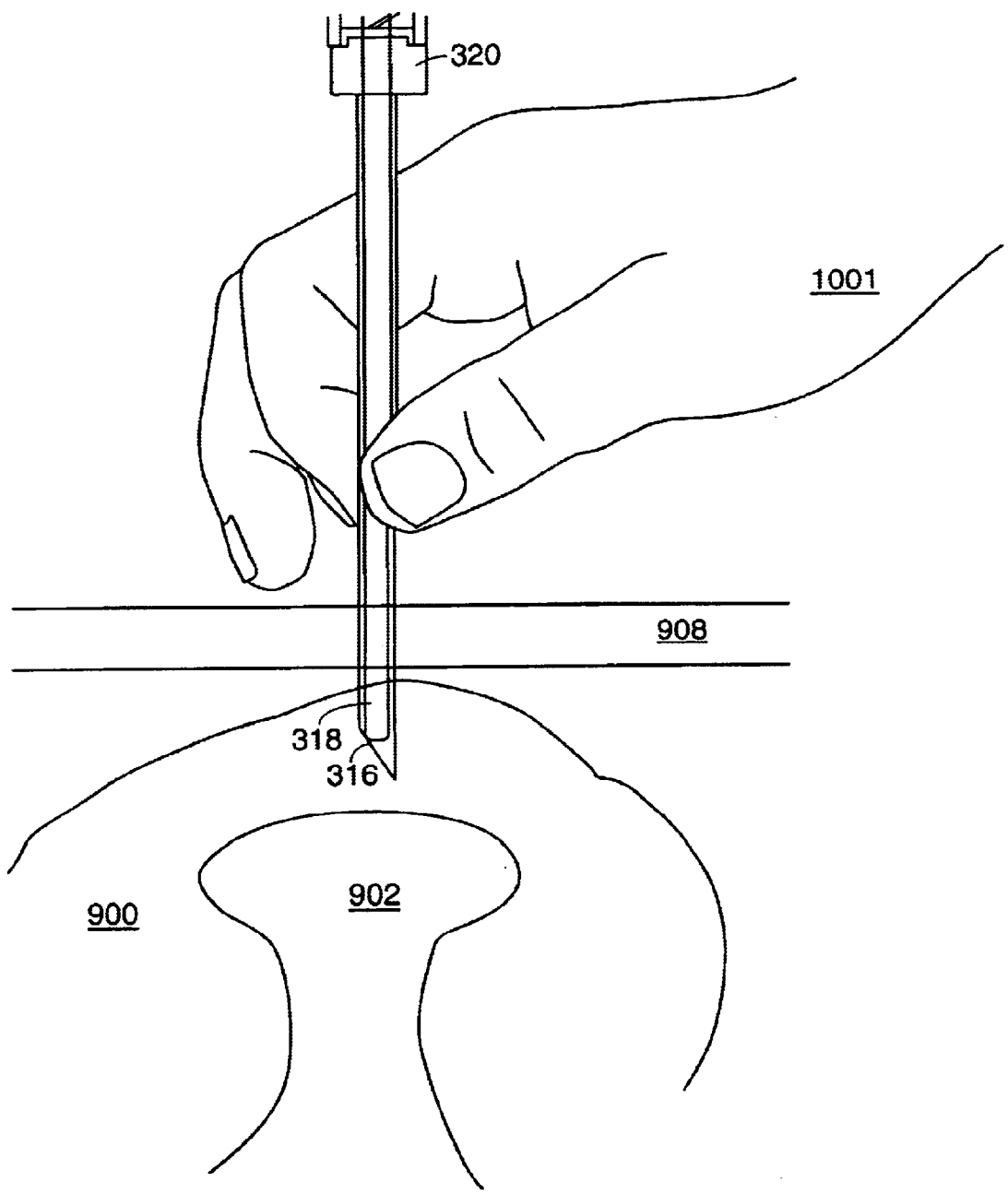
FIG. 45 depicts a close-up a schematic sectional view, similar to that shown in FIG. 44A, of the embodiment of FIG. 42A as the entry needle enters a kidney.
Figure 48C:
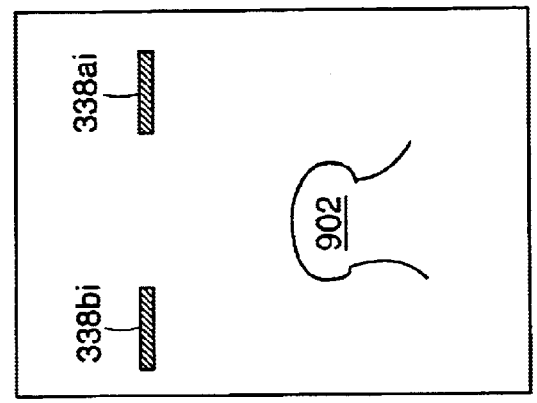
FIG. 48C depicts a schematic image display with the device of FIG. 48A in the position indicated in FIG. 48B.
Figure 48A:
FIG. 48A depicts a schematic side view of a portion of a slightly altered embodiment of the device of FIG. 31 for use with an MRI device or a CAT-scan device.
Figure 48B:
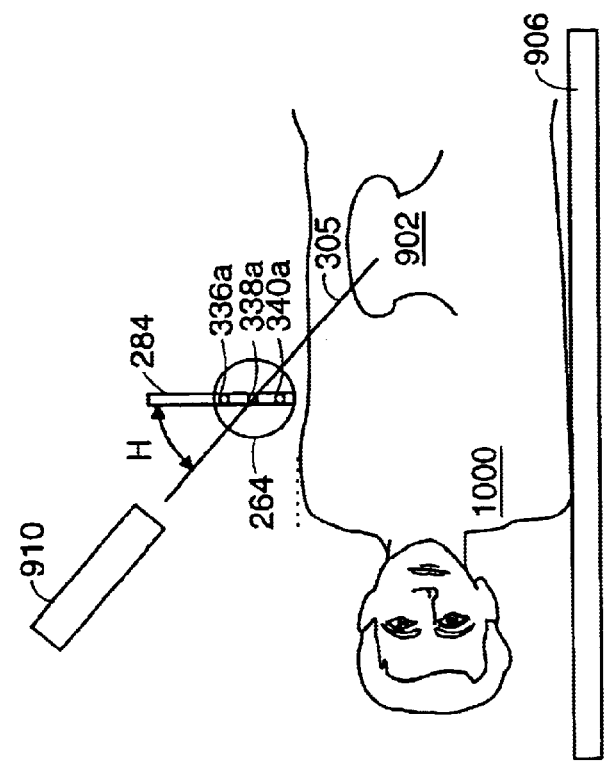
FIG. 48B depicts a schematic end view of a slightly altered embodiment of the device of FIG. 31 that is not aligned with a target and that is for use with an MRI device or a CAT-scan device.

One example of operation of the entry needle 254 is shown in FIGS. 44A–44D and FIG. 45. In FIG. 42A, the entry needle 254 is inserted through a patient's skin 908 and into the kidney 900. The resistance from the patient's tissue causes the stylet 318 to move proximally, compresses the spring 314, and raises the hub 312. FIG. 45 shows an enlarged view of the position shown in FIG. 44A with the entry needle 254 held by a medical professional 1001. As the entry needle 254 enters the target calyx 902 (characterized by an absence of dense tissue such as that surrounding the target calyx 902) in the kidney 900, the spring 314 decompresses in the absence of resistance from the patient's tissue. The stylet 318 moves distally and the hub 312 lowers, indicating entry into the target calyx 902. The entry needle 254 would work in most instances where the target is a cavity or void. The blunt edge of the stylet 318 in this embodiment is an added measure of safety because when the stylet 318 extends distally, if there is any inadvertent contact with tissue within the calyx, the contact will be relatively benign due to the blunt edge. Once entry occurs, the stylet 318, hub 312, and housing 322, as an assembly, are removed from the connector 320 and cannula 316 (FIG. 44C), leaving the connector 322 and cannula 316 behind as an assembly (FIG. 44D). The cannula 316 is still located in the target calyx 902, and, optionally, a syringe (not shown) can be attached to the connector 320 to sample fluid at the tip of the cannula 316 to confirm entry into the target calyx 902. Alternatively, a guide wire can be placed through the cannula 316 into the target calyx 902. The entry needle 254 also can be used in conjunction with a needle guiding apparatus, for example, as shown in FIG. 31. The entry needle 254 would indicate access to the target calyx 902 in the manner described above, but would be targeted using a needle guiding apparatus. This combination can further reduce the procedure time because not only is accuracy and ease of entry needle placement increased with needle guiding apparatus according to the invention, but also confirmation of access into the target calyx is simplified, for example, by viewing the raising and lowering of the hub of the entry needle according to the invention.

Figure 43A:
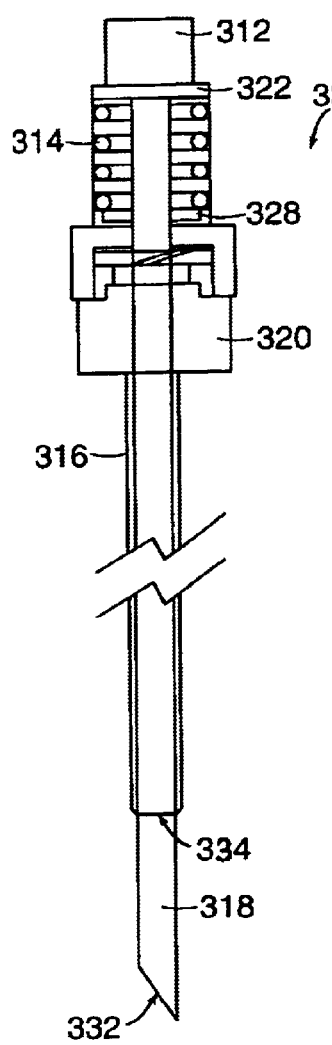
FIG. 43A depicts a schematic sectional view of one embodiment of an entry needle with an angled-edge stylet and an blunt-edge cannula.
Figure 43B:
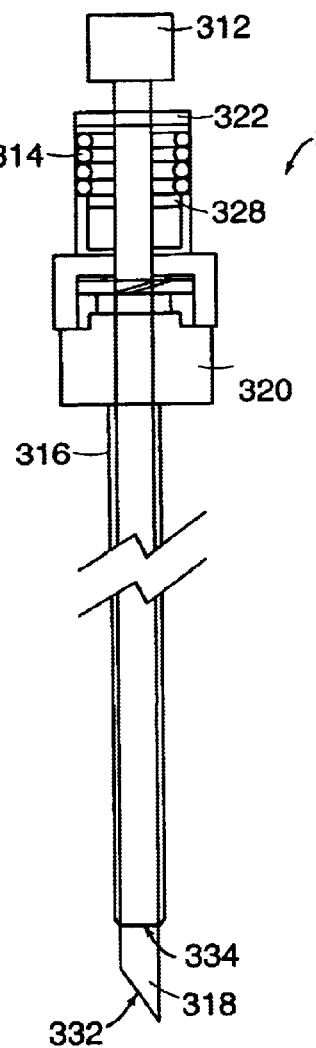
FIG. 43B depicts a schematic sectional view of the embodiment of FIG. 43A with the stylet pushed proximally.
Figure 43C:
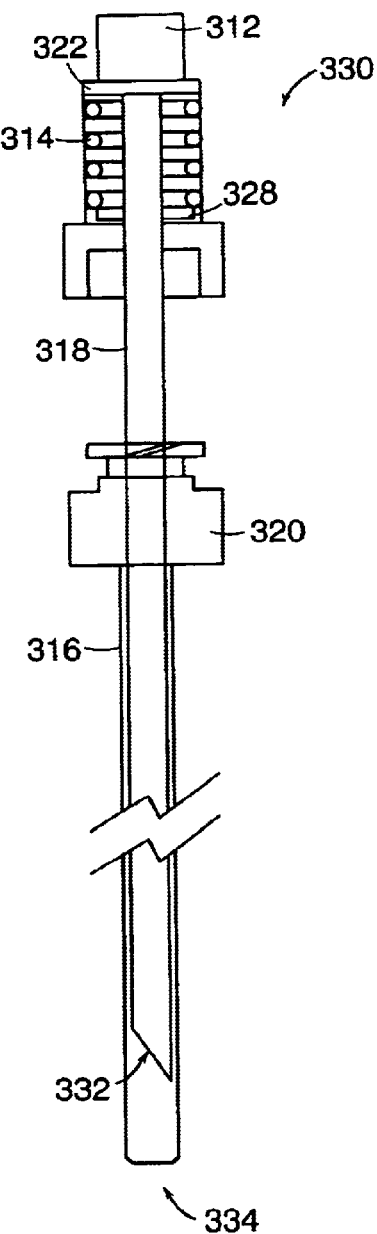
FIG. 43C depicts a schematic sectional view of the embodiment of FIG. 43A as the stylet is removed from the cannula.

In an alternative embodiment of the entry needle 254 shown in FIGS. 42A–42C, an entry needle 330 with a different distal end configuration is shown in FIGS. 43A–43C. The entry needle 330 has the same components as the entry needle 254 shown in FIGS. 42A–42C except that the distal end of the stylet 318 has an angled edge 332 and the distal end of the cannula 316 has a blunt edge 334. The angled edge 332 of the stylet 318 can be sharp to facilitate movement of the stylet 318 through a patient's tissue. Referring to FIG. 43A, the entry needle 330 is in a starting position similar to that shown in FIG. 42A. As shown in FIG. 43B, as the stylet 318 is pushed through tissue, the stylet 318 is pushed towards the proximal end of the device 330, the spring 314 is compressed, and the hub 312 raises, indicating that the tip of the device 330 is in a more dense tissue. However, the entry needle 330 is designed such that the stylet 318 does not retract fully into the cannula 318 (as it does in the embodiment shown in FIG. 42B). Thus, the angled edge 332 of the stylet 318 is exposed to tissue as the device 330 is inserted into a patient. When the entry needle 330 enters a cavity, such as a target calyx, the spring 314 decompresses, the stylet 318 moves towards the distal end of the entry needle 330, and the hub 312 lowers, indicating entry into the cavity. The hub 312, housing 322, and stylet 318 can be removed as an assembly from the cannula 316 and connector 320, as shown in FIG. 43C. The cannula 316 and connector 320 are left behind as an assembly, positioned within the patient. A syringe (not shown) optionally can be attached to the connector 320 to withdraw fluids and confirm access to the target, and/or a guide wire can be inserted down the cannula 316. The entry needle 330 can be useful in situations besides gaining access to the kidney or other cavities including procedures to gain access to cardiovascular system vessels. The indicator hub 312 would indicate access into a vessel without blood being ejected from the patient, and a guide wire could be inserted.

Any of the entry needles according to the invention, in addition to other entry needles not specifically described herein, are useable with needle guiding apparatus according to the invention.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A needle guiding apparatus comprising:
   a base defining an opening extending therethrough;
   a guide assembly including at least one passage and being disposed within the opening, the guide assembly being rotatable about at least one axis extending therethrough; and
   an imaging sight disposed adjacent the at least one passage.

2. The apparatus of claim 1 wherein the guide assembly comprises a first transmission element between a first location within the opening and a second location remote therefrom, the first transmission element for transferring angular movement between the second location and the first location, the movement at the first location occurring about a first one of the at least one axis.

3. The apparatus of claim 2 wherein the first transmission element comprises a first pulley proximate the first location and disposed coaxially with the first axis of rotation.

4. The apparatus of claim 3 wherein the first transmission element further comprises a guide shaft defining at least a portion of the at least one passage.

5. The apparatus of claim 2 wherein the first transmission element comprises a belt for transferring angular movement between the first location an the second location.

6. The apparatus of claim 3 wherein the first transmission element further comprises a control shaft connected to a second pulley proximate the second location.

7. The apparatus of claim 6 further comprising a lock for preventing movement of the first transmission element.

8. The apparatus of claim 2 wherein the guide assembly further comprises a second transmission element for transferring angular movement about a second one of the at least one axis.

9. The apparatus of claim 8 wherein the second transmission element comprises an adjustment rod rotatable about the second axis extending through the adjustment rod.

10. The apparatus of claim 9 wherein the imaging sight comprises a radiopaque core of the adjustment rod.

11. The apparatus of claim 9 further comprising a lock for preventing movement of the adjustment rod.

12. The apparatus of claim 9 wherein the imaging sight comprises at least two parallel bands disposed within the adjustment rod.

13. The apparatus of claim 8 wherein the first axis and the second axis are substantially perpendicular.

14. The apparatus of claim 1 wherein the imaging sight comprises a radiopaque band disposed within the base.

15. The apparatus of claim 1 wherein the guide assembly comprises an adjustment rod.

16. The apparatus of claim 15 wherein the adjustment rod is rotatable about an axis extending through the adjustment rod.

17. The apparatus of claim 15 wherein the adjustment rod is rotatable about an axis extending through the at least one passage.

18. The apparatus of claim 1 wherein the guide assembly comprises a turret disposed within the opening.

19. The apparatus of claim 18 wherein the turret includes an adjustment rod.

20. The apparatus of claim 19 wherein the turret is rotatable about an axis extending through the opening.

21. The apparatus of claim 19 wherein the adjustment rod is rotatable about an axis extending through the adjustment rod.

22. The apparatus of claim 1 wherein the guide assembly comprises a guide needle.

23. The apparatus of claim 1 wherein the guide assembly comprises a ball and socket joint disposed within the base.

24. The apparatus of claim 23 wherein the guide assembly further comprises a guide shaft defining a portion of the at least one passage.

25. The apparatus of claim 23 further comprising a control arm connected to the guide assembly.

26. The apparatus of claim 25 further comprising a second ball and socket joint connected to the control arm, thereby to replicate the movement of the second ball and socket joint at the guide assembly.

27. The apparatus of claim 26 wherein the second joint is capable of locking into a position.

28. The apparatus of claim 1 wherein the imaging sight is disposed coaxially about the at least one passage.

29. The apparatus of claim 1 wherein the imaging sight comprises a ring.

30. The apparatus of claim 1 wherein the imaging sight comprises at least one cross-hair.

31. The apparatus of claim 1 wherein the imaging sight includes a material that is detectable with a fluoroscope.

32. The apparatus of claim 31 wherein the material that is detectable with a fluoroscope comprises a radiopaque material.

33. The apparatus of claim 1 wherein the guide assembly includes at least two of the passages disposed at known angles relative to the base.

34. The apparatus of claim 1 further comprising at least one clamp for attaching the apparatus to a fixed surface.

35. The apparatus of claim 1 wherein the guide assembly is capable of locking into a position.

36. The apparatus of claim 1 wherein the guide assembly is rotatable about at least two axes and wherein at least two of the axes are substantially perpendicular.

37. The apparatus of claim 1 wherein the guide assembly does not protrude past at least one side of the base.

38. A needle guiding apparatus comprising:
   a base defining an opening extending therethrough;
   a guide assembly comprising a turret rotatably mounted in the opening and an adjustment rod rotatably mounted in the turret, the guide assembly including at least one passage therethrough; and
   an imaging sight disposed adjacent at least one passage.

39. The apparatus of claim 38 wherein the turret includes a groove for interlocking with pins from the base, thereby to allow rotation of the turret within the base.

40. The apparatus of claim 38 wherein the turret is associated with the base using a friction fit, thereby to allow rotation of the turret within the base.

41. The apparatus of claim 38 wherein the guide assembly does not protrude beyond at least one side of the base.

42. A needle guiding apparatus comprising:

a base including a socket;

a guide assembly including at least one passage therethrough and including a ball articulable within the socket and a guide shaft proximate the ball; and an imaging sight disposed adjacent at least one passage.

43. The apparatus of claim 42 further comprising a connecting rod in operable connection with the guide assembly and with a mechanism, the mechanism being remote from the guide assembly, thereby to replicate movements of the mechanism at the guide assembly.

44. The apparatus of claim 43 wherein the mechanism comprises a base assembly including a socket, a ball being articulable in the socket, and a shaft proximate the ball.

45. The apparatus of claim 43 further comprising a lock, thereby to prevent movement of the guide assembly.

46. The apparatus of claim 42 wherein the base includes an opening extending therethrough and the guide assembly is disposed within the opening.

47. A needle guiding apparatus comprising a base, a dome, and a guide assembly including a stop and defining a passage, such that the guide assembly is positionable at various locations through the dome and the guide assembly does not protrude beyond at least one surface of the base.

48. The apparatus of claim 47 wherein the dome includes an imaging sight.

49. A needle guiding apparatus comprising:

a base defining an opening extending therethrough;

a guide assembly comprising a turret rotatable within the opening, the turret defining at least two passages therethrough, the passages being at known angles of entry relative to the base; and an imaging sight adjacent at least one passage.

50. A needle guiding apparatus comprising:

a base defining an opening extending therethrough;

a guide assembly comprising a guide needle including a passage therethrough, the guide needle being rotatable about an axis that extends through the base and is substantially perpendicular to the guide needle; and an imaging sight adjacent the passage.

51. The apparatus of claim 50 further comprising at least one driving bar for inserting an entry needle through the passage.

52. The apparatus of claim 51 further comprising at least one bar guide for sliding at least one driving bar along a predetermined range of motion.

53. The apparatus of claim 50 further comprising at least one driving bar for applying force to the guide assembly.

54. The apparatus of claim 53 further comprising at least one bar guide, wherein at least one driving bar is affixed to the at least one bar guide such that applied force is conveyed from the at least one driving bar to the guide assembly.

55. A needle guiding apparatus comprising:

a base defining an opening extending therethrough;

a guide assembly comprising an adjustment rod rotatable about an axis extending through the adjustment rod and a guide needle extending through the adjustment rod and defining a passage extending therethrough; and an imaging sight adjacent the passage.

56. The apparatus of claim 55 further comprising a lock for preventing movement of the alignment rod.

57. The apparatus of claim 55 further comprising at least one driving bar associated with an entry needle for applying force to the entry needle, the entry needle passing through the passage.

58. The apparatus of claim 57 further comprising at least one bar guide for sliding at least one driving bar along a predetermined range of motion.

59. The apparatus of claim 55 comprising at least one driving bar for applying force to the guide assembly.

60. The apparatus of claim 59 further comprising at least one bar guide, wherein at least one driving bar is affixed to the at least one bar guide such that applied force is conveyed from the at least one driving bar to the guide assembly.

* * * * *

UNITED STATES PATENT AND TRADEMARK OFFICE
CERTIFICATE OF CORRECTION

PATENT NO. : 6,689,142 B1
DATED : February 10, 2004
INVENTOR(S) : Anthony R. Tremaglio, Jr. et al.

It is certified that error appears in the above-identified patent and that said Letters Patent is hereby corrected as shown below:

Column 31,
Line 39, "location an the" should read -- location and the --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,689,142 B1 |
| DATED | : February 10, 2004 |
| INVENTOR(S) | : Anthony R. Tremaglio, Jr. et al. |

It is certified that error appears in the above-identified patent and that said Letters Patent is hereby corrected as shown below:

<u>Title page,</u>
Item [75], Inventors, "Anthony R. Tremaglio, Jr., Hopkinton, MA (US); Michael S. H. Chu, Brookline, MA (US); Tim E. Ward, Bedford, IN (US)" should read -- Anthony R. Tremaglio, Jr., Hopkinton, MA (US); Michael S. H. Chu, Brookline, MA (US); --.

Signed and Sealed this

Thirty-first day of August, 2004

JON W. DUDAS
*Director of the United States Patent and Trademark Office*